United States Patent [19]

Shishido et al.

[11] Patent Number: 5,360,803

[45] Date of Patent: Nov. 1, 1994

[54] COMPOSITION AND METHOD FOR TREATING CANCER

[75] Inventors: Tadao Shishido, Kanagawa, Japan; Lan B. Chen, Lexington, Mass.

[73] Assignees: Dan Farber Cancer Institute, Boston, Mass.; Fuji Photo Film Co., Ltd., Kanagawa, Japan

[21] Appl. No.: 972,935

[22] Filed: Nov. 6, 1992

Related U.S. Application Data

[63] Continuation-in-part of Ser. No. 744,130, Aug. 13, 1991, abandoned.

[51] Int. Cl.$^5$ ............ A61K 31/425; A61K 31/44; A61K 31/47; A61K 31/50
[52] U.S. Cl. ............ 514/224.2; 514/224.5; 514/229.5; 514/299.8; 514/257; 514/267; 514/279; 514/284; 514/285; 514/287; 514/290; 514/291; 514/292; 514/293; 514/365; 514/360; 514/369; 514/374; 514/375; 514/376; 514/387; 514/393; 514/434; 514/437; 514/443; 514/468
[58] Field of Search ............ 514/224.2, 224.5, 229.5, 514/229.8, 257, 267, 279, 284, 285, 287, 290, 291, 292, 293, 365, 366, 369, 374, 375, 376, 387, 393, 434, 437, 443, 468

[56] References Cited

U.S. PATENT DOCUMENTS

| | | | |
|---|---|---|---|
| 2,388,963 | 11/1945 | Fry et al. | 546/175 |
| 2,504,468 | 4/1950 | Thompson | 548/121 |
| 2,536,986 | 1/1951 | Thompson et al. | 548/180 |
| 2,961,318 | 11/1960 | Jones | 430/573 |
| 3,454,629 | 11/1948 | Brooker | 548/181 |
| 4,263,397 | 4/1981 | Horikoshi et al. | 430/543 |

FOREIGN PATENT DOCUMENTS

| | | |
|---|---|---|
| 11446 | 9/1988 | Australia . |
| 0286252 | 10/1988 | European Pat. Off. . |
| 286252 | 10/1988 | European Pat. Off. . |
| 417941 | 3/1991 | European Pat. Off. . |
| 832352 | 9/1938 | France . |
| 973859 | 2/1951 | France . |
| 55-31024 | 3/1960 | Japan . |
| 54-151133 | 11/1979 | Japan . |
| 55-69513 | 5/1980 | Japan . |
| 55-100318 | 7/1980 | Japan . |
| 1-054325 | 11/1989 | Japan . |
| 054325 | 11/1989 | Japan . |
| 154325 | 11/1989 | Japan . |
| 487051 | 6/1938 | United Kingdom . |
| 489335 | 7/1938 | United Kingdom . |
| 2020975 | 11/1979 | United Kingdom . |

OTHER PUBLICATIONS

Gaft et al. "Cyanine dyes as spectral sensitizers for photographic materials" Chemical Abstracts vol. 104, 1986 No. 139227p.

I. Minami et al., Chemical and Pharmaceutical Bulletin, vol. 30, No. 9, 1982, 3106–3120 Chemical Abstracts, vol. 93, 1980, Columbus, Ohio, U.S., Abstract No. 19532s, p. 94, col. 1.

Gaft et al., "Cyanine dyes as spectial sensitizers for photographic Materials" *Chemical Abstracts*, 104, No. 139227 (1986).

E. B. Knott, *J. Chem. Soc.*, 949 (1955).
E. B. Knott, *J. Chem. Soc.*, 4762 (1952).

*Primary Examiner*—Nathan M. Nutter
*Attorney, Agent, or Firm*—Sughrue, Mion, Zinn, Macpeak & Seas

[57] ABSTRACT

A pharmaceutical composition for treatment of cancer comprises:

(A) a therapeutically effective amount of at least one compound selected from the group consisting of compounds represented by the General Formula (I)

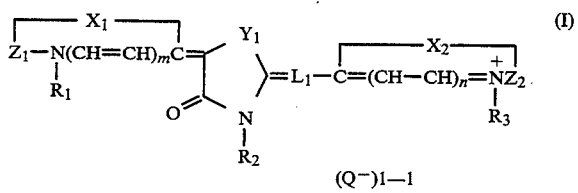

wherein
$X_1$ and $X_2$, which may be the same or different, each represents O, S, Se, —CH=CH—, (Abstract continued on next page.)

ABSTRACT

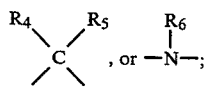

$Y_1$ represents O, S, Se, or

Figure 5:
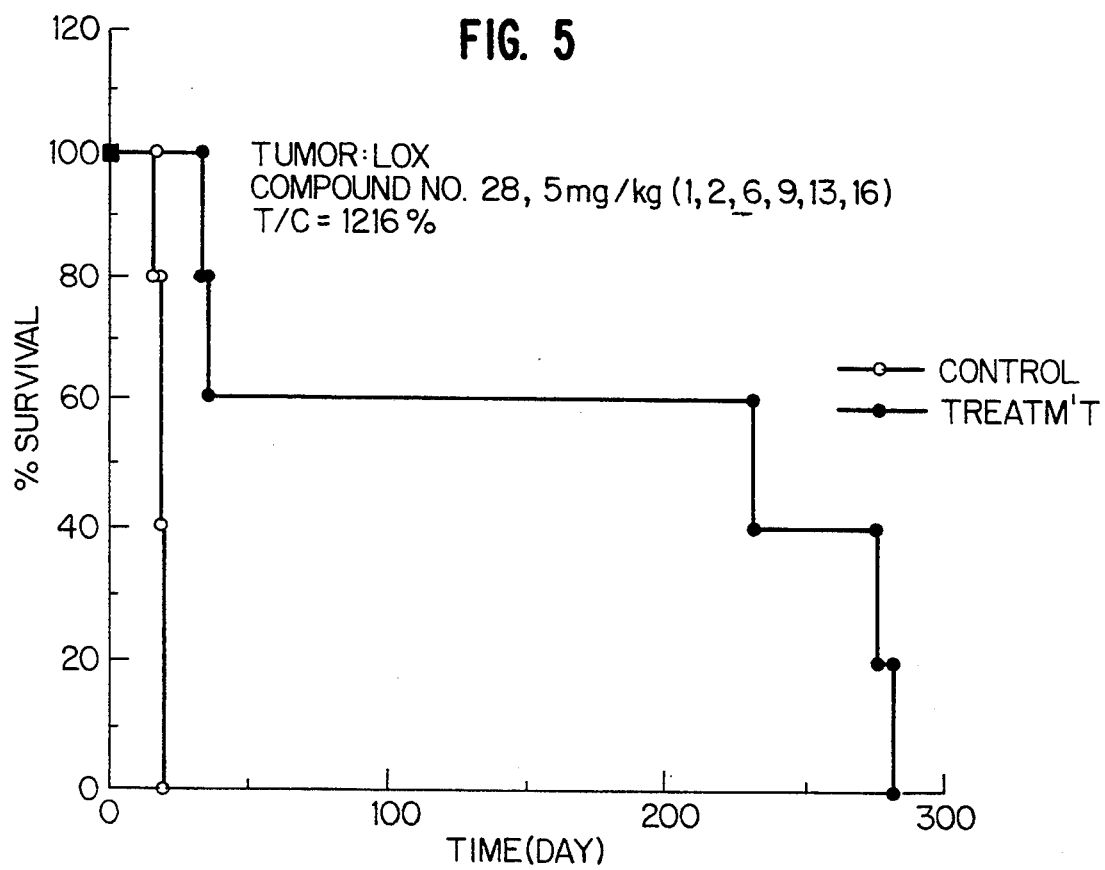

$R_1$ and $R_3$, which may be the same or different, each represents an alkyl group;

$R_2$ represents an alkyl group, an aryl group or a heterocyclic group;

$Z_1$ and $Z_2$, which may be the same or different, each represents an atomic group necessary to form a 5- or 6-membered ring;

$L_1$ represents a methine group or $L_1$ and $R_3$ may combine and form a 5- or 6-membered ring;

$R_4$ and $R_5$, which may be the same or different, each represents a alkyl group;

$R_6$ and $R_7$, which may be the same or different, each represents an alkyl group or an aryl group;

Q represents a pharmaceutically acceptable anion;

l represents 1 or 2;

m and n, which may be the same or different, each represents 0 or 1; and (B) a pharmaceutically acceptable carrier or diluent.

26 Claims, 15 Drawing Sheets

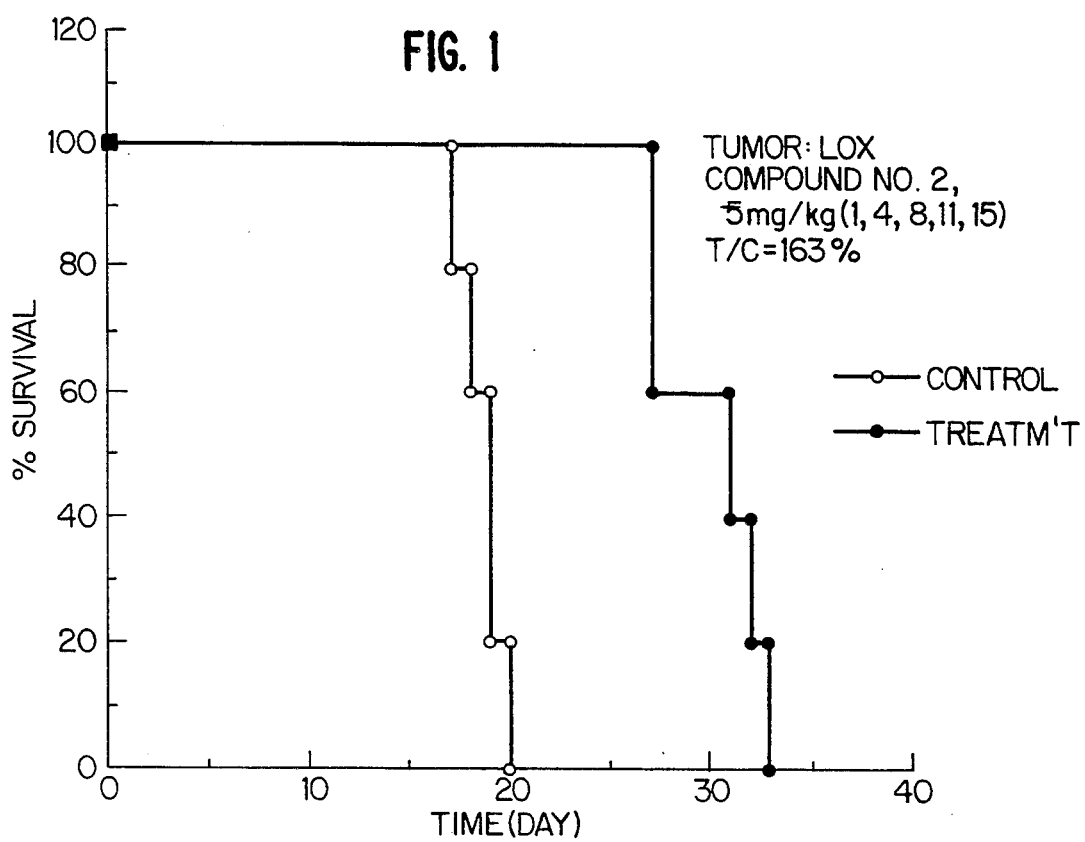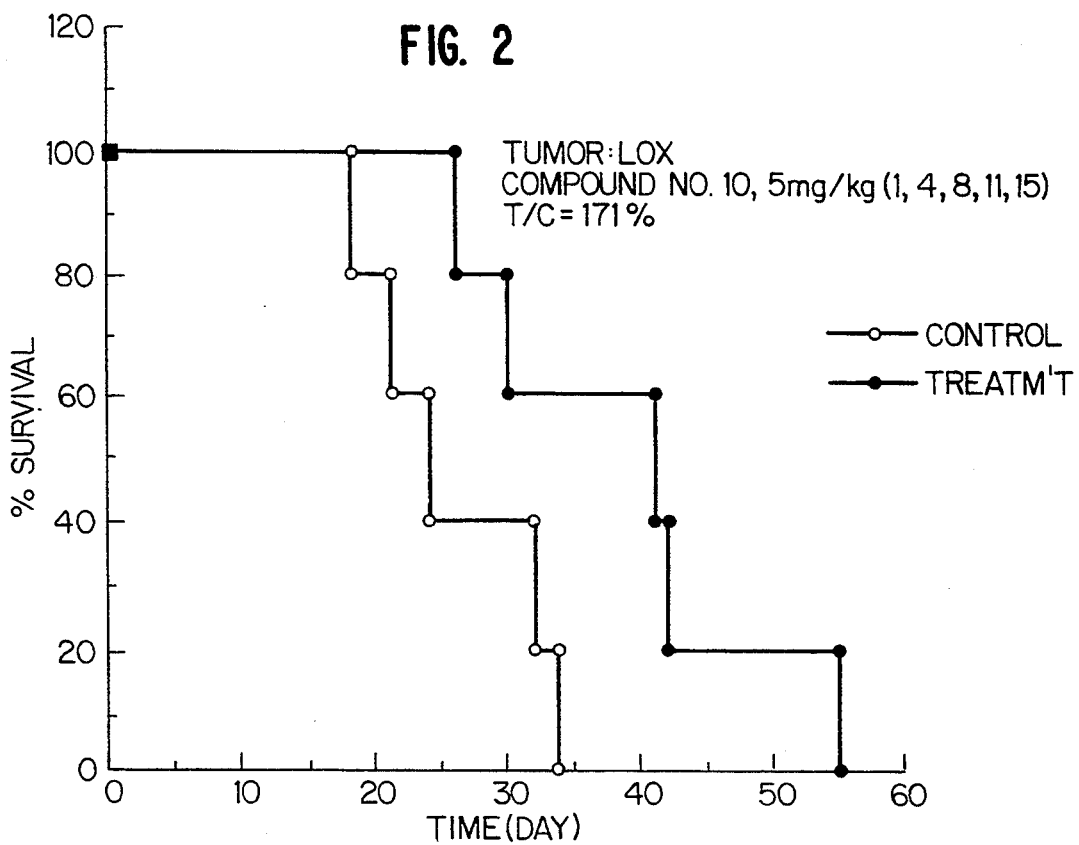

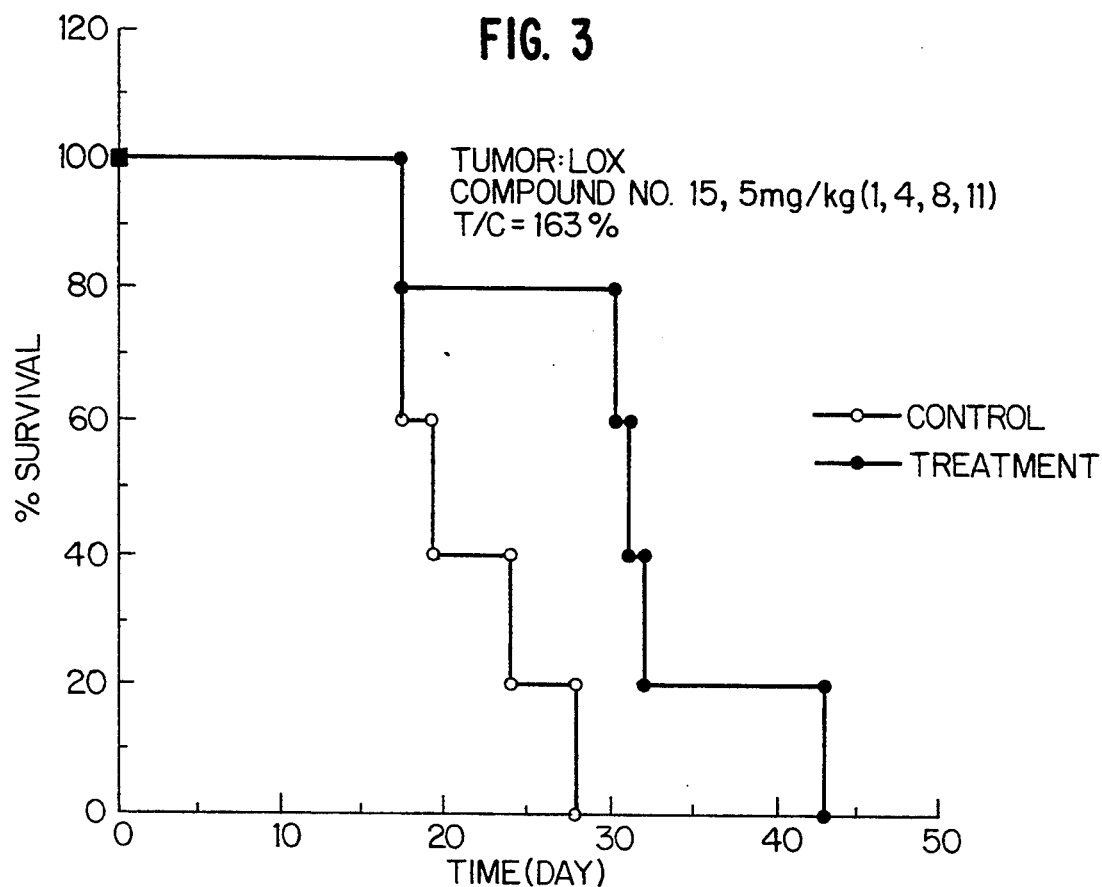
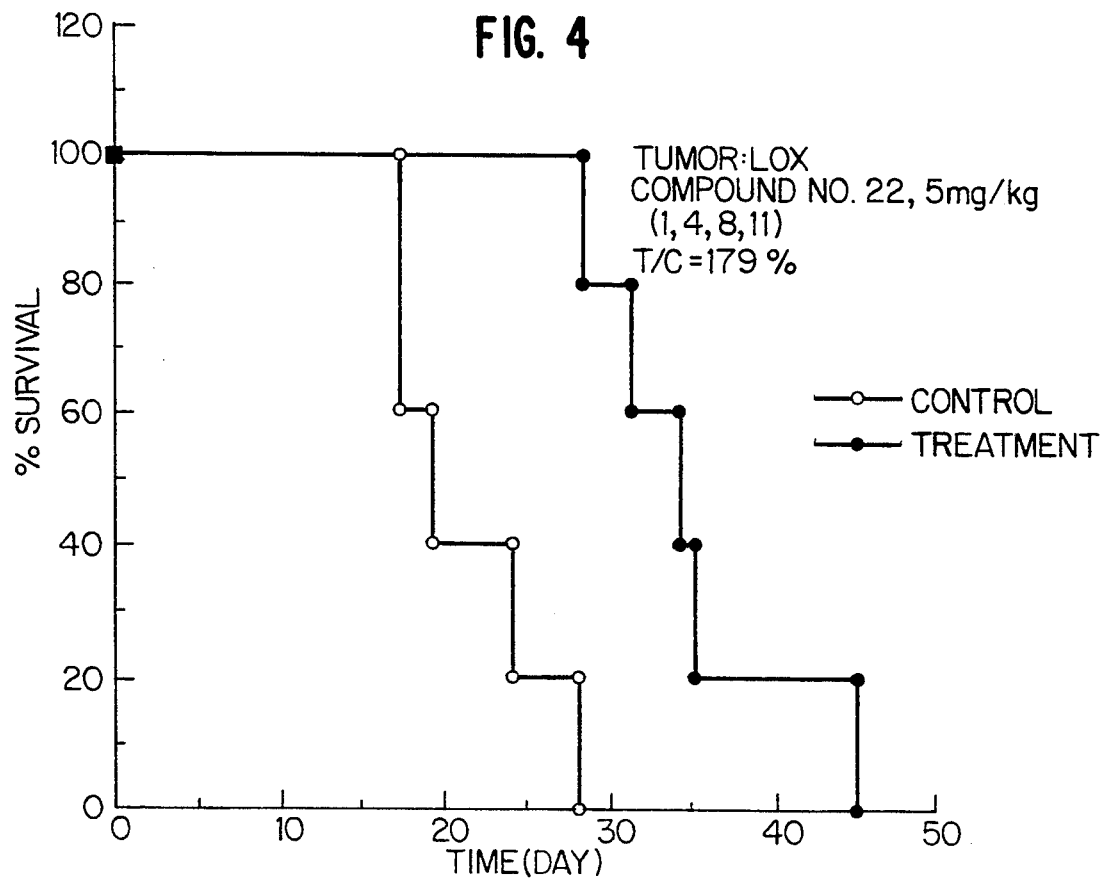

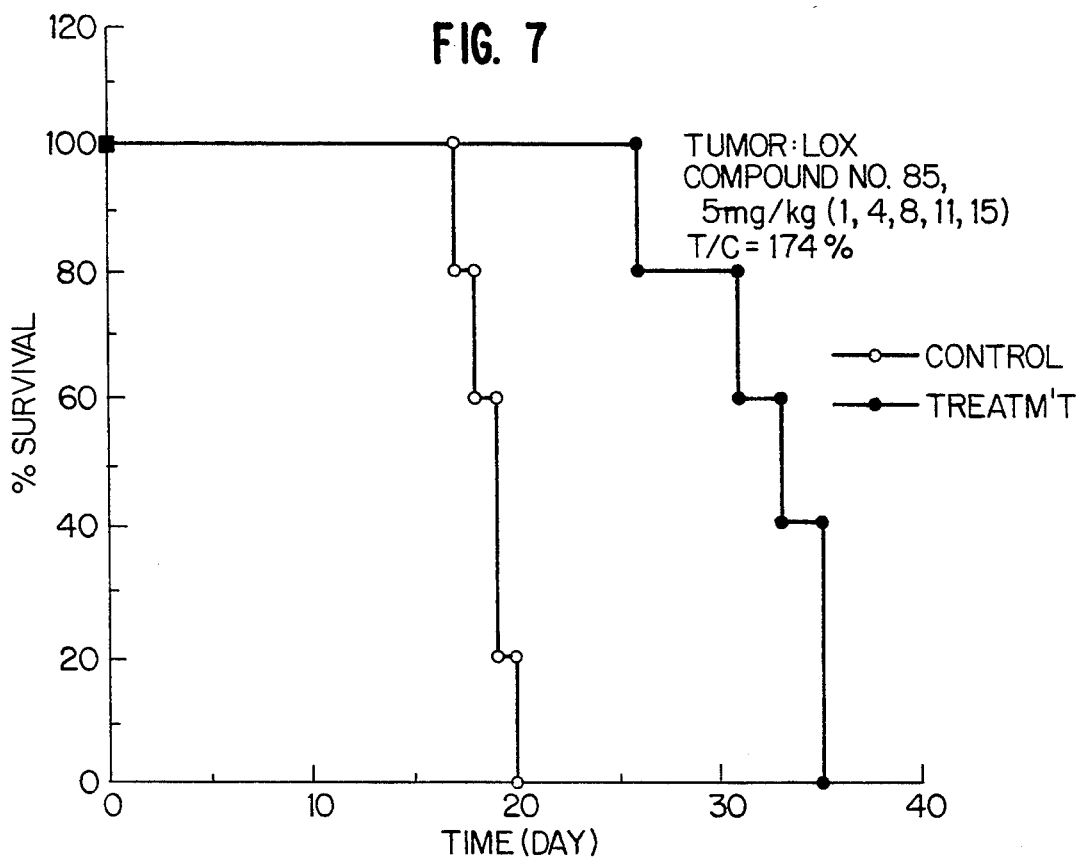
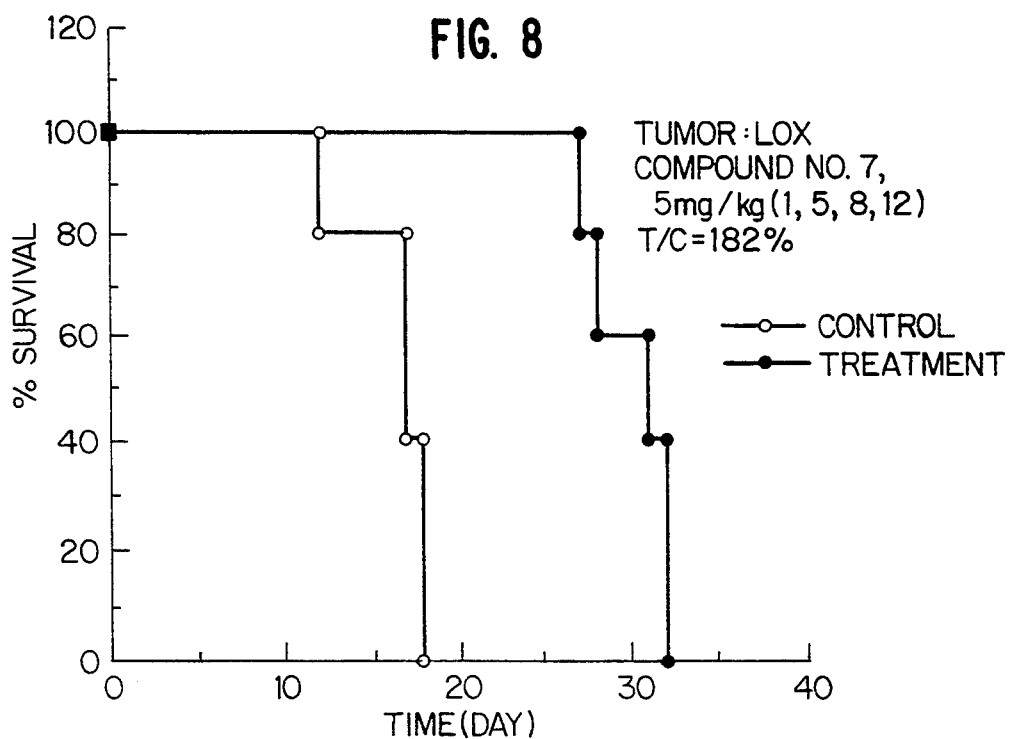

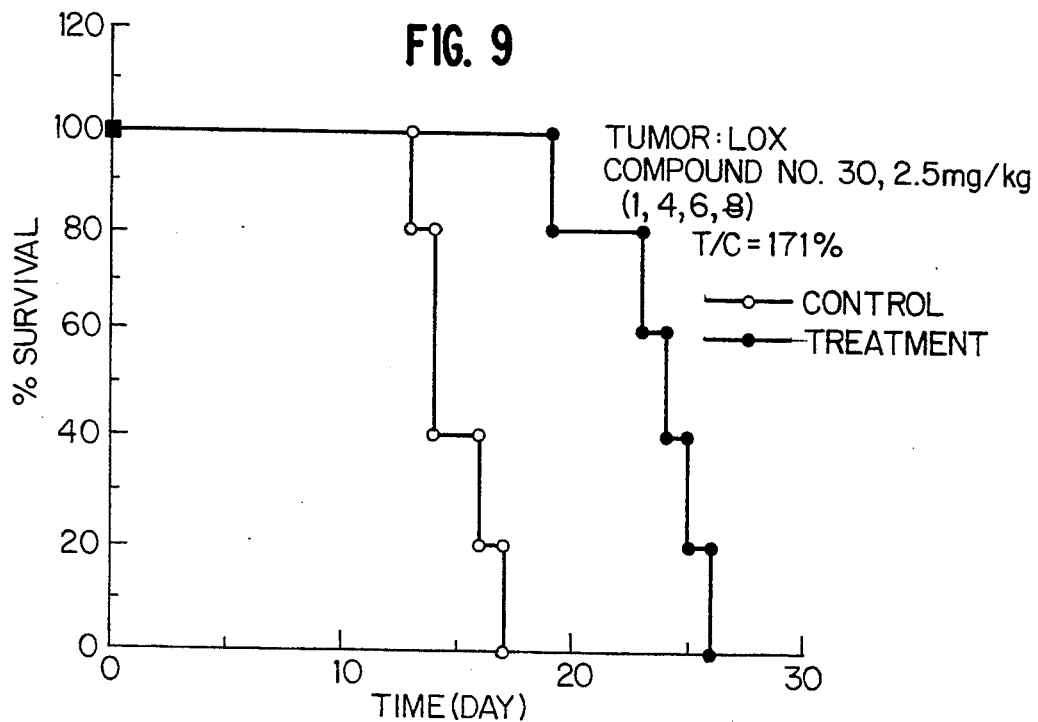
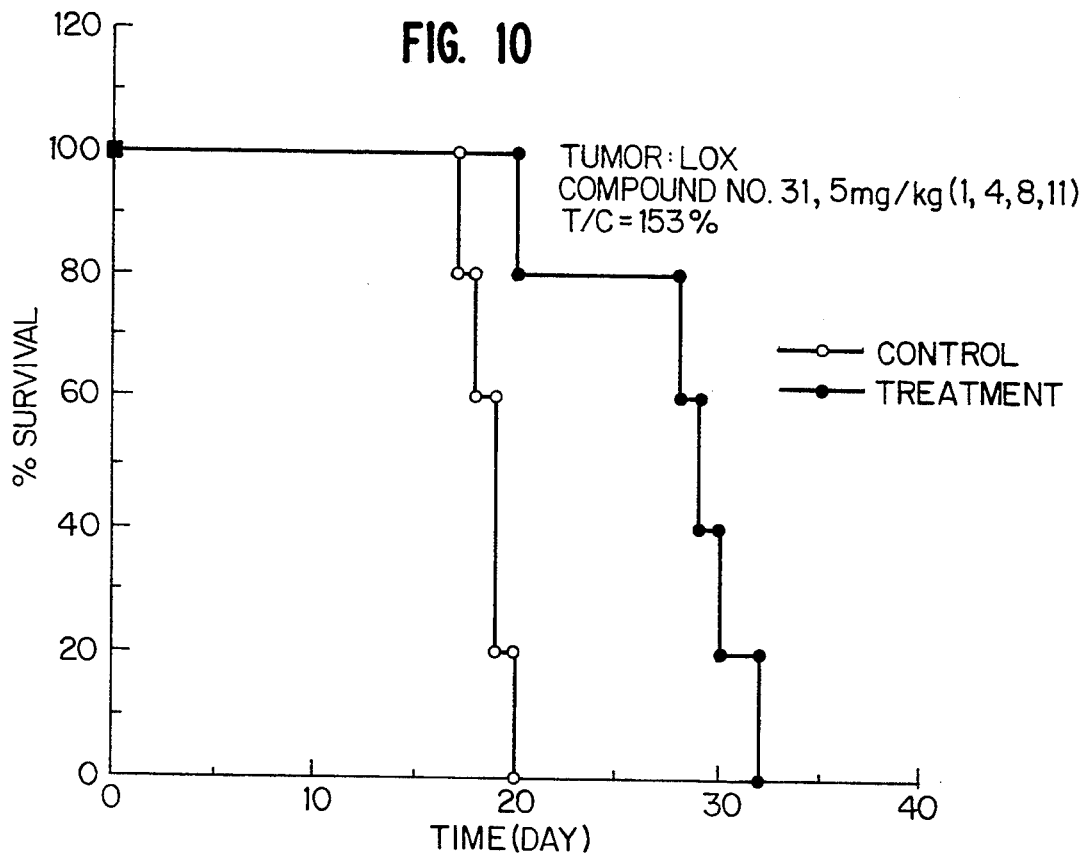

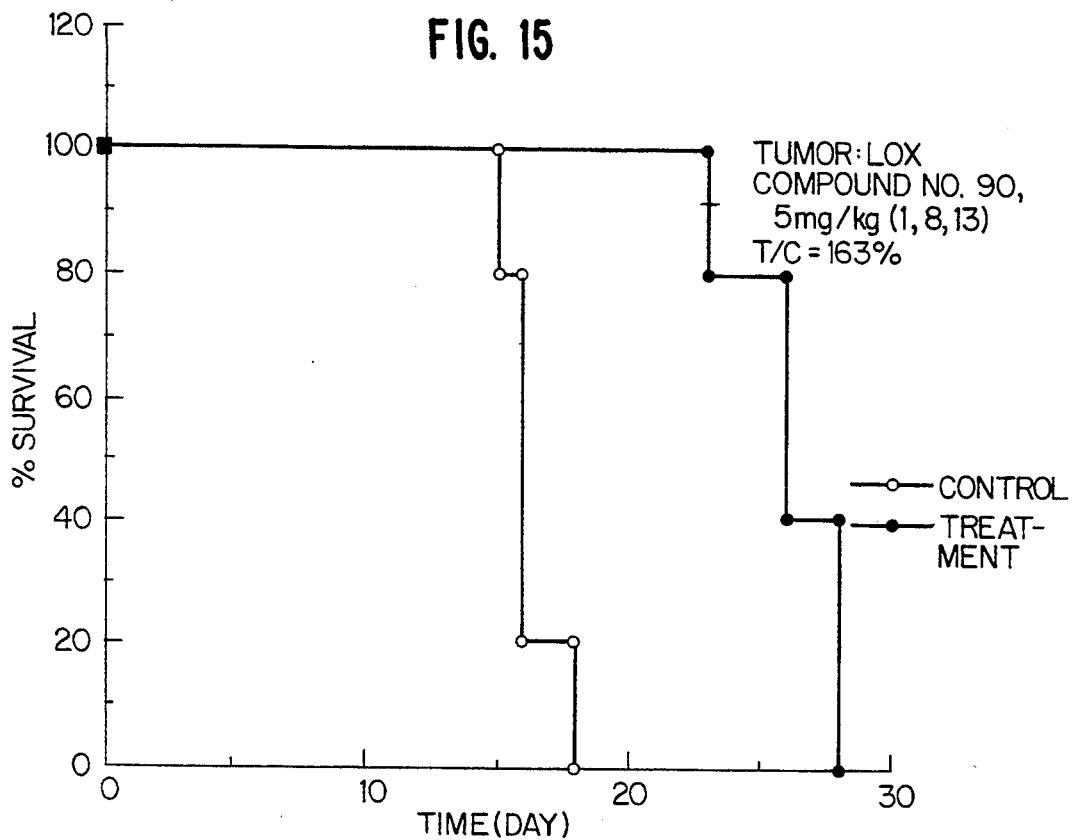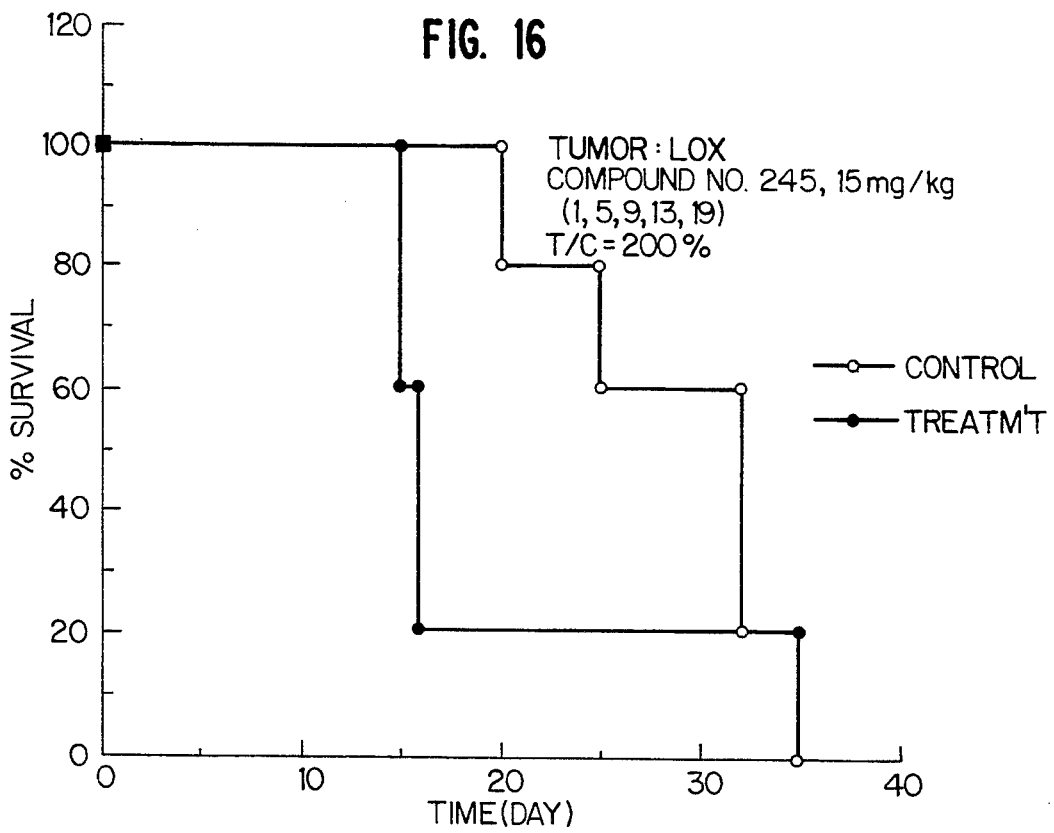

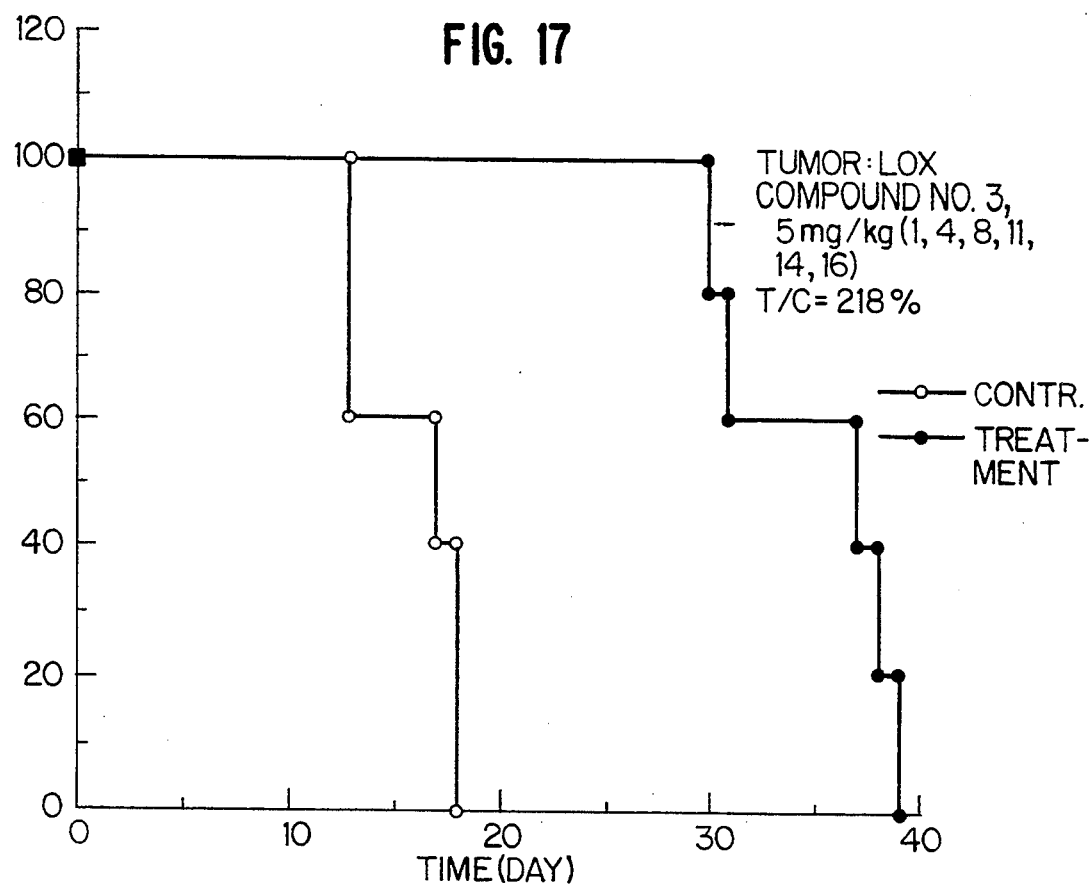
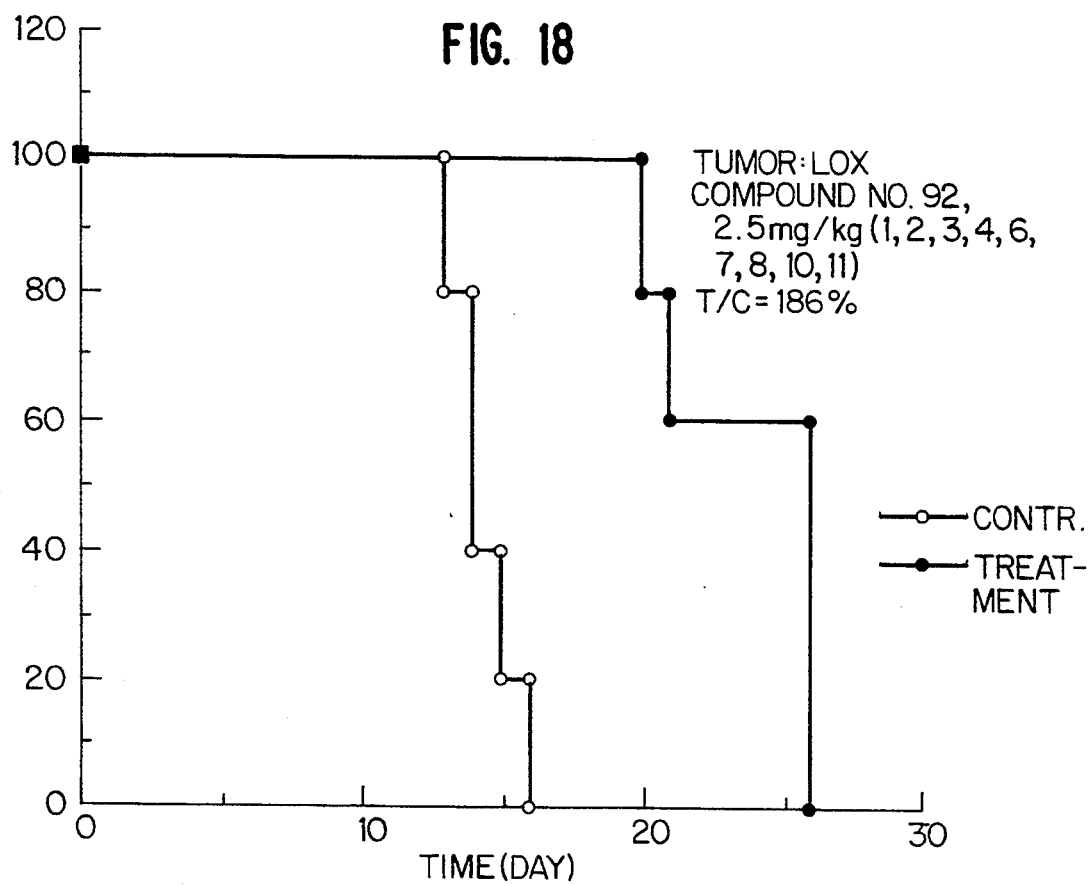

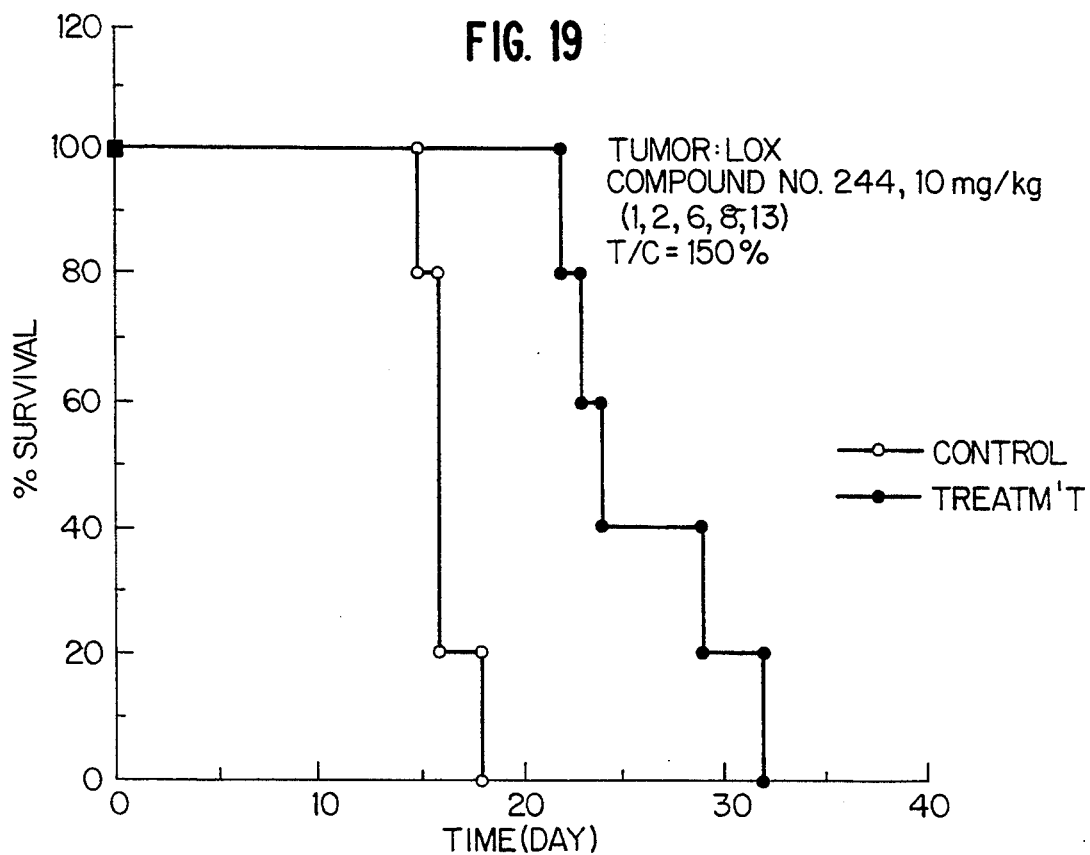
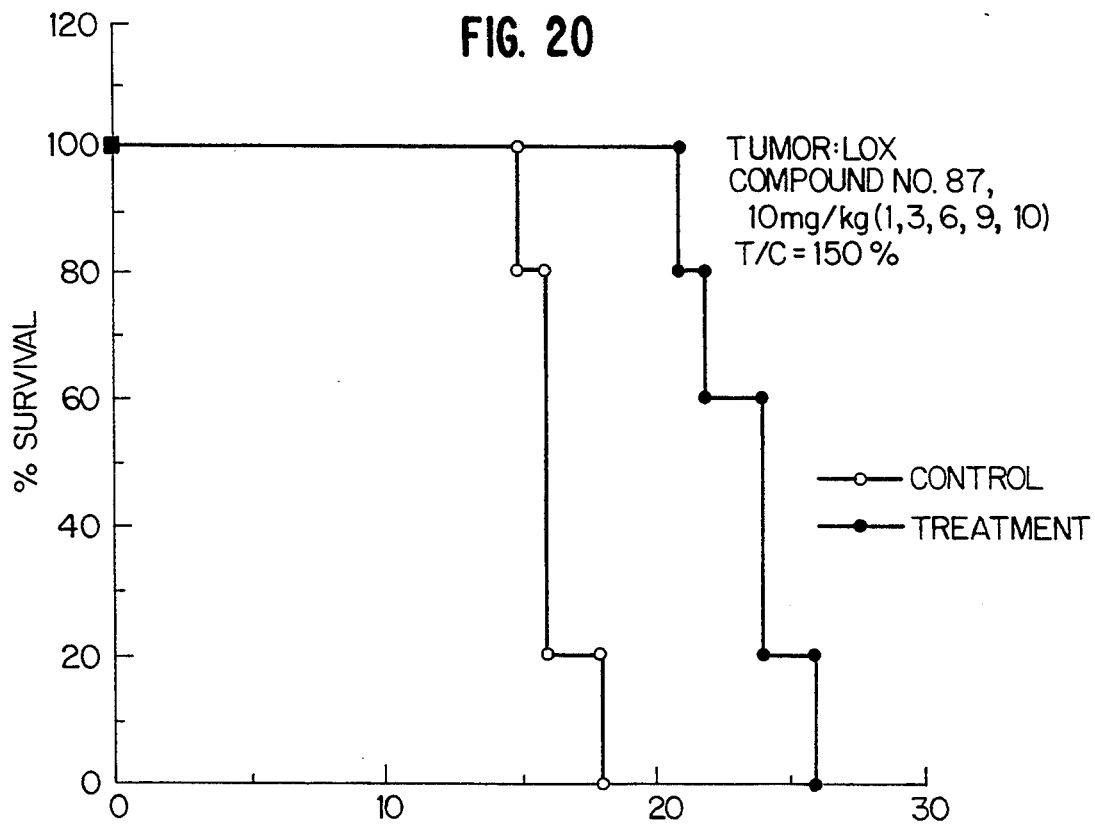

ANTI-HUMAN COLON CARCINOMA CX-1
ACTIVITY OF COMPOUND NO. 13
DAY 1,5,8,12,15,19  20mg/kg

ANTI-HUMAN COLON CARCINOMA CX-1
ACTIVITY OF COMPOUND NO. 39
DAY 1, 5, 8, 11   5mg/kg

COMPOSITION AND METHOD FOR TREATING CANCER

This is a continuation-in-part of application Ser. No. 07/744,130 filed Aug. 13, 1991 and now abandoned.

FIELD OF THE INVENTION

This invention relates to a composition and a method useful in treating a number of different types of cancers, and, in particular, carcinomas or melanomas. More particularly, this invention relates to a pharmaceutical composition containing a select class of rhodacyanine dyes useful in treating cancers and to a method for treating cancers using this composition.

BACKGROUND OF THE INVENTION

Cancer is a serious health problem throughout the world. As a result, an extensive amount of research has been conducted to develop therapies appropriate to the treatment and alleviation of cancer in humans.

In the chemotherapeutic area, research has been conducted to develop anti-tumor agents effective against various types of cancer. Often anti-tumor agents developed and found effective against cancerous cells, unfortunately, are toxic to normal cells. This toxicity gives rise to hair loss, nausea, weight loss, vomiting, hallucination, fatigue, itching, loss of appetite, etc., when administered to a patient needing cancer therapy.

Further, conventionally used chemotherapeutic agents do not have the effectiveness desired or are not as broadly effective against different types of cancers as is desired. As a result, chemotherapeutic agents which have greater effectiveness against cancers and which have a higher degree of selectivity for killing cancer cells with no or minimal effect on normal healthy cells is desired. Highly effective and selective anti-tumor agents, in particular, against cancers of the colon, bladder, prostate, stomach, pancreas, breast, lung, liver, brain, testis, ovary, cervix, skin, vulva, small intestina and like organs is desired. Anti-tumor agents against cancers such as colon cancer and melanomas are also particularly desired because of the lack of any particularly effective therapy at present.

Certain types of cyanine dyes hate been disclosed as having anti-cancer activity (see, for example, Japanese Kokai 79/151,133, 80/31,024, 80/69,513, 80/100,318, Japanese Koho 89/54,325, E.P. No. 28625A2). However, these cyanine dyes cannot be used effectively for therapy in humans because of their high toxicity to healthy cells as well as to cancer cells. In addition, these cyanine dyes often are poorly soluble in diluents acceptable for human administration.

SUMMARY OF THE INVENTION

Accordingly, an object of this invention is to provide anti-tumor agents effective against cancer cells.

A further object of the present invention is to provide anti-tumor agents useful in the treatment of cancer where a higher degree of selectivity against cancer cells exists than has been found for prior art anti-tumor agents.

An even further object of the present invention is to provide anti-tumor agents effective in treatment against carcinomas and melanomas for which prior art treatments have not been found to be particularly effective.

A still further object of this invention is to provide pharmaceutical compositions and a method using the pharmaceutical compositions useful in the treatment and alleviation of cancer in mammals such as humans.

Still another object of the present invention is to provide rhodacyanine dyes which are highly soluble in aqueous diluents suitable for human administration using a pharmaceutically acceptable salt thereof, e.g., using acetate or chloride as a counter ion.

As a result of extensive research, it has not been found that the above-objects of the present invention are satisfied by classes of rhodacyanine dyes, heretofore known primarily for their use in the fabrication of photosensitive materials, which are effective in treating cancer and, in particular carcinomas and melanomas.

In one embodiment, the present invention provides a composition containing (A) a therapeutically effective amount of a rhodacyanine compound selected from the group consisting of compounds of the General Formula (I)

$$Z_1-N(CH=CH)_mC \underset{R_1}{\overset{X_1}{|}} = \underset{O}{\overset{Y_1}{\diagdown}} \underset{N}{\diagup} = L_1 - C = (CH-CH)_n = NZ_2 \overset{X_2}{\underset{R_3}{|}} \quad (I)$$

$$(Q^-)_{l-1}$$

wherein $X_1$ and $X_2$, which may be the same or different, each represents O, S, Se, —CH=CH—, $$\underset{C}{\overset{R_4\diagdown\diagup R_5}{\diagup\diagdown}} \overset{R_6}{\underset{|}{N-}} \text{, or } —N—;$$

$Y_1$ represents O, S, Se, or $$\overset{R_7}{\underset{|}{-N-}};$$

$R_1$ and $R_3$, which may be the same or, different, each represents an alkyl group;

$R_2$ represents an alkyl group, an aryl group or a heterocyclic group;

$Z_1$ and $Z_2$, which may be the same or different, each represents an atomic group necessary to form a 5- or 6-membered ring;

$L_1$ represents a methine group and $L_1$ and $R_3$ may combine and form a 5- or 6-membered ring;

$R_4$ and $R_5$, which may be the same or different, each represents an alkyl group;

$R_6$ and $R_7$, which may be the same or different, each represents an alkyl group or an aryl group;

Q represents a pharmaceutically acceptable anion;

l represents 1 or 2;

m and n, which may be the same or different, each represents 0 or 1; and (B) a pharmaceutically acceptable carrier or diluent.

In another embodiment, the present invention provides a method of treatment of cancer comprising administering the composition described above to a mammalian host in need of such treatment.

Preferred embodiments of this invention include compositions and method as described above where the rhodacyanine compound is a compound selected from the group consisting of compounds of the General Formula (II) to (V) set forth below:

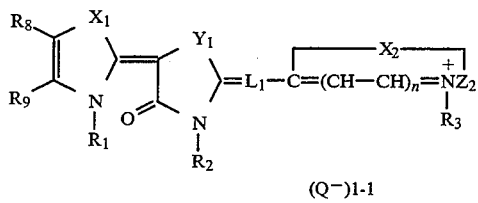

(Q⁻)$_{l-1}$ wherein
$Z_2$, $Y_1$, $X_1$, $X_2$, $R_1$, $R_2$, $R_3$, $L_1$, Q, l and n all have the same meanings as defined above;

$R_8$ and $R_9$, which may be the same or different, each represents a hydrogen atom, an alkyl group or an aryl group, or $R_8$ and $R_9$ may combine and form a fused 5- or 6-membered ring;

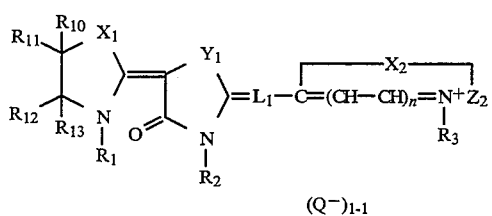

(Q⁻)$_{l-1}$ wherein
$X_1$, $Y_1$, $X_2$, $Z_2$, $R_1$, $R_2$, $R_3$, Q, l, $L_1$ and n have the same meanings as defined above;

$R_{10}$, $R_{11}$, $R_{12}$ and $R_{13}$, which may be the same or different, each represents a hydrogen atom, an alkyl group or an aryl group, or any two of $R_{10}$ to $R_{13}$ may combine and form a 5- or 6-membered ring;

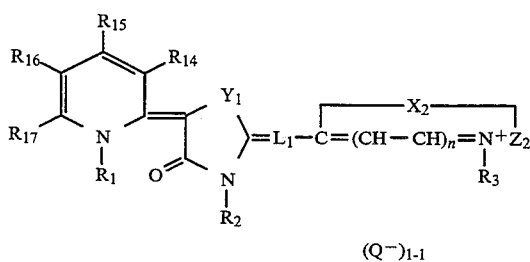

(Q⁻)$_{l-1}$

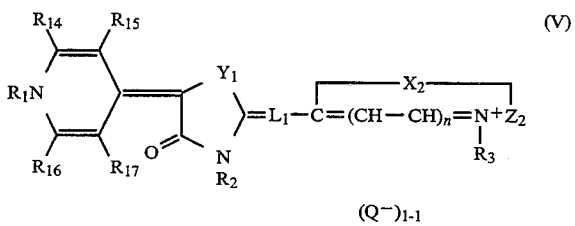

(Q⁻)$_{l-1}$ wherein
$Y_1$, $X_2$, $Z_2$, $R_1$, $R_2$, $R_3$, Q, l, $L_1$ and n have the same meanings as define above;

$R_{14}$, $R_{15}$, $R_{16}$, and $R_{17}$, which may be the same or different, each represents a hydrogen atom, an alkyl group, an aryl group, an alkoxy group, an aryloxy group, an acyl group, an alkoxycarbonyl group, a benzoyl group, an ureido group, an amino group, an amido group, an sulfamido group, a carbomoyl group, a sulfamoyl group, a halogen atom, a nitro group, a cyano group, a hydroxy group or a carboxyl group, or any adjacent two of $R_{14}$, to $R_{17}$ may combine and form a 5- or 6-membered ring.

Among the compounds having the general formula (II), further preferred are those compounds represented by the following formulae (IIA) and (IIB).

Formula (IIA):

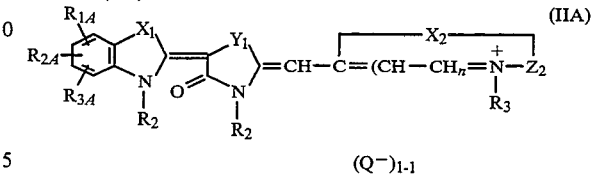

(Q⁻)$_{l-1}$ wherein
$X_2$ represents O, S, Se, —CH=CH— or —CR$_4$R$_5$—;

$R_1$ and $R_3$, which may be the same or different, each represents an alkyl group having 1 to 8 carbon atoms;

$R_2$ represents an alkyl group having 1 to 8 carbon atoms or an aryl group having 6 to 8 carbon atoms;

$R_{1A}$, $R_{2A}$ and $R_{3A}$, which may be the same or different, each represents a hydrogen atom, a halogen atom, a hydroxy group, an alkyl group, an aryl group, an alkoxy group, an aryloxy group or an alkoxycarbonyl group;

$Z_2$ represents an atomic group necessary to form a 5- or 6-membered ring; and $X_1$, $Y_1$, $R_4$, $R_5$, Q, k, and n have the same meanings as defined above.

Formula (IIB):

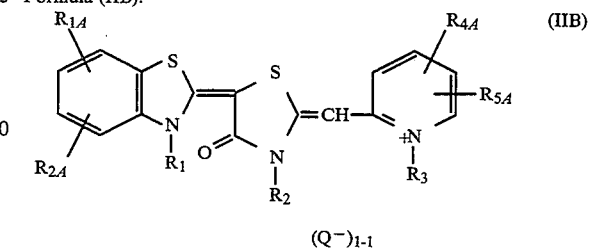

(Q⁻)$_{l-1}$ wherein
$R_1$ and $R_3$, which may be the same or different, each represents an alkyl group having 1 to 8 carbon atoms;

$R_2$ represents an alkyl group having 1 to 8 carbon atoms or an aryl group having 6 to 8 carbon atoms;

$R_{1A}$ and $R_{2A}$, which may be the same or different, each represents a hydrogen atom, a halogen atom, a hydroxy group, an alkyl group having 1 to 5 carbon atoms, an alkoxy group having 1 to 5 carbon atoms, a phenyl group, a phenoxy group or an alkoxycarbonyl group having 2 to 6 carbon atoms;

$R_{4A}$ and $R_{5A}$, which may be the same or different, each represents a chlorine atom, an alkyl group having 1 to 5 carbon atoms or a methoxycarbonyl group; and Q and k have the same meanings as defined above.

Among the compounds having the general formula further preferred are those compounds represented by the following formulae (IVA) and (IVB).

Formula (IVA):

-continued

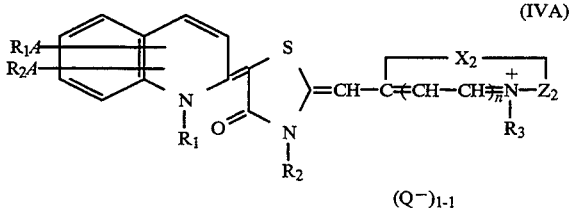

(IVA)

$(Q^-)_{1-1}$ wherein $X_2$ represents O, S, Se or —CH=CH—;

$R_1$ and $R_3$, which may be the same or different, each represents an alkyl group having 1 to 8 carbon atoms;

$R_2$ represents an alkyl group having 1 to 8 carbon atoms or an aryl group having 6 to 8 carbon atoms;

$R_{1A}$ and $R_{2A}$, which may be the same or different, each represents a hydrogen atom, a halogen atom, a hydroxy group, an alkyl group, an aryl group, an alkoxy group, an aryloxy group or an alkoxycarbonyl group;

$Z_2$ represents an atomic group necessary to form a ring of thiazole, benzothiazole, naphthothiazole, benzoxazole, naphthoxazole, benzoselenazole, thiazoline, 2-pyridine, 4-pyridine, 2-quinoline, or 4-quinoline; and Q, k and n have the same meanings as defined above.

Formula (IVB):

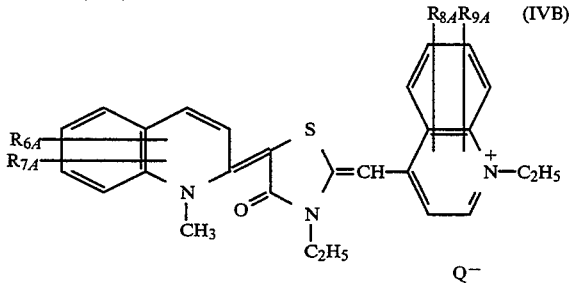

(IVB)

wherein $R_{6A}$, $R_{7A}$, $R_{8A}$ and $R_{9A}$ each represents a hydrogen atom, chlorine atom, ethoxy group, hydroxy group, methyl group, dimethylcarbamoyl group, or acetylamino group and Q has the same meanings as defined above.

In the specific embodiments of the present invention, the pharmaceutical compositions of the present invention comprise, as an anti-tumor agent, a compound selected from the group consisting of the compounds having the general formulae (I) to (V), together with a suitable pharmacologically acceptable carrier or a diluent.

BRIEF DESCRIPTION OF THE ACCOMPANYING DRAWINGS

Figure 6:
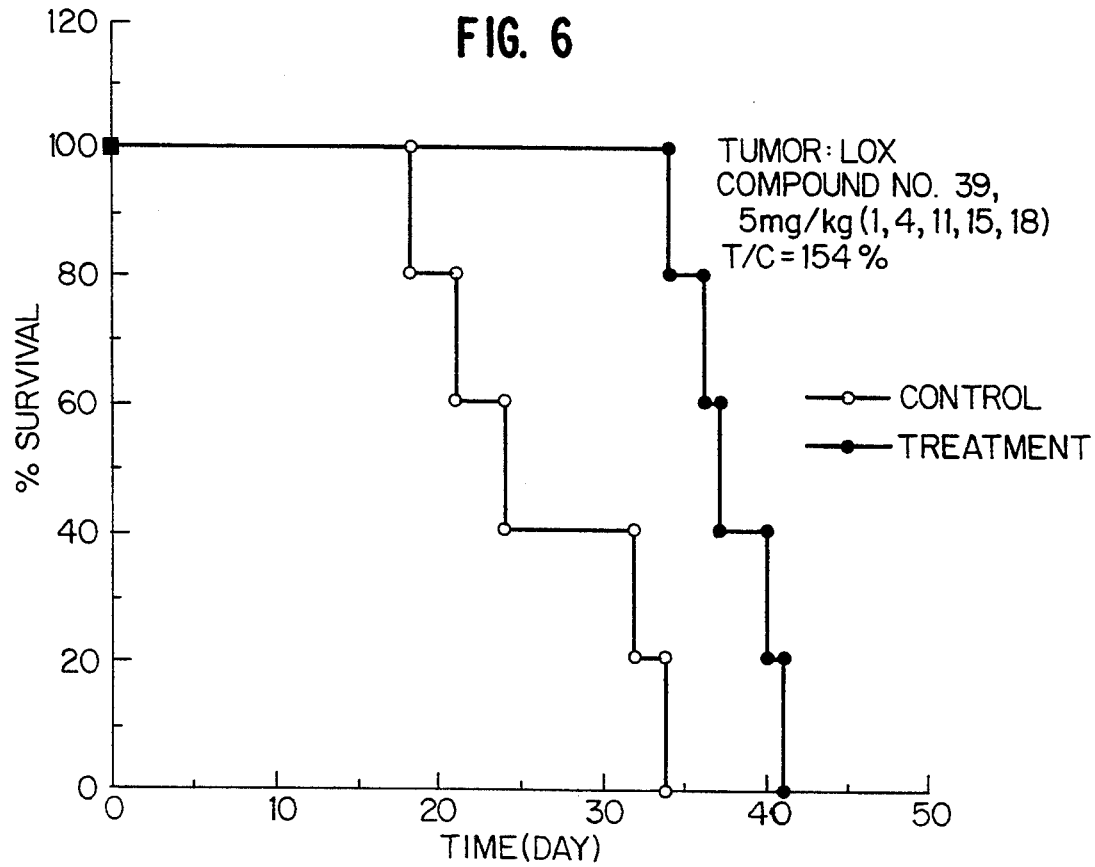
Figure 11:
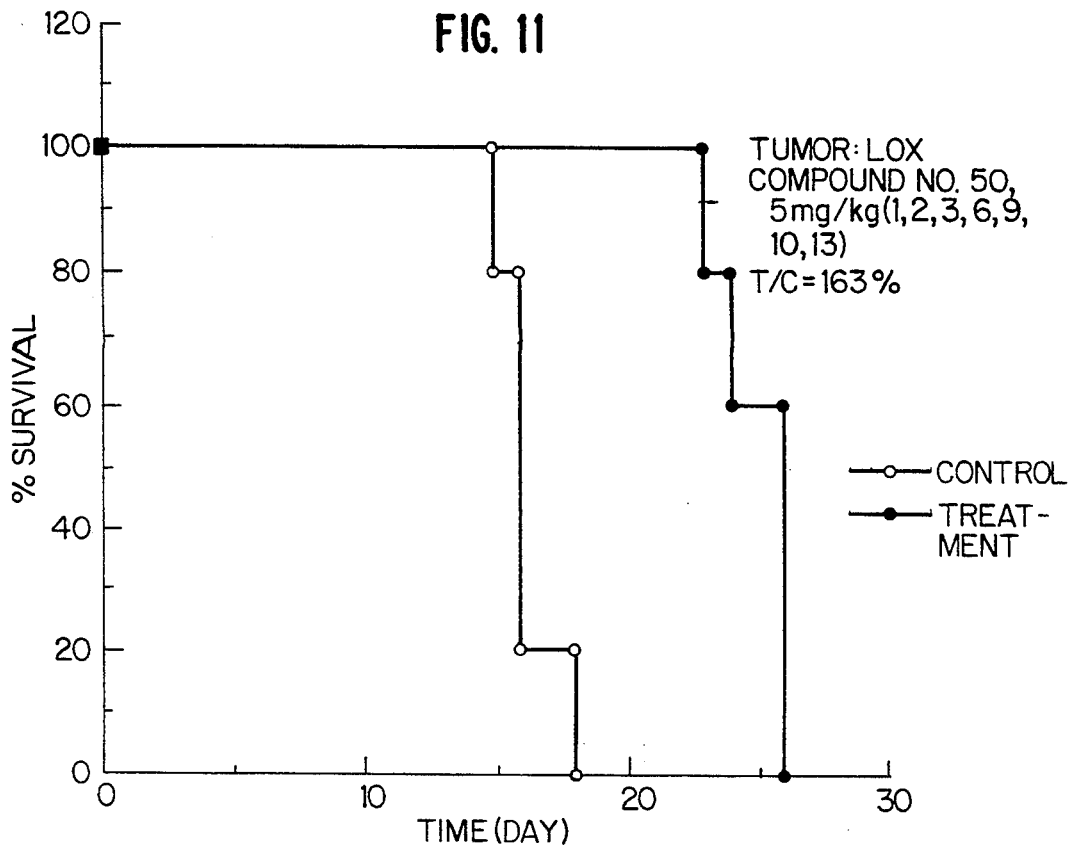
Figure 12:
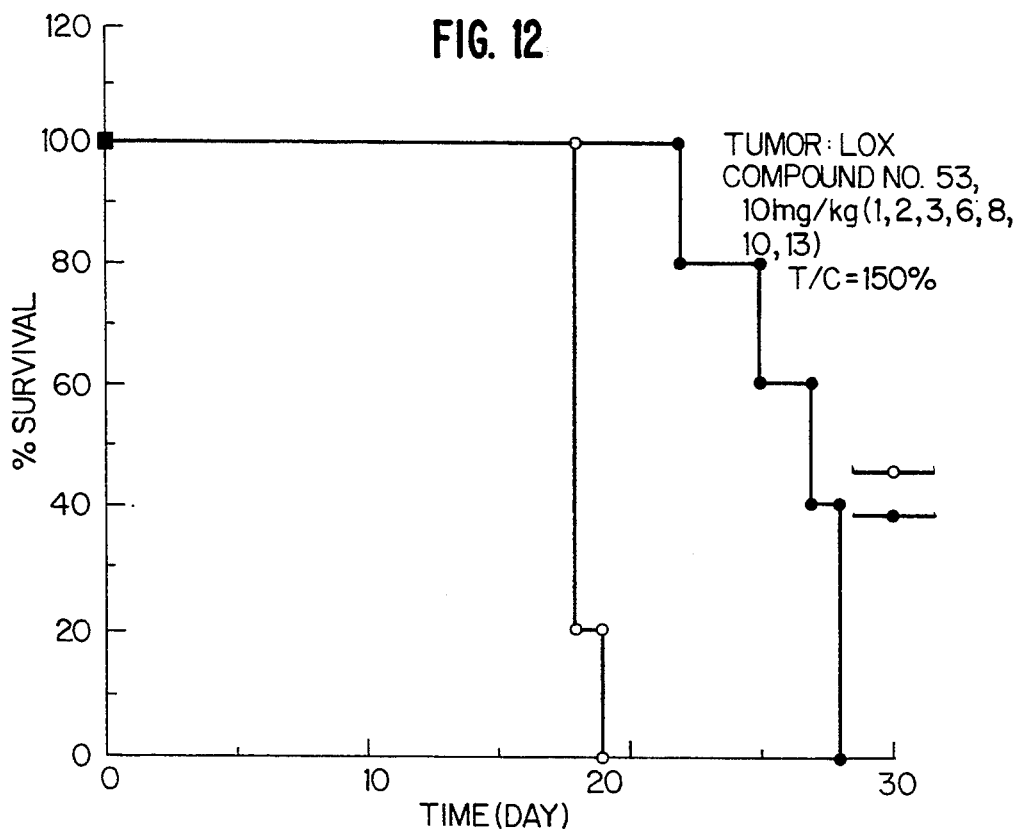
Figure 13:
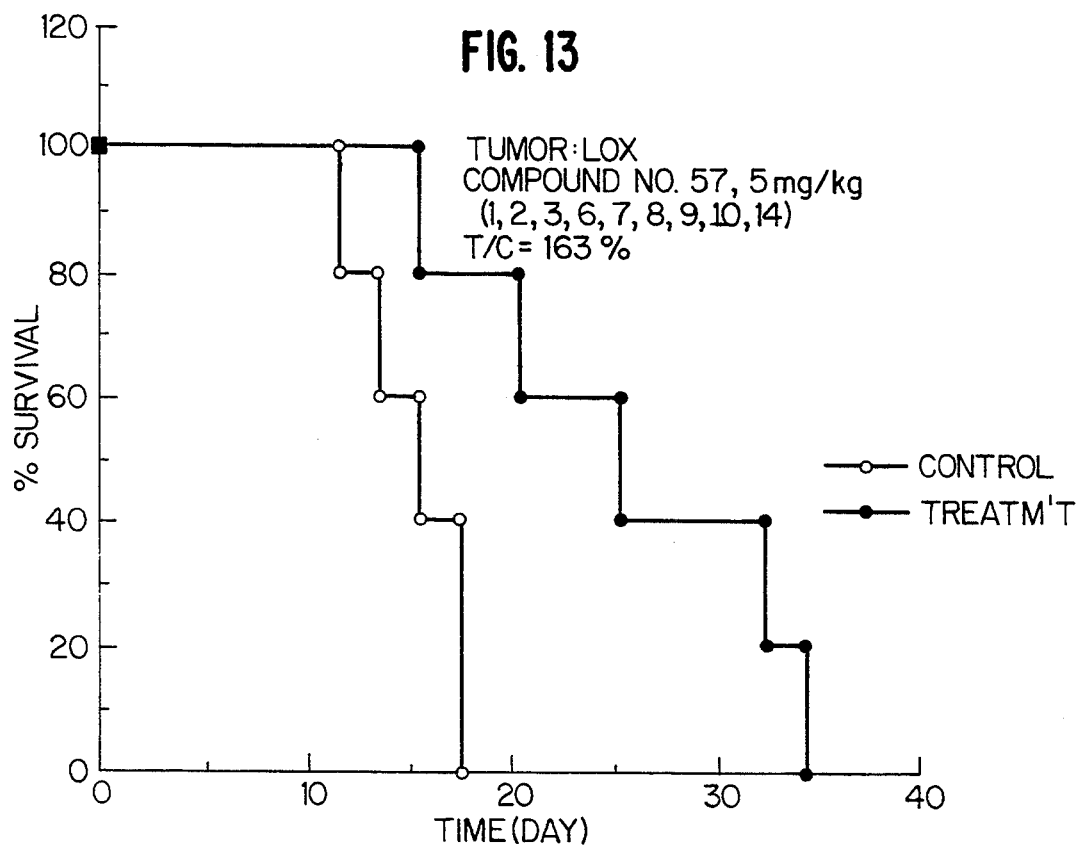
Figure 14:
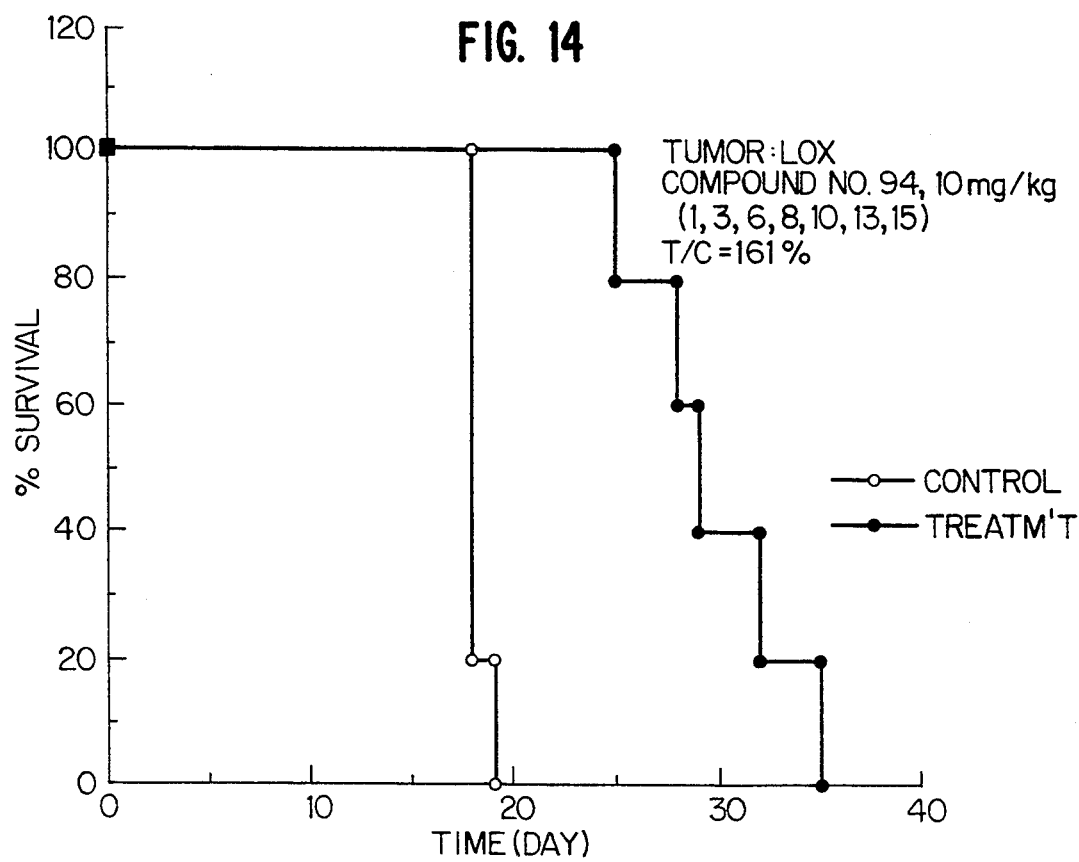
Figure 21:
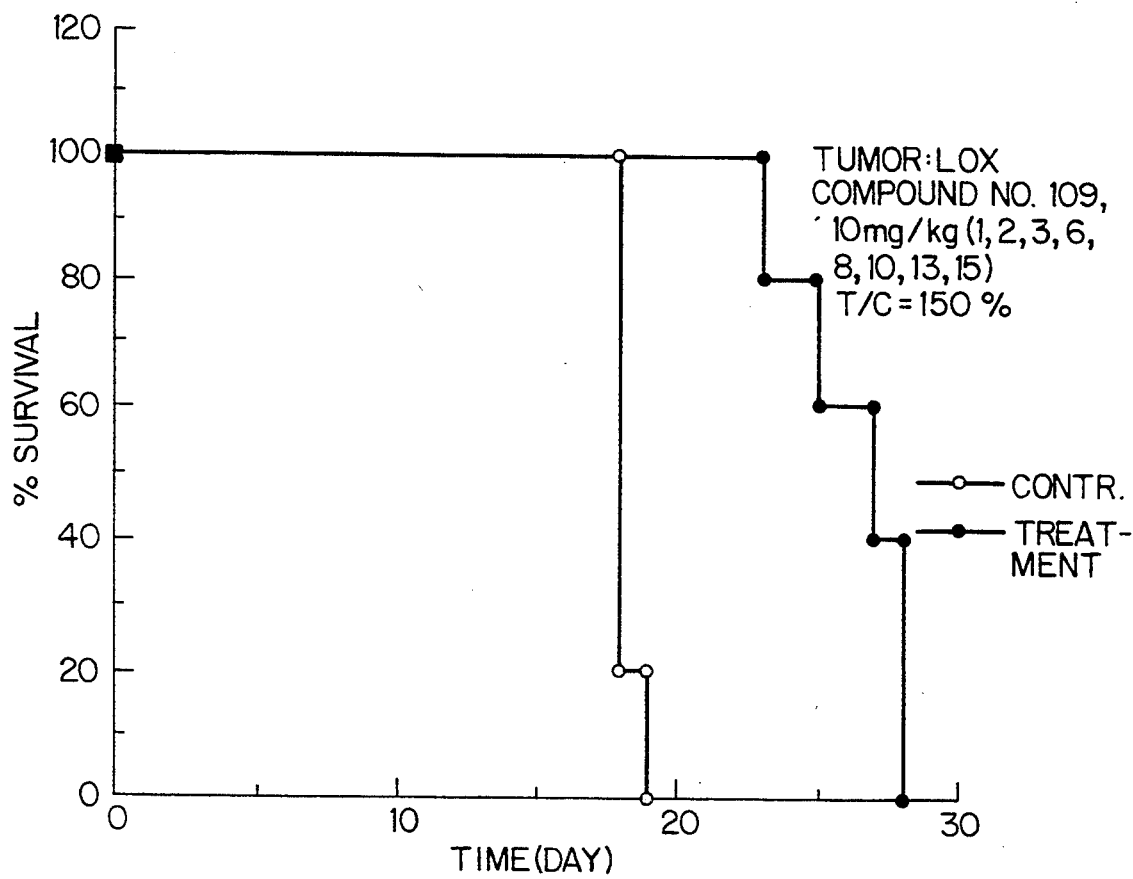
Figure 22:
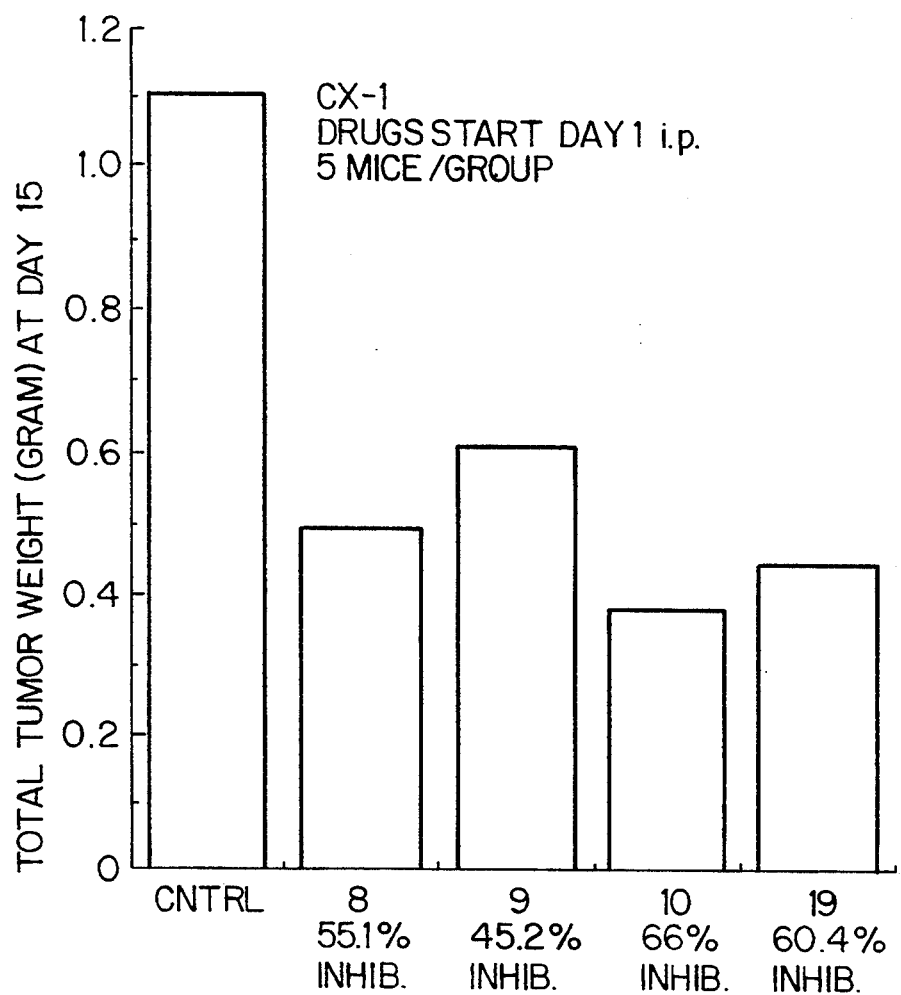
Figure 23:
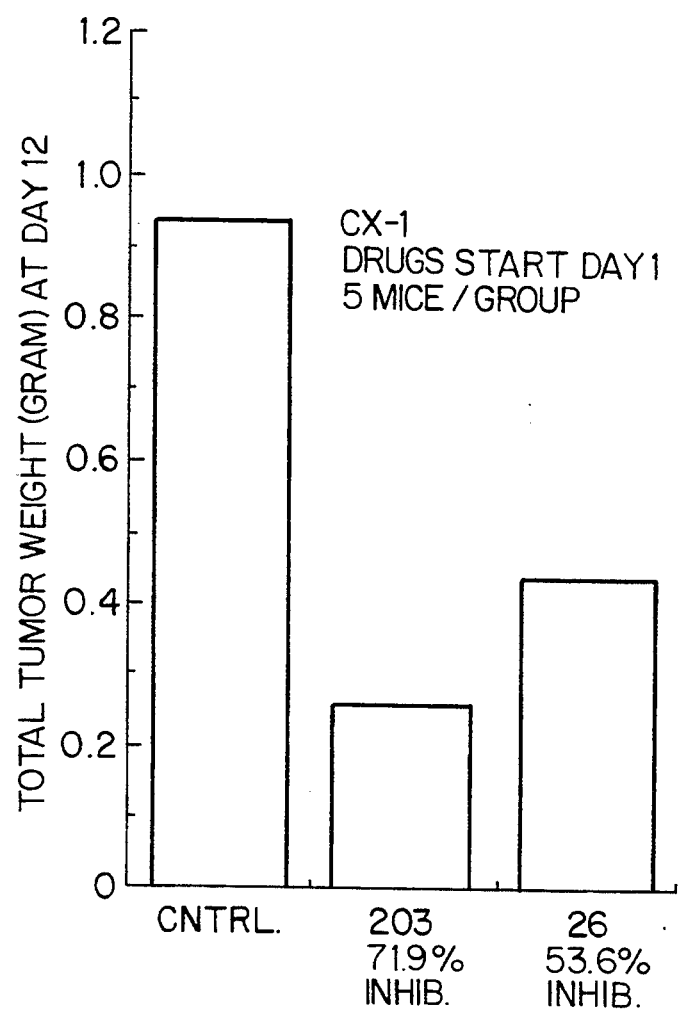
Figure 24:
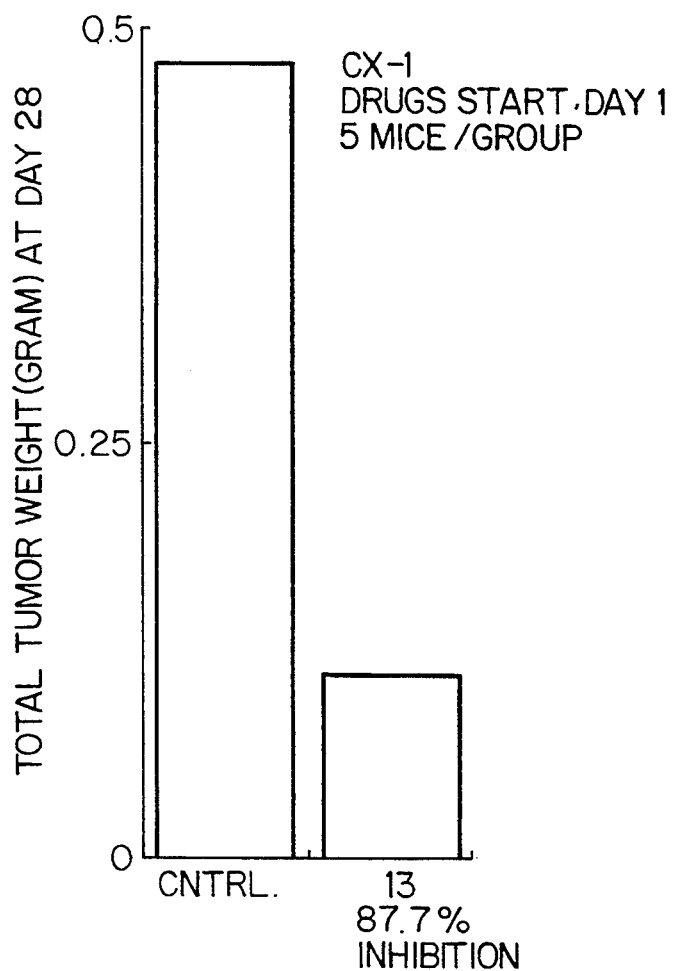
Figure 25:
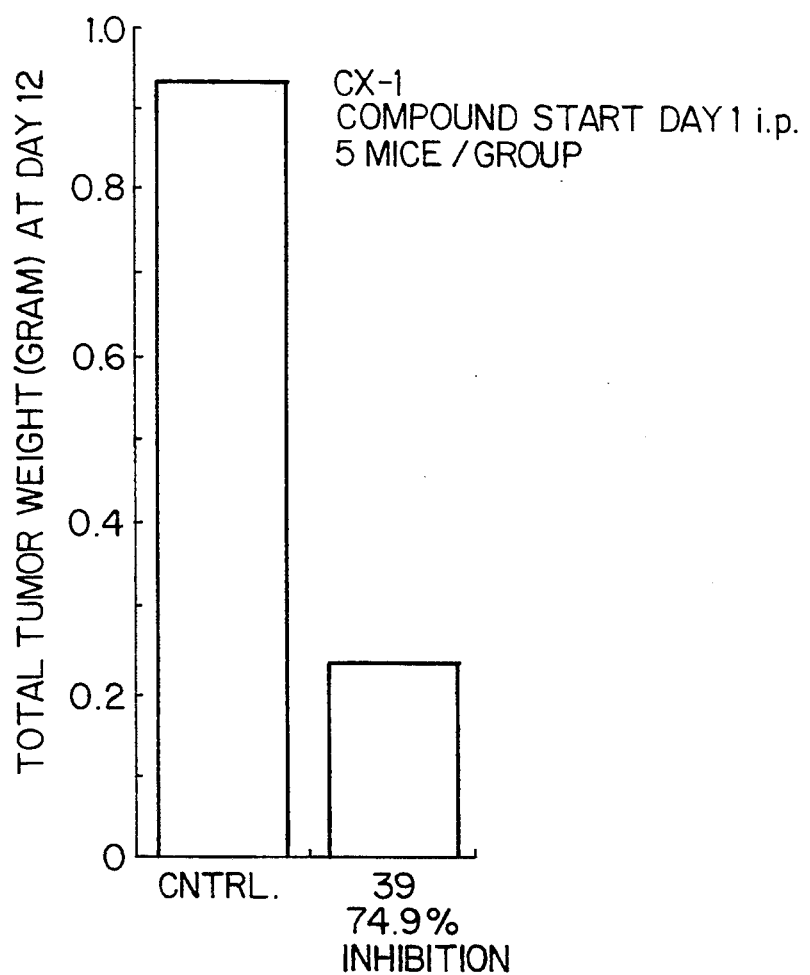

FIGS. 1 to 25 are graphical presentations of the results obtained in the Examples described hereinafter.

DETAILED DESCRIPTION OF THE INVENTION

The embodiments of this invention include compounds selected from the group consisting of compounds represented by the General Formulas (I) to (V) above as an anti-cancer agent, along with a suitable pharmaceutically acceptable carrier or diluent.

In greater detail, in the General Formulas (I) to (V) $X_1$ and $X_2$, individually, represents an oxygen atom, a sulfur atom, a selenium atom,

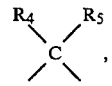

—CH=CH— or a group of the formula >N—$R_6$ where $R_4$ and $R_5$ each represents an alkyl, i.e., an unsubstituted or substituted alkyl group such as a straight-chain, branched chain or cyclic alkyl group, and $R_6$ is an alkyl, i.e., an unsubstituted or substituted alkyl group such as a straight-chain, branched chain or cyclic alkyl group, an aryl, i.e. an unsubstituted or substituted aryl group such as a monocyclic or bicyclic aryl group, or a heterocyclic, i.e., an unsubstituted or substituted heterocyclic group such as a 5- to 6-membered heterocyclic group which can be saturated or unsaturated and can contain one or more nitrogen atoms, oxygen atoms and sulfur atoms.

$Y_1$ represents an oxygen atom, a sulfur atom, a selenium atom or a group of the formula

where $R_7$ is an alkyl, i.e., an unsubstituted or substituted alkyl group such as a straight-chain, branched chain or cyclic alkyl group, an aryl, i.e., an unsubstituted or substituted aryl group such as a monocyclic or bicyclic aryl group, or a heterocyclic group, i.e., an unsubstituted or substituted heterocyclic group such as a 5- to 6-membered heterocyclic group which can be saturated or unsaturated and can contain one or more nitrogen atoms, oxygen atoms and sulfur atoms.

$R_1$, $R_2$ and $R_3$ each individually represents an alkyl, i.e., an unsubstituted or substituted alkyl group such as a straight-chain, branched chain or cyclic alkyl group and $R_2$ can additionally be an aryl, i.e., an unsubstituted or substituted aryl group such as a monocyclic, bicyclic or tricyclic aryl group or a heterocyclic, i.e., an unsubstituted or substituted heterocyclic group such as a 5- to 6-membered heterocyclic group which can be saturated or unsaturated and can contain one or more nitrogen atoms, oxygen atoms and sulfur atoms as hetero atoms.

$Z_1$ and $Z_2$, which may be the same or different, each represents an atomic group necessary to form a saturated or unsaturated 5- or 6-membered ring which may contain one or more nitrogen atoms, oxygen atoms, sulfur atoms or selenium atoms as hetero atoms and $Z_1$ may be substituted or condensed with another ring such as a saturated or unsaturated ring.

$L_1$ represents a methine group, i.e., an unsubstituted or substituted methine group and when $L_1$ is a substituted methine group, $L_1$ and $R_3$ may combine to form a saturated or unsaturated 5- or 6-membered ring.

$R_8$ and $R_9$ each represents a hydrogen atom or an alkyl, i.e., an unsubstituted or substituted alkyl group such as a straight-chain, branched chain or cyclic alkyl group and moreover, $R_8$ and $R_9$ represents an aryl, i.e., an unsubstituted or substituted aryl group such as a monocyclic, bicyclic or tricyclic aryl group or $R_8$ and $R_9$ may combine and form a saturated or unsaturated fused 5- or 6-membered ring which may be substituted.

$R_{10}$, $R_{11}$, $R_{12}$ and $R_{13}$ each represents a hydrogen atom or an alkyl, i.e. an unsubstituted or substituted alkyl group such as a straight-chain, branched chain or cyclic alkyl group and moreover, $R_{10}$, $R_{11}$, $R_{12}$ and $R_{13}$ represents an aryl, i.e., an unsubstituted or substituted aryl group such as a monocyclic, bicyclic or tricyclic aryl group.

Further, any two of $R_{10}$, $R_{11}$, $R_{12}$ and $R_{13}$ may combine and form an unsubstituted or substituted 5- or 6-membered ring. Preferred are carbocyclic rings.

$R_{14}$, $R_{15}$, $R_{16}$ and $R_{17}$ each represents a hydrogen atom or an alkyl group, i.e., an unsubstituted or substituted alkyl group such as a straight-chain, branched chain or cyclic alkyl group and moreover, $R_{14}$, $R_{15}$, $R_{16}$ and $R_{17}$ each represents an aryl, i.e., an unsubstituted or substituted aryl group such as a monocyclic or bicyclic aryl group.

Further, $R_{14}$, $R_{15}$, $R_{16}$ and $R_{17}$ each represents an unsubstituted or substituted alkoxy group, for example, an alkoxyl group where the alkyl moiety thereof is a straight-chain or branched chain alkyl moiety; an unsubstituted or substituted aryloxy group, for example, an aryloxy group where the aryl moiety thereof is monocyclic or bicyclic; an unsubstituted or substituted acyl group, for example, an alkylacyl group where the alkyl moiety thereof is a straight-chain or branched chain alkyl moiety or an arylacyl group where the aryl moiety thereof is monocyclic or bicyclic; an unsubstituted or substituted alkoxycarbonyl group, for example, an alkoxycarbonyl group where the alkyl moiety thereof is a straight-chain or branched chain alkyl moiety; an unsubstituted or substituted benzoyl group; an unsubstituted or substituted ureido group, for example, an alkylureido group where the alkyl moiety thereof is a straight-chain or branched chain alkyl moiety or an arylureido group where the aryl moiety thereof is monocyclic or bicyclic; an unsubstituted or substituted amino group, for example, a mono- or di-alkylamino group where the alkyl moiety thereof is a straight-chain or branched chain alkyl moiety or a mono- or di-arylamino group where the aryl moiety thereof is a monocyclic or bicyclic; an unsubstituted or substituted amido group, for example, a mono- or di-alkylamido group where the alkyl moiety thereof is a straight-chain or branched chain alkyl moiety or a mono- or di-arylamido group where the aryl moiety thereof is monocyclic or bicyclic; an unsubstituted or substituted sulfamido group, for example, an alkylsulfamido group where the alkyl moiety thereof is a straight chain or branched chain alkyl moiety or an arylsulfamido group where the aryl moiety thereof is monocyclic or bicyclic; an unsubstituted or substituted carbamyl group, for example, an alkylcarbamyl group where the alkyl moiety thereof is a straight chain or branched chain alkyl moiety or an arylcarbamyl group where the aryl moiety thereof is monocyclic or bicyclic; an unsubstituted or substituted sulfamoyl group, for example, an alkylsulfamoyl group where the alkyl moiety thereof is a straight chain or branched chain alkyl moiety or an arylsulfamoyl group where the aryl moiety thereof is monocyclic or bicyclic; a halogen atom such as a bromine atom, a chlorine atom, an iodine atom or a fluorine atom; a nitro group; a cyano group; a hydroxy group; or a carboxy group, or any adjacent two of $R_{14}$ to $R_{17}$ may combine and form a saturated or unsaturated 5- or 6-membered ring which may have other rings fused therewith.

Q represents a pharmaceutically acceptable anion necessary for electrical charge balance, l is 1 or 2 and m and n each is 0 or 1.

More-specifically, as described above, $R_1$ and $R_3$ individually can represent an alkyl group which may be unsubstituted or substituted. Suitable examples of alkyl groups include straight-chain, branched chain and cyclic alkyl groups having 1 to 15 carbon atoms, more preferably 1 to 10 carbon atoms, even more preferably 1 to 8 carbon atoms. Specific examples of alkyl groups for $R_1$ and $R_3$ include methyl, ethyl, n-propyl, i-propyl, n-butyl, i-butyl, sec-butyl, tert-butyl, n-pentyl, hexyl, heptyl, octyl, cyclopropyl, cyclopentyl, cyclohexyl, 2-propenyl, 2-butenyl, 3-hexenyl and the like. Specific examples of suitable substituents which can be present on the alkyl group when $R_1$ and $R_3$ represent a substituted alkyl group include halogen atoms such as chlorine, bromine, fluorine and iodine, e.g. trifluoromethyl, tetrafluoropropyl and pentafluoropropyl, aryl group, an alkoxy group, a hydroxy group, and the like. A preferred number of carbon atoms for the unsubstituted and substituted alkyl groups for $R_1$ and $R_3$ ranges from 1 to 15, more preferably 1 to 10, most preferably 1 to 8.

As defined above, $R_2$, $R_6$ and $R_7$ represents an alkyl group which can be a straight-chain, branched chain or cyclic alkyl group and which may be substituted. Suitable examples of alkyl groups and substituents thereon are as described above for $R_1$ and $R_3$. A preferred number of carbon atoms for the alkyl group represented by $R_2$, $R_6$ and $R_7$ is from 1 to 15 carbon atoms, more preferably 1 to 10 carbon atoms, most preferable is 1 to 8 carbon atoms.

The aryl group represented by $R_2$, $R_6$ and $R_7$ above can be a monocyclic, bicyclic or tricyclic aryl group such as a phenyl group, a biphenyl group, a naphthyl group or an anthracenyl group and such may be unsubstituted or substituted. Suitable examples of substituents which can be present on the aryl group represented by $R_2$, $R_6$ and $R_7$ include one or more of a halogen atom such as chlorine, bromine, fluorine or iodine, an alkyl group, an alkoxy group, a hydroxy group, a nitro group, a cyano group, an amino group, an alkyl- or aryl-substituted amino group, an acylamino group, a sulfonylamino group, a carbamoyl group, a sulfamoyl group, a carboxyl group, an alkoxycarbonyl group, and the like. A suitable number of carbon atoms for the aryl group for $R_2$, $R_6$ and $R_7$ is 6 to 20, preferably 6 to 15, more preferably 6 to 8.

The heterocyclic ring represented by $R_2$, $R_6$ and $R_7$ can be a 5- to 6-membered heterocyclic ring containing one or more oxygen atoms, sulfur atoms or nitrogen atoms as hetero atoms. Suitable examples of heterocyclic rings represented by $R_2$, $R_6$ and $R_7$ include an imidazole ring, a thiazole ring, a pyrrole ring, a pyrazole ring, a furan ring, a thiophene ring, a piperidine ring, a morpholine ring, a piperadine ring, a pyrazine ring, a pyridine ring, a pyrimidine ring, and the like. These heterocyclic rings may be substituted, for example, by substituents as described above for the aryl group for $R_2$, $R_6$ and $R_7$ or may be condensed with another ring such as saturated or unsaturated ring.

Examples of alkyl groups represented by $R_4$ and $R_5$ include unsubstituted or substituted alkyl groups having from 1 to 15 carbon atoms, more preferably 1 to 10 carbon atoms. Suitable examples of suitable alkyl groups include those described above for $R_1$ and $R_3$ and substituents which can be present on the alkyl group represented by $R_4$ and $R_5$ include an alkyl group, an alkoxy group, a hydroxy group, a cyano group, a halogen atom, and the like.

Examples of alkyl groups represented by $R_6$ and $R_7$ above include alkyl groups as described above for $R_4$ and $R_5$. A suitable number of carbon atoms for the alkyl group for $R_6$ and $R_7$ is 1 to 15 carbon atoms, more preferably 1 to 10 carbon atoms. Further, $R_6$ and $R_7$ represents an unsubstituted or substituted aryl group which includes monocyclic, bicyclic and tricyclic aryl groups. A suitable number of carbon atoms for the aryl group for $R_6$ and $R_7$ is 6 to 20 carbon atoms, more preferably 6 to 15 carbon atoms. Specific examples of suitable aryl groups for $R_6$ and $R_7$ and substituents therefore include those described above for $R_2$.

The alkyl group represented by $R_8$, $R_9$, $R_{10}$, $R_{11}$, $R_{12}$, $R_{13}$, $R_{14}$, $R_{15}$, $R_{16}$ and $R_{17}$ above can be straight-chain, branched chain or cyclic and can include 1 to 15 carbon atoms, more preferably 1 to 10 carbon atoms, even more preferably 1 to 8 carbon atoms. The alkyl group represented by $R_8$, $R_9$, $R_{10}$, $R_{11}$, $R_{12}$, $R_{13}$, $R_{14}$, $R_{15}$, $R_{16}$ and $R_{17}$ can also be a unsubstituted alkyl group. Specific examples of alkyl group for $R_8$, $R_9$, $R_{10}$, $R_{11}$, $R_{12}$, $R_{13}$, $R_{14}$, $R_{15}$, $R_{16}$ and $R_{17}$ include methyl, ethyl, n-propyl, i-propyl, 2-propenyl, n-butyl, i-butyl, sec-butyl, tert-butyl, n-pentyl, hexyl, heptyl, octyl, cyclopropyl, cyclopentyl, cyclohexyl and the like. Specific examples of suitable substituents which can be present on the alkyl group when $R_8$, $R_9$, $R_{10}$, $R_{11}$, $R_{12}$, $R_{13}$, $R_{14}$, $R_{15}$, $R_{16}$ and $R_{17}$ represent a substituted alkyl group include halogen atoms such as chlorine, bromine, fluorine and iodine, an aryl group, an alkoxy group, a hydroxy group, and the like. A preferred number of carbon atoms for the unsubstituted and substituted alkyl groups for $R_8$, $R_9$, $R_{10}$, $R_{11}$, $R_{12}$, $R_{13}$, $R_{14}$, $R_{15}$, $R_{16}$ and $R_{17}$ ranges from 1 to 15, more preferably 1 to 10.

The aryl group represented by $R_8$, $R_9$, $R_{10}$, $R_{11}$, $R_{12}$, $R_{13}$, $R_{14}$, $R_{15}$, $R_{16}$ and $R_{17}$ can be a monocyclic, bicyclic or tricyclic aryl group such as a phenyl group, a biphenyl group, a naphthyl group or an anthracenyl group and such may be unsubstituted or substituted. Suitable examples of substituents which can be present on the aryl group represented by $R_8$-$R_{17}$ include one or more of a halogen atom such as chlorine, bromine, fluorine or iodine, an alkyl group, an alkoxy group, a hydroxy group, a nitro group, a cyano group, an amino group, an alkyl- or aryl-substituted amino group, an acylamino group, a sulfonylamino group, a carbamoyl group, a sulfamoyl group, a carboxyl group, an alkoxycarbonyl group, and the like. A suitable number of carbon atoms for the aryl group for $R_8$ to $R_{17}$ is 6 to 20, preferably 6 to 15.

Examples of the rings formed by binding $R_8$ with $R_9$ includes a benzene ring, naphthalene ring, dihydronaphthalene ring, anthracene ring, and phenanthrene ring. In case of a benzene ring, the suitable substituents $R_{1A}$, $R_{2A}$ and $R_{3A}$, which may be present on the benzene ring, may be the same or different, and represent hydrogen atoms, hydroxyl groups, mercapto groups, substituted or unsubstituted alkyl groups (methyl, ethyl, hydroxyethyl, propyl, isopropyl, cyanopropyl, butyl, branched butyl (e.g. isobutyl or t-butyl groups), pentyl, branched pentyl (e.g. isopentyl or t-pentyl groups), vinylmethyl, cyclohexyl, benzyl, phenethyl, 3-phenylpropyl or trifluoromethyl groups or the like) [preferably, having 1 to 5 carbon atoms], substituted or unsubstituted aryl groups (phenyl, 4-methylphenyl, 4-chlorophenyl or naphthyl groups or the like), substituted or unsubstituted alkoxy groups (methoxy, ethoxy, propoxy, butoxy, pentyloxy, benzyloxy or phenethyloxy groups or the like)[preferably, having 1 to 5 carbon atoms], substituted or unsubstituted aryloxy groups (phenoxy, 4-methylphenoxy, 4-chlorophenoxy or naphthyloxy groups or the like), halogen atoms (fluorine, chlorine, bromine, or iodine atoms), substituted or unsubstituted alkoxycarbonyl groups (methoxycarbonyl, ethoxycarbonyl or benzyloxy carbonyl groups or the like) [preferably, having 2 to 6 carbon atoms], substituted or unsubstituted acylamino groups (acetylamino, trifluoroacetylamino, propionylamino or benzoylamino groups or the like), substituted or unsubstituted sulfonylamino groups (methanesulfonylamino or benzenesulfonylamino groups or the like), substituted or unsubstituted acyl groups (acetyl, trifluoroacetyl, propionyl, benzoyl or p-chlorobenzoyl or the like), cyano groups, nitro groups, substituted or unsubstituted carbamoyl groups (carbamoyl, N,N-dimethylcarbamoyl, morpholino carbonyl, piperidine carbonyl or methylpiperadino carbonyl or the like), substituted or unsubstituted sulfamoyl groups (sulfamoyl, N,N-dimethylsulfamoyl, morpholino sulfonyl or piperidine sulfonyl groups or the like), substituted or unsubstituted acyloxy groups (acetyloxy, trifluoroacetyloxy, propionyloxy or benzoyloxy groups or the like), substituted or unsubstituted amino groups (amino, dimethylamino, diethylamino, piperidino, pyrrolidino, morpholino, anilino or methylpiperadino or the like), substituted or unsubstituted alkanesulfonyl groups (methanesulfonyl, trifluoromethanesulfonyl or ethanesulfonyl groups or the like), substituted or unsubstituted arenesulfonyl groups (benzenesulfonyl, p-toluenesulfonyl or p-chlorobenzene sulfonyl groups or the like), substituted or unsubstituted alkylthio groups (methylthio, ethylthio or propylthio groups or the like), substituted or unsubstituted arylthio groups (phenylthio or p-tolythio groups or the like) or substituted or unsubstituted heterocyclic residues (pyridyl, 5-methyl-2-pyridyl or thienyl groups or the like). Further preferred are a chlorine atom, a methoxy, an ethoxy, a methyl, a phenoxy, a phenyl and a methoxycarbonyl group.

Any adjacent two of $R_{1A}$, $R_{2A}$ or $R_{3A}$ may combine and form divalent substituents (methylenedioxy, trimethylene or tetramethylene groups or the like).

$R_{1A}$, $R_{2A}$ or $R_{3A}$ may be further substituted by the abovementioned substituents (methoxyethoxy, dimethylamino ethylamino, or dimethylamino ethylthio groups or the like).

Moreover, two of $R_{10}$, $R_{11}$, $R_{12}$ and $R_{13}$ may combine and form a 5- or 6-membered carbocyclic ring. A suitable number of carbon atoms for the carbocyclic ring including substituent groups thereon or $R_{10}$, $R_{11}$, $R_{12}$ and $R_{13}$ is 3 to 15 carbon atoms, preferably 3 to 10 carbon atoms.

Typical examples of 5- and 6-membered carbocyclic rings include a cyclopentane ring, a cyclopentene ring, a cyclohexane ring, a cyclohexene ring and the like.

$Z_1$ and $Z_2$, which may be the same or different, each represents an atomic group necessary to form a saturated or unsaturated heterocyclic ring. Moreover, the ring formed by $Z_1$ and $Z_2$ can be substituted with one or more substituents or can be condensed with another ring such as a saturated or unsaturated ring, e.g., a cyclohexene ring, a benzene ring or a naphthalene ring. Suitable examples of substituents which can be present on the ring formed by $Z_1$ and $Z_2$ include one or more of an alkyl group, an alkoxy group, an aryloxy group, a halogen atom (such as chlorine, bromine, fluorine and iodine), an aryl group, a hydroxy group, an amino group, an alkyl- or aryl-substituted amino group, an acylamino group, a sulfonylamino group, a carbamoyl group, a sulfamoyl group, a carboxyl group, an alkoxycarbonyl group, an acyloxy group, a heterocyclic ring (such as a pyrrole ring, a furan ring, a piperidine ring, a morpholine ring, a pyridine ring, etc.) a cyano group, a nitro group, and the like, and suitable examples of saturated or unsaturated rings condensed therewith include a cyclopentene ring, a cyclohexene ring, a benzene ring, a naphthalene ring, an anthracene ring, a phenanthrene ring, a thiophene ring, a pyridine ring, etc.

Specific examples of heterocyclic rings formed by $Z_1$ and $Z_2$ include 5- and 6-membered heterocyclic rings such as those including nuclei comprising those of the thiazole series (e.g., thiazole, 4-methylthiazole, 4-phenylthiazole, 4,5-diphenylthiazole, 4,5-dimethylthiazole, etc.), those of the benzothiazole series (e.g., benzothiazole, 5-chlorobenzothiazole, 5-methylbenzothiazole, 5-phenylbenzothiazole, 5-methoxybenzothiazole, 4-fluorobenzothiazole, 5,6-dioxymethylenebenzothiazole, 5-nitrobenzothiazole, 5-trifluoromethylbenzothiazole, 5-methoxycarbonylbenzothiazole, 5-hydroxybenzothiazole, 6-hydroxybenzothiazole, 5-cyanobenzothiazole, 5-iodobenzothiazole, etc.), those of the naphthothiazole series (e.g., α-naphthothiazole, β-naphthothiazole, γ-naphthothiazole, 5-methoxy-β-naphthothiazole, 8-methoxy-α-naphthothiazole, 6-methoxy-8-acetyloxy-β-naphthothiazole, 8,9-dihydro-β-naphthothiazole, etc.), those of the oxazole series (e.g., 4-methyloxazole, 4,5-diphenyloxazole, 4-phenoxyoxazole, etc.), those of the benzoxazole series (e.g., benzoxazole, 5-chlorobenzoxazole, 5,6-dimethylindolenine, 6-hydroxybenzoxazole, 5-phenylbenzoxazole, etc.), those of the naphthoxazole series (e.g., α-naphthoxazole, β-naphthoxazole, etc.), those of the selenazole series (e.g., 4-methylselenazole, 4-phenylselenazole, etc.), those of the benzoselenazole series (e.g., benzoselenazole, 5-chlorobenzoselenazole, 5-methoxybenzoselenazole, 5-hydroxybenzosetenazole, etc.), those of the thiazoline series (e.g., thiazoline, 4,4-dimethylthiazoline, etc.), those of the 2-pyridine series. (e.g., 2-pyridine, 5-methyl-2-pyridine, 5-methoxy-2-pyridine, 4-chloro-2-pyridine, 5-carbamoyl-2-pyridine, 5-methoxycarbonyl-2-pyridine, 4-acetylamino-2-pyridine, 6-methylthio-2-pyridine, 6-methyl-2-pyridine etc.), those of the 4-pyridine series (e.g., 4-pyridine, 3-methoxy-4-pyridine, 3,5-dimethyl-4-pyridine, 3-chloro-4-pyridine, 3-methyl-4-pyridine, etc.), those of the 2-quinoline series (e.g., 2-quinoline, 6-methyl-2-quinoline, 6-chloro-2-quinoline, 6-ethoxy-2-quinoline, 6-hydroxy-2-quinoline, 6-nitro-2-quinoline, 6-acetylamino-2-quinoline, 6-dimethylaminocarbonyl-2-quinoline, 8-fluoro-2-quinoline, etc.), those of the 4-quinoline series (e.g., 4-quinoline, 6-methoxy-4-quinoline, 6-acetylamino-4-quinoline, 8-chloro-4-quinoline, 6-trifluoromethyl-4-quinoline, etc.), those of the 1-isoquinoline series (e.g., 1-isoquinoline, 6-methoxy-1-isoquinoline, 6-chloro-1-isoquinoline, etc.), those of the 3,3-dialkylindolenine series (e.g., 3,3-dimethylindolenine, 3,3,7-trimethylindolenine, 5-chloro-3,3-dimethylindolenine, 5-ethoxyarbonyl-3,3-dimethylindolenine, 5-nitro-3,3-dimethylindolenine, 3,3-dimethyl-4,5-phenyleneindolenine, 3,3-dimethyl-6,7-phenyleneindolenine, 5-acetylamino-3,3-dimethylindolenine, 5-diethylamino-3,3-dimethylindolenine, 5-methanesulfonylamino-3,3-dimethylindolenine, 5-benzoylamino-3,3-dimethylindolenine, etc.), those of the imidazole series (e.g., imidazole, 1-alkyl-4-phenylimidazole, 1-alkyl-4,5-dimethylimidazole, etc.), those of the benzimidazole series (e.g., benzimidazole, 1-alkylbenzimidazole, 1-alkyl-5-trifluorobenzimidazole, 1-alkyl-5-chlorobenzimidazole, 1-alkyl-5-sulfamoylbenzimidazole, 1-aryl-5-methoxycarbonylbenzimidazole, 1-alkyl-5-acetylaminobenzimidazole, 1-alkyl-5-nitrobenzimidazole, 1-alkyl-5-diethylaminobenzimidazole, 1-alkyl-5-pentyloxybenzimidazole, etc.), those of naphthimidazole series (e.g., 1-alkyl-α-naphthimidazole, 1-alkyl-5-methoxy-β-naphthimidazole, etc.) and like rings.

In cases where $Z_2$ is a pyridine ring, examples of the substituents $R_{4A}$ and $R_{5A}$, which may be present on the ring, include a halogen atom (preferably a chlorine atom), an alkyl group (preferably an alkyl group having 1 to 5 carbon atoms), and an alkoxycarbonyl group (preferably a methoxycarbonyl group).

Suitable examples of substituents which can be present on the $L_1$ substituted methine group include an alkyl group (e.g., methyl, ethyl, butyl, etc.), an aryl group (e.g., phenyl, tolyl, etc.), a halogen atom (e.g., chlorine, bromine, fluorine and iodine), or an alkoxy group (e.g., methoxy, ethoxy, etc.) and suitable rings formed by the combination of $L_1$ and $R_3$ include a 5-membered heterocyclic ring (e.g., a pyrroline ring, etc.) and a 6-membered heterocyclic ring (e.g., a tetrahydropyridine ring, an oxazine ring, etc.).

The term "pharmaceutically acceptable anion" for Q which is necessary for electrical charge balance in the compounds above is intended to mean an ion, when administered to the host subjected to the method of treatment of this invention, which is non-toxic and which renders the compounds above soluble in aqueous systems.

Suitable examples of pharmaceutically acceptable anions represented by Q include halides such as chloride, bromide and iodide, sulfonates such as aliphatic and aromatic sulfonates, e.g., methanesulfonate, trifluoromethanesulfonate, p-toluenesulfonate, naphthalenesulfonate, 2-hydroxyethanesulfonate, and the like, sulfamates such as cyclohexanesulfamate, sulfates such as methyl sulfate and ethyl sulfate, bisulfates, borates, alkyl and dialkyl phosphates such as diethyl phosphate and methylhydrogen phosphate, pyrophosphates such as trimethylpyrophosphate and diethyl hydrogen pyrophsophate, carboxylates, advantageously carboxy- and hydroxy-substituted carboxylates and carbonates. Preferred examples of pharmaceutically acceptable anions include chloride, acetate, propionate, valerate, citrate, maleate, fumarate, lactate, succinate, tartrate and benzoate.

In particular, compounds of the General Formula (I) to (V) where $Y_1$ is a sulfur atom are preferred. Particularly preferred compounds are compounds of the General Formula (I) to (V) where $Y_1$ is a sulfur atom, and $L_1$ is =CH—.

Particularly preferable compounds having the formulae (I) to (IV) are as follows:

In the compounds having the formula (IIA), $X_1$ is O, S, Se, —CH=CH—, —C(CH$_3$)$_2$—, —NCH$_3$—, —NCH$_2$CH$_3$—, or —N(phenyl)-; $X_2$ is O, S, Se, —CH=CH—, —C(CH$_3$)$_2$—; $Y_1$ is O, S, Se, —NCH$_3$—, —NCH$_2$CH$_3$—, or —N(phenyl)-; $R_{1A}$, $R_{2A}$ and $R_{3A}$, which may be the same or different, each represents a hydrogen atom, a halogen atom, a hydroxy group, an alkyl group having 1 to 5 carbon atoms, an alkoxy group having 1 to 5 carbon atoms, a phenyl group, a phenoxy group or an alkoxycarbonyl group having 2 to 6 carbon atoms; and $Z_2$ represents an atomic group necessary to form a ring of thiazole, benzothiazole, naphthothiazole, benzoxazole, naphthoxazole, benzoselenazole, thiazoline, 2-pyridine, 4-pyridine, 2-quinoline, 4-quinoline or 3,3-dimethylindolenine, and more preferred are those compounds wherein $X_1$ is O, S or —CH=CH—; $X_2$ is O, S, Se, or —CH=CH—; $Y_1$ is S, and $Z_2$ is an atomic group necessary to form the above rings except for the 3,3-dimethylindolenine ring, most preferred are those compounds wherein $X_1$ is S or O; and at least one of $R_{1A}$, $R_{2A}$ and $R_{3A}$ is a hydrogen atom.

In the compounds having the formula (IIB), $R_1$ and $R_3$, which may be the same or different, each represents methyl, ethyl, propyl or butyl; $R_2$ is methyl, ethyl, allyl or phenyl; $R_{1A}$ and $R_{2A}$, which may be the same or different, each represents methyl, methoxy, chlorine atom or methoxycarbonyl; $R_{4A}$ and $R_{5A}$, which may be the same or different, each represents methyl, chlorine atom or methoxycarbonyl; Q— is a chlorine ion, bromine ion, iodine ion, or acetate ion; and k is 2.

Regarding compounds having the formula (II) other than those mentioned above, preferred are those wherein $X_1$ is O, S or —$NR_6$—; $X_2$ is O, S, Se or —CH=CH—; $Y_1$ is O, S or —$NR_7$—; $R_1$ and $R_3$, which may be the same or different, each represents an alkyl group having 1 to 8 carbon atoms; $R_2$ is an alkyl group having 1 to 8 carbon atoms or an aryl group having 6 to 8 carbon atoms; $R_6$ and $R_7$, which may be the same or different, each represents an alkyl group or an aryl group; and $R_8$ and $R_9$, which may be the same or different, each represents a hydrogen atom, an alkyl group or an aryl group, more preferred are those compounds wherein $X_1$ is O, S, —$NCH_3$—, —$NCH_2CH_3$— or —$NCH_2CH_2OCH_3$—; $Y_1$ is O, S, —$NCH_3$—, —$NCH_2CH_3$— or —N(phenyl)-; $R_8$ and $R_9$, which may be the same or different, each represents a hydrogen atom or a methyl group.

Preferred are also compounds having the formula (II) wherein $X_1$ is O, S or —$NR_6$—; $X_2$ is O, S, Se or —CH=CH—; $Y_1$ is S; $R_1$ and $R_3$, which may be the same or different, each represents an alkyl group having 1 to 8 carbon atoms; $R_2$ is an alkyl group having 1 to 8 carbon atoms or an aryl group having 6 to 8 carbon atoms; $R_6$ and $R_7$, which may be the same or different, each represents an alkyl group or an aryl group; and $R_8$ and $R_9$ are combined with each other to form an atomic group necessary to form a ring of naphthalene, dihydronaphthalene, anthracene or phenathrene, more preferred are those compounds wherein $X_1$ is O or S; $R_8$ and $R_9$ are combined with each other to form an atomic group necessary to form a ring of naphthalene or dihydronaphthalene; and $Z_2$ is an atomic group necessary to form a ring of thiazole, benzothiazole, naphthothiazole, benzoxazole, naphthoxazole, benzoselenazole, thiazoline, 2-pyridine, 4-pyridine, 2-quinoline and 4-quinoline, most preferred are those compounds wherein $X_1$ is S; $X_2$ is O, S or —CH=CH—; $R_1$ is methyl, ethyl or propyl; $R_2$ and $R_3$, which may be the same or different, each represents methyl or ethyl; $R_8$ and $R_9$ are combined with each other to form an atomic group necessary to form a ring of naphthalene or dihydronaphthalene; $Z_2$ is an atomic group necessary to form a ring of thiazole, benzothiazole, naphthothiazole, benzoxazole, naphthoxazole, benzoselenazole, thiazoline, 2-pyridine, 4-pyridine, 2-quinoline and 4-quinoline; and k is 2 and most preferred are also those compounds wherein $X_1$ is O; $X_2$ is O, S or —CH=CH—; $R_1$ is a methyl group; $R_2$ is a methyl group; $R_3$ is a methyl or ethyl group; $R_8$ and $R_9$ are combined with each other to form an atomic group necessary to form a ring of naphthalene; $Z_2$ is an atomic group necessary to form a ring of thiazole, benzothiazole, naphthothiazole, benzoxazole, naphthoxazole, benzoselenazole, thiazoline, 2-pyridine, 4-pyridine, 2-quinoline and 4-quinoline; and k is 2.

Among compounds having the formula (III), most preferred are those compounds wherein $X_1$, $X_2$ and $Y_1$ are S; $R_1$ and $R_2$ which may be the same or different, each represents an alkyl group having 1 to 3 carbon atoms; $R_3$ is an alkyl group having 1 to 5 carbon atoms; $R_{10}$, $R_{11}$, $R_{12}$ and $R_{13}$ are hydrogen atoms; $Z_2$ is an atomic group necessary to form a ring of thiazole, benzothiazole and naphthothiazole; $L_1$ is a methine group; k is 2; and n is 0.

Among compounds having the formula (IV), preferred are those compounds represented by the formulae (IVA) and (IVB). Among compounds having the formula (V), preferred are those compounds wherein $X_2$ is O, S, Se or —CH=CH—; $Y_1$ is S; $R_1$ and $R_3$ are alkyl groups having 1 to 3 carbon atoms; and $R_2$ is an alkyl group having 1 to 8 carbon atoms.

The compounds of general Formulas (I) to (V) described above can be easily produced from known starting materials in accordance with the methods disclosed in British Patent Nos. 489,335 and 787,051; in U.S. Pat. Nos. 2,388,963, 2,454,629 and 2,504,468; in E. B. Knott et al, J. Chem. Soc., 4762 (1952) and in E. B. Knott, J. Chem. Soc., 949 (1955), the disclosure of which is incorporated herein by reference.

Typical examples of compounds of General Formula (I) to (V) which can be employed in this invention include the following compounds; however, the present invention is not to be construed as being limited to these compounds.

| Compound No. | Structure |
| --- | --- |
| 1 | 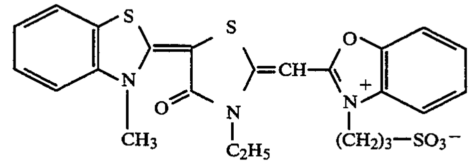 |

2 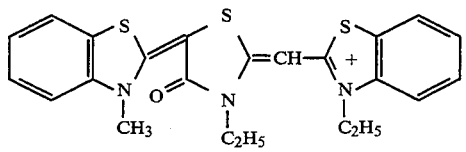
3 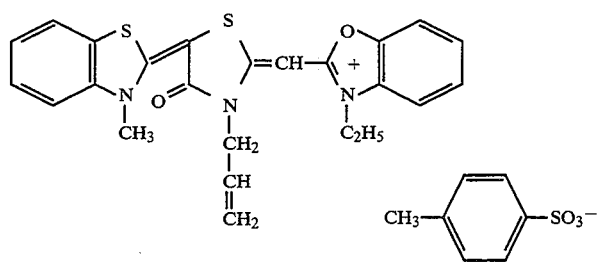
4 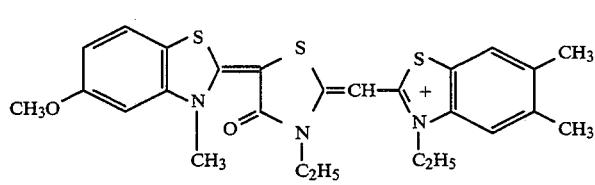
5 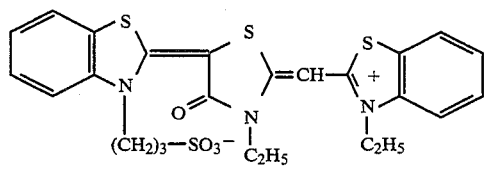
6 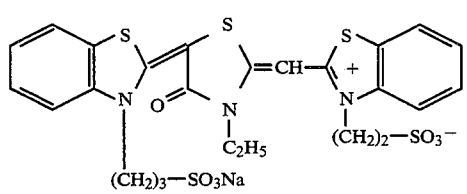
7 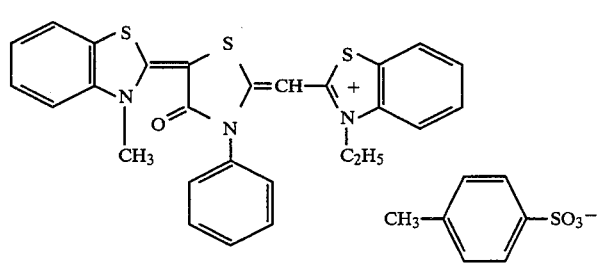
8 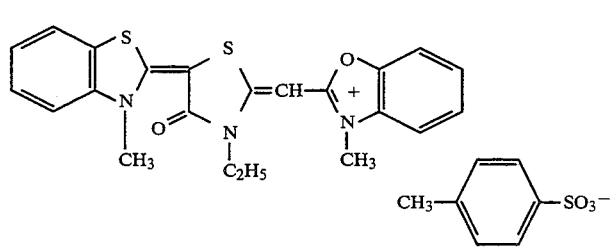

-continued
9 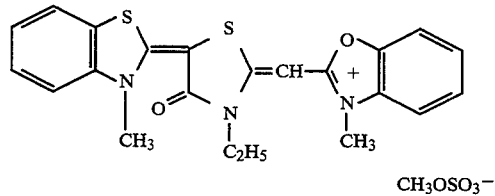
CH₃OSO₃⁻
10 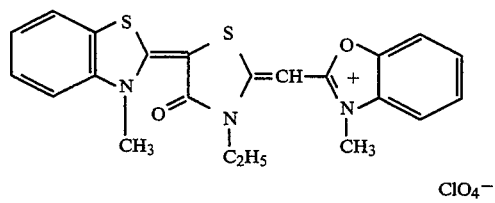
ClO₄⁻
11 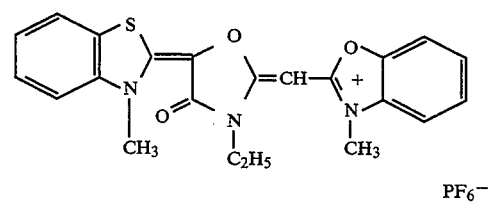
PF₆⁻
12 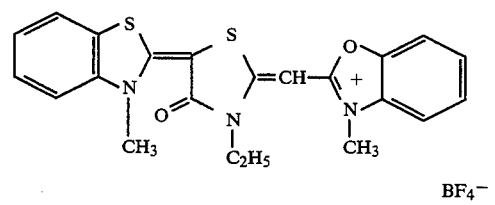
BF₄⁻
13 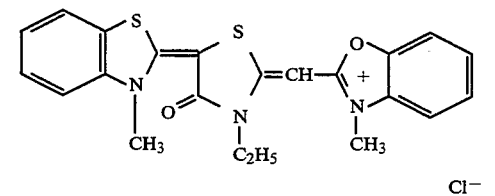
Cl⁻
14 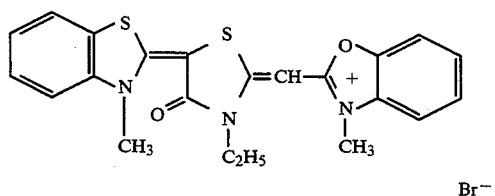
Br⁻
15 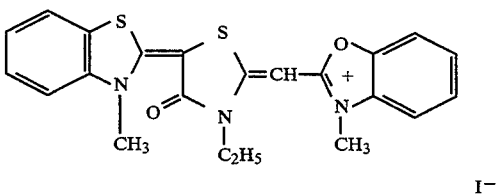
I⁻

-continued
16 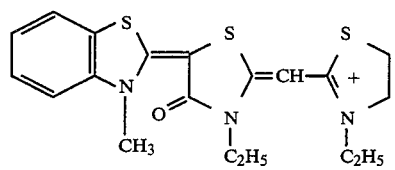
I⁻
17 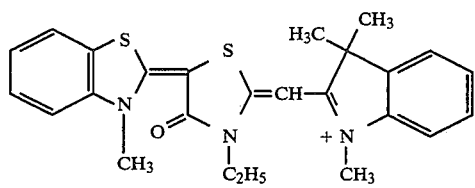
Br⁻
18 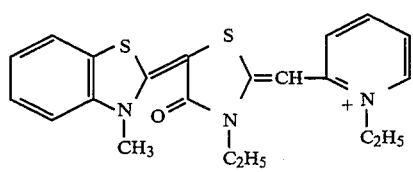
I⁻
19 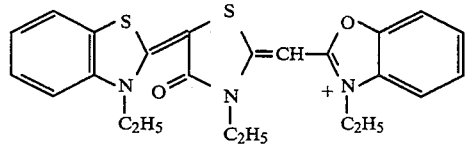
I⁻
20 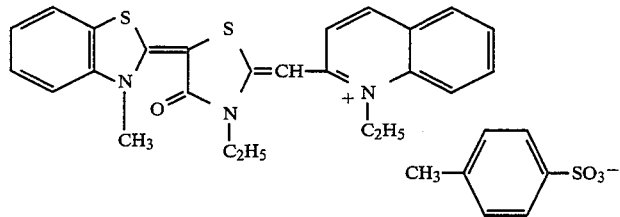
21 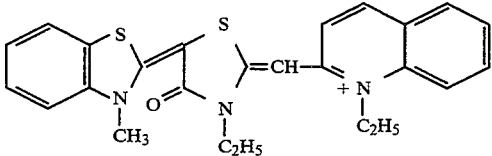
I⁻
22 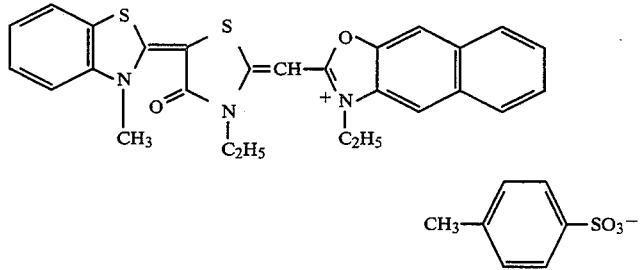

-continued
23
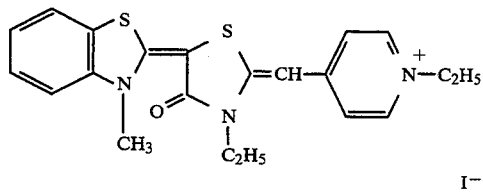
I⁻
24
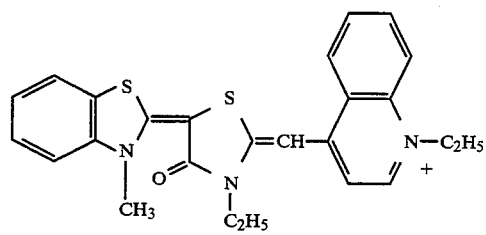
I⁻
25
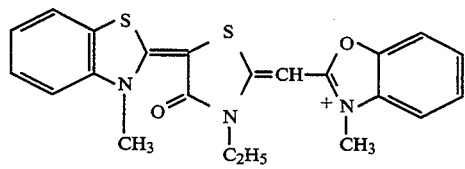
HOSO₃⁻
26
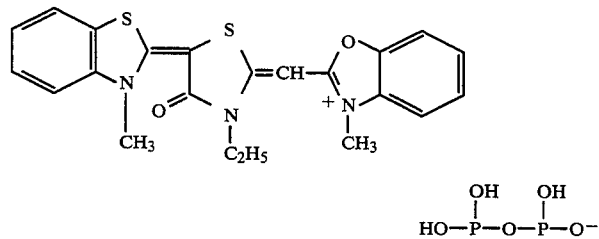
27
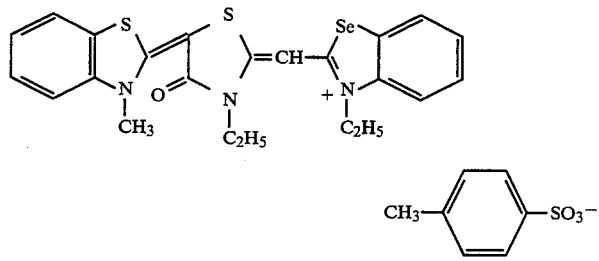
28
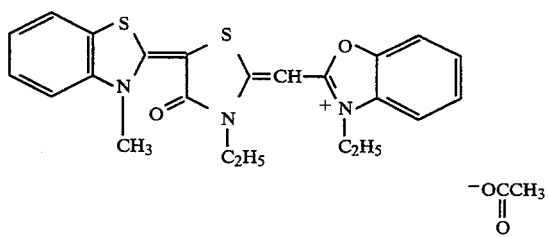

29 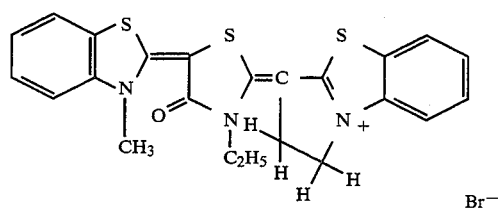
30 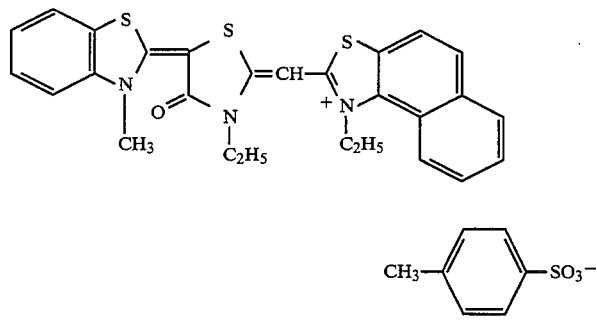
31 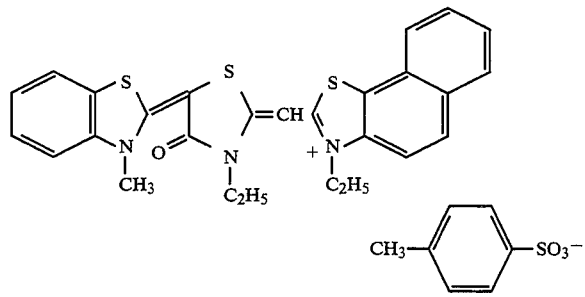
32 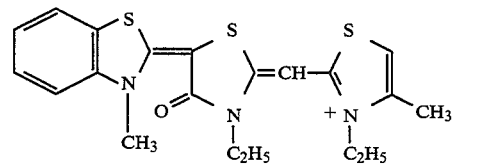
33 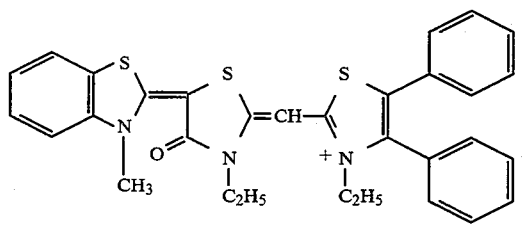
34 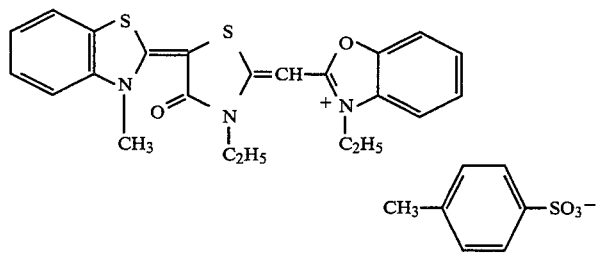

-continued
35
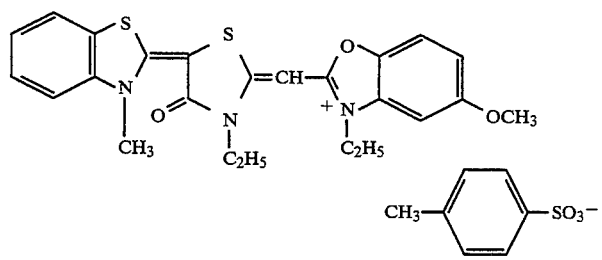
36
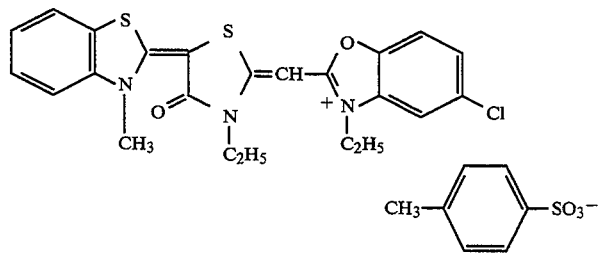
37
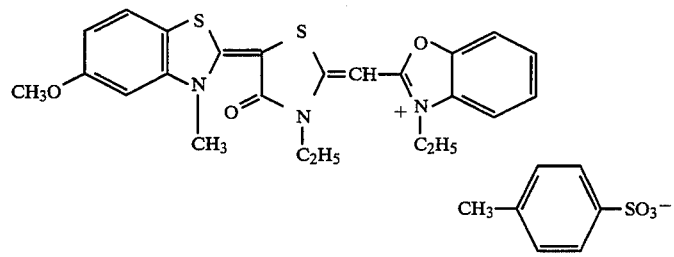
38
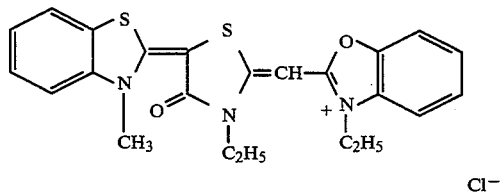
39
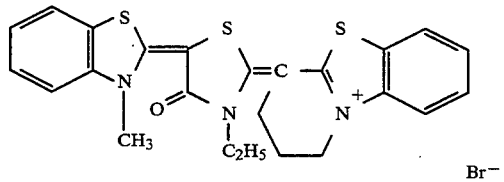
40
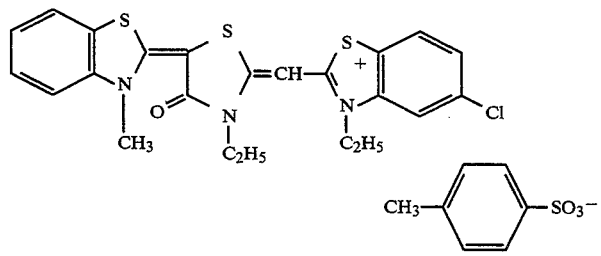

41 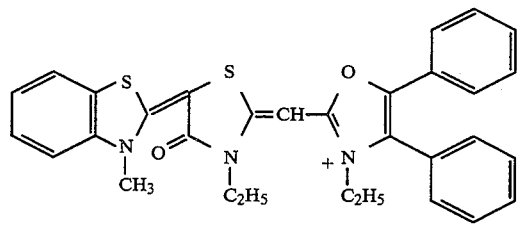
I⁻
42 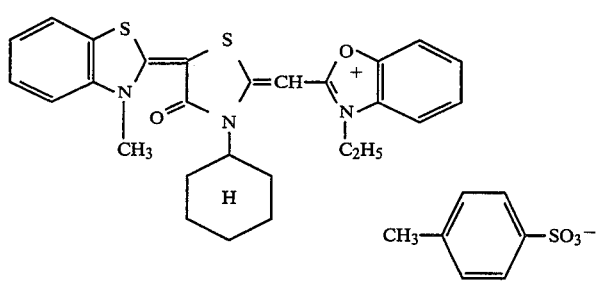
43 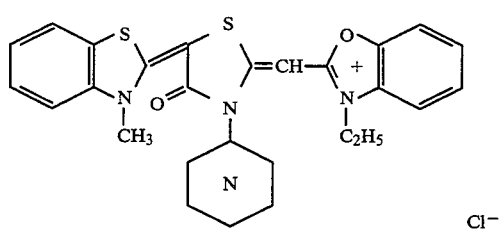
Cl⁻
44 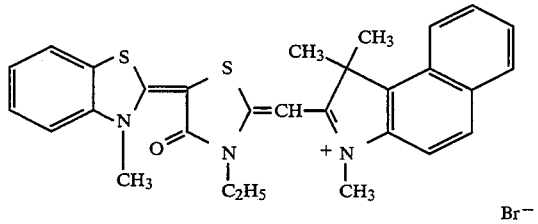
Br⁻
45 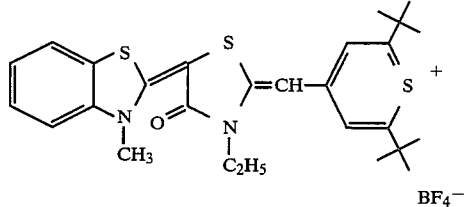
BF₄⁻
46 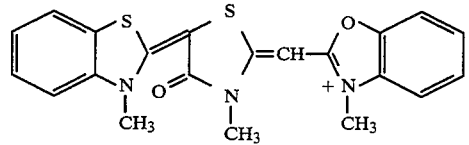
Cl⁻
47 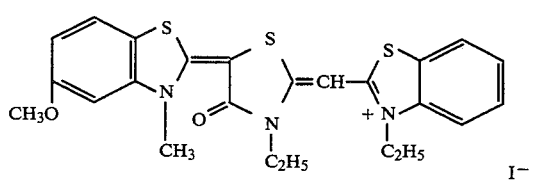
I⁻

| | |
|---|---|
| 48 | 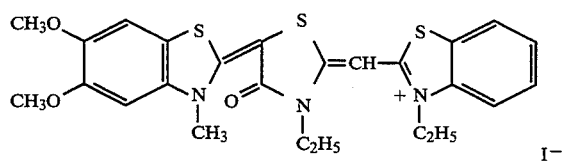 I⁻ |
| 49 | 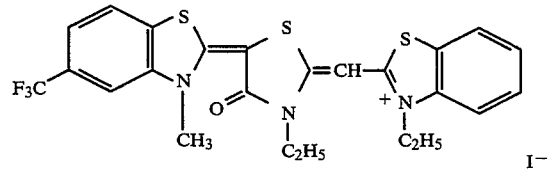 I⁻ |
| 50 | 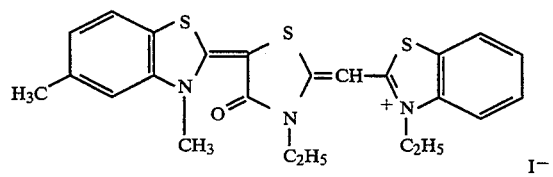 I⁻ |
| 51 | 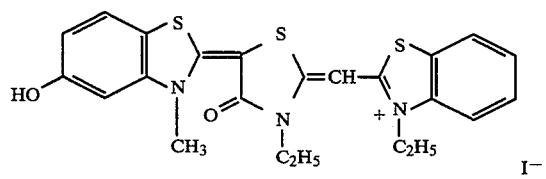 I⁻ |
| 52 | 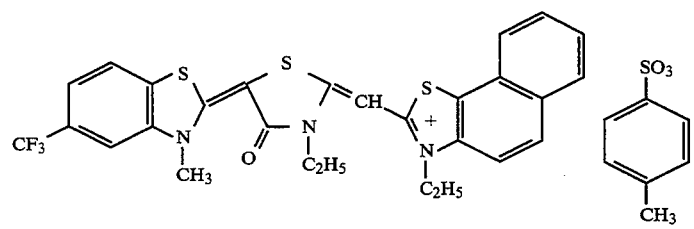 |
| 53 | 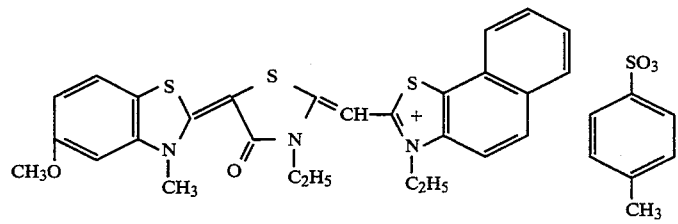 |
| 54 | 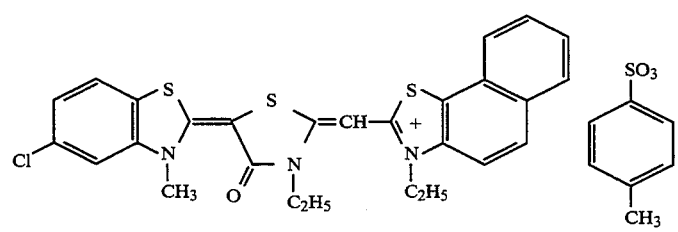 |

55 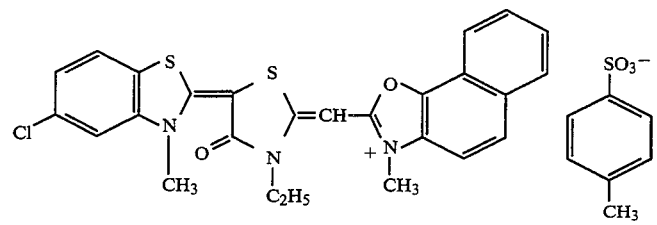
56 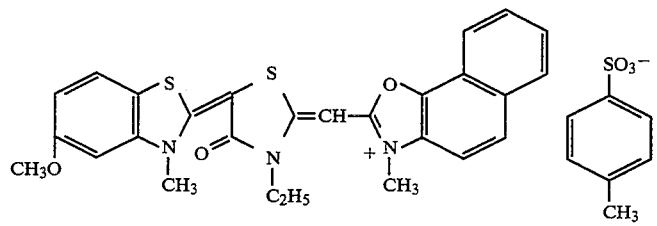
57 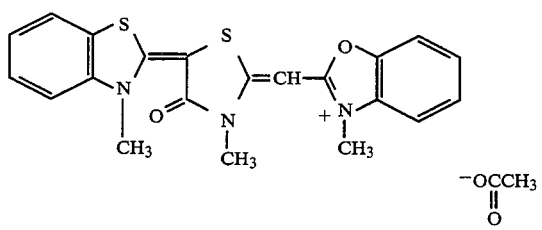
58 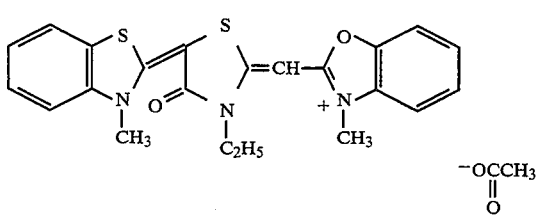
59 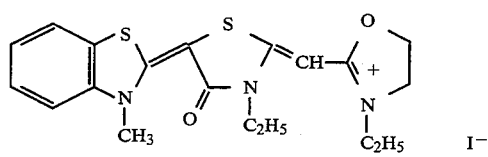
60 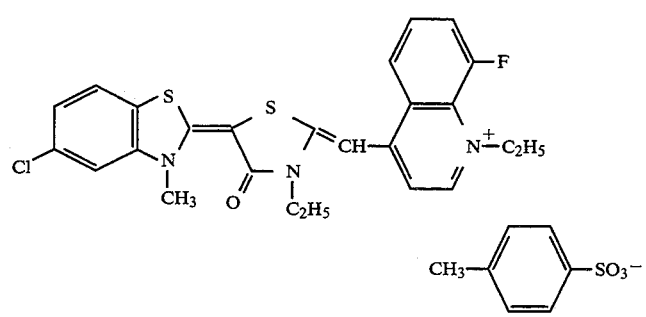

-continued
61
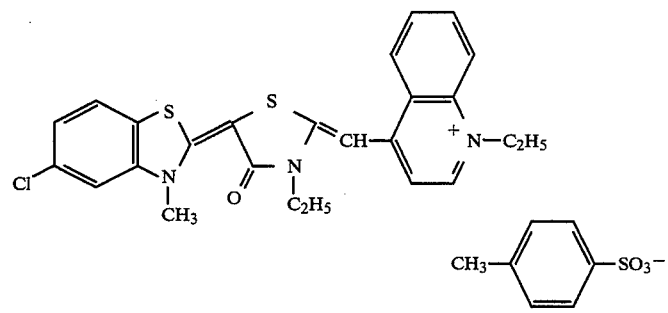
62
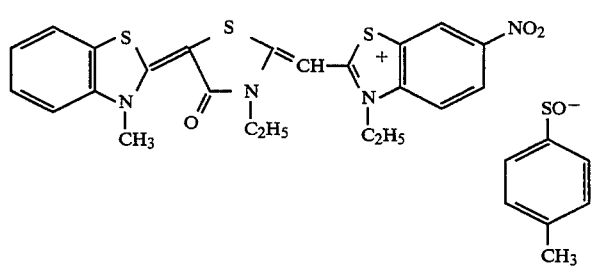
63
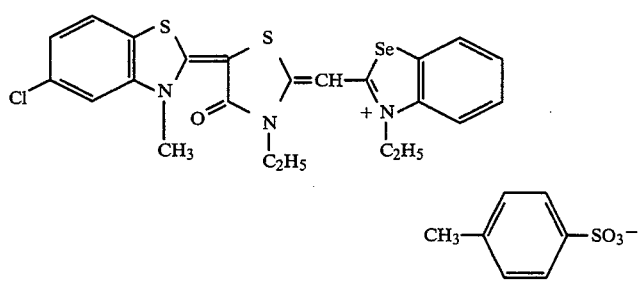
64
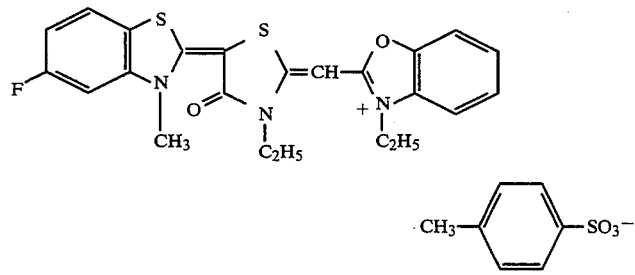
65
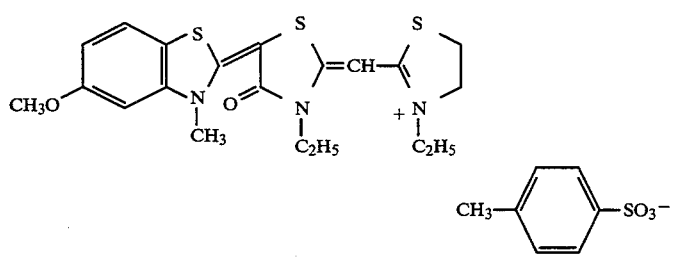

66 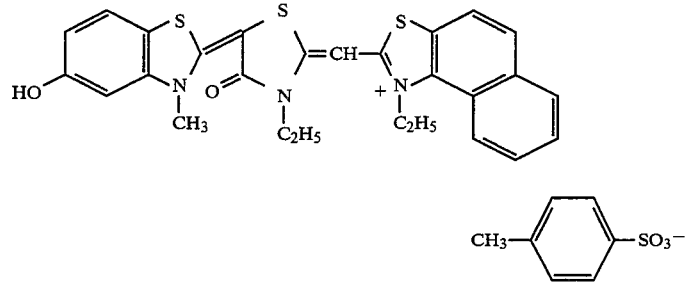
67 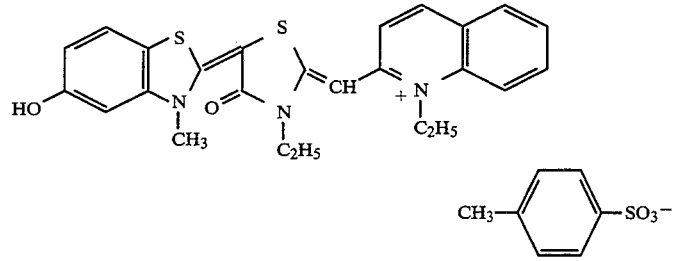
68 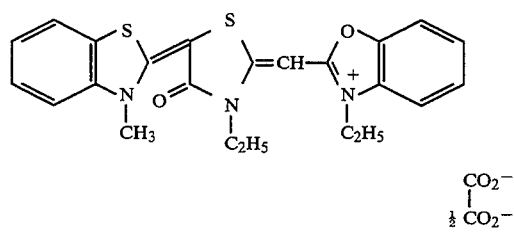
69 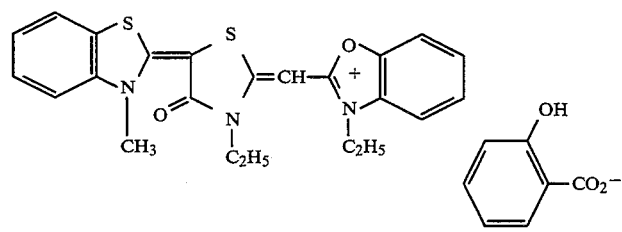
70 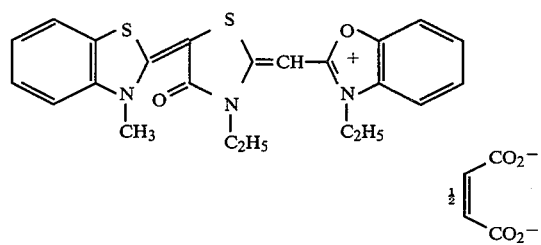
71 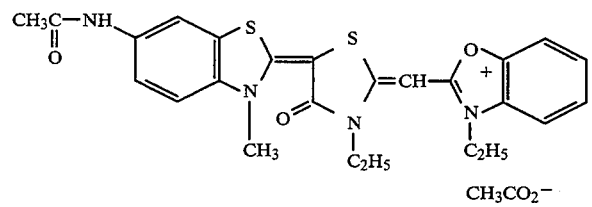

-continued
72 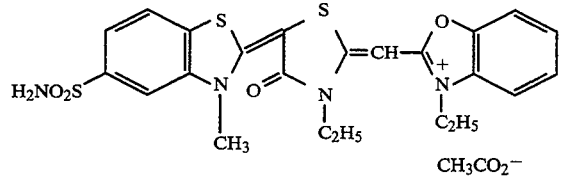
73 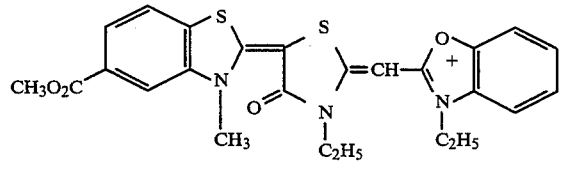
74 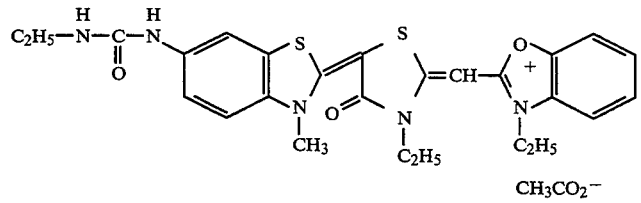
75 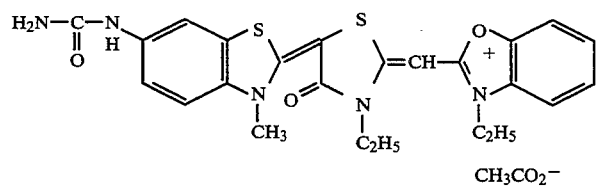
76 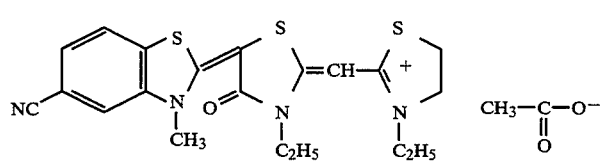
77 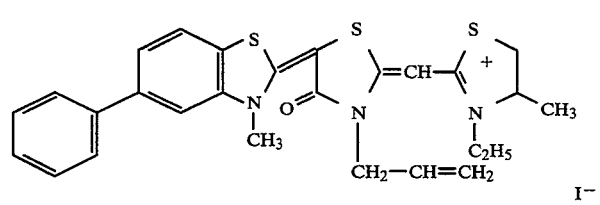
78 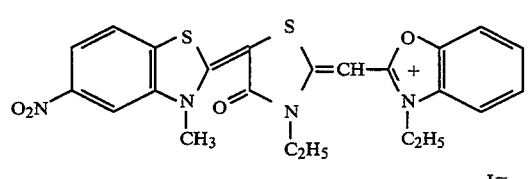
79 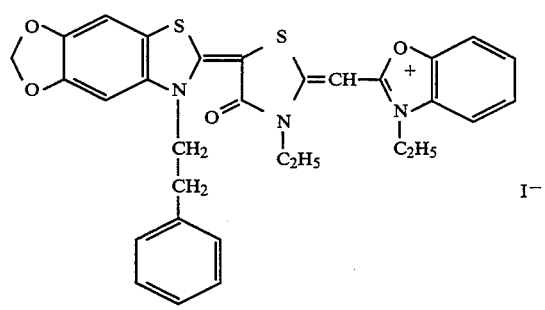

80
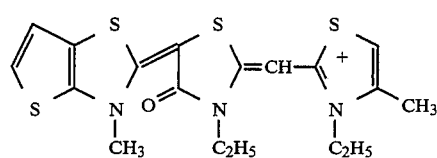
Cl⁻
81
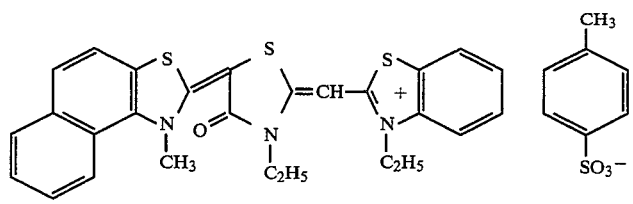
82
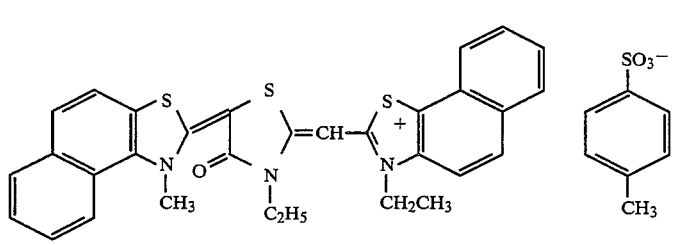
83
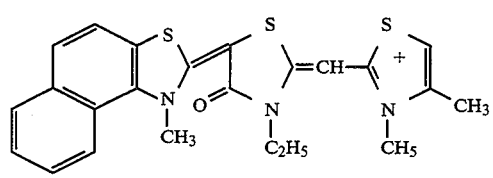
I⁻
84
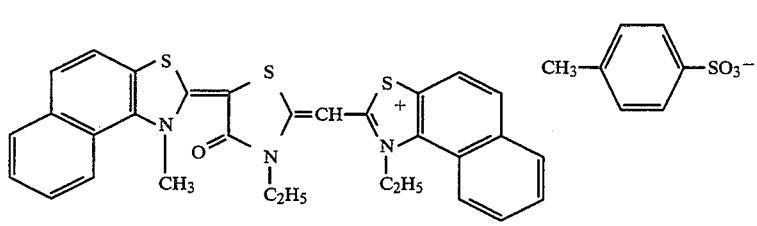
85
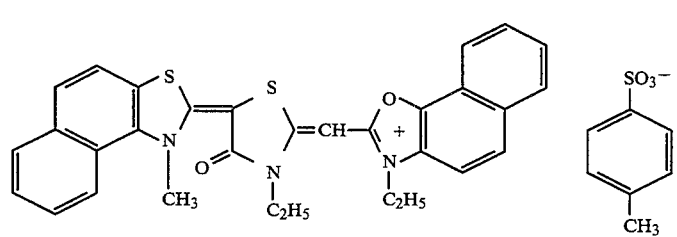
86
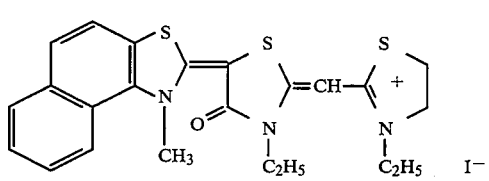
I⁻

87 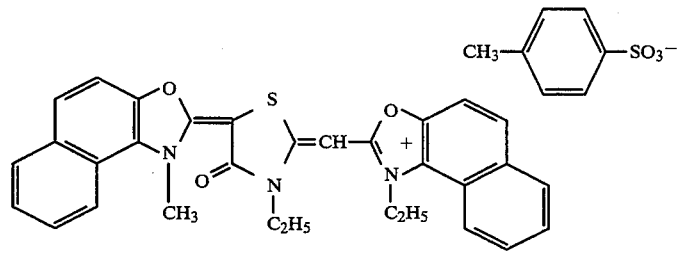
88 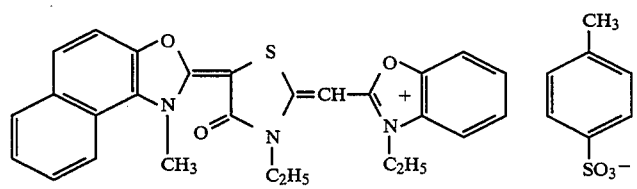
89 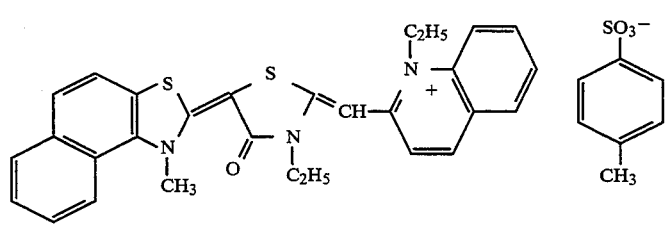
90 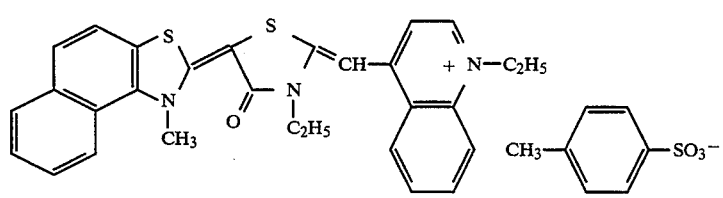
91 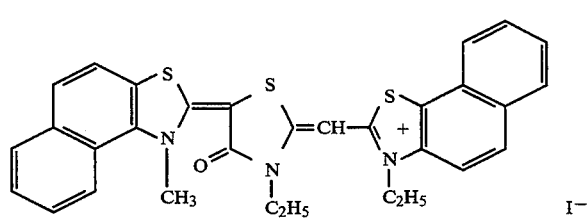
92 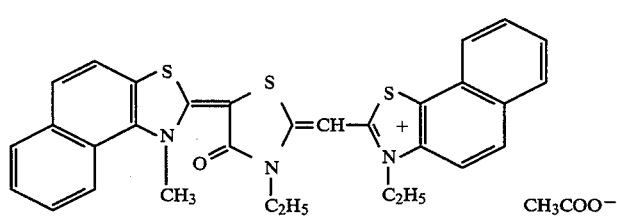
93 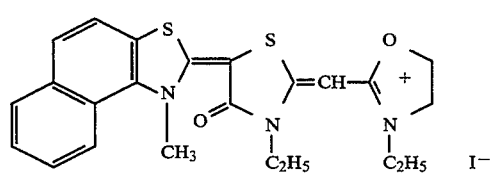

94 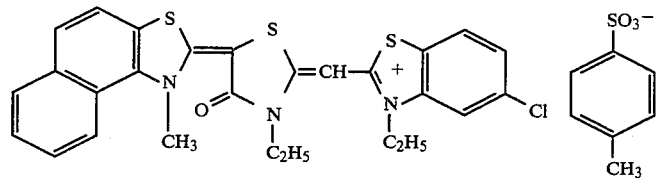
95 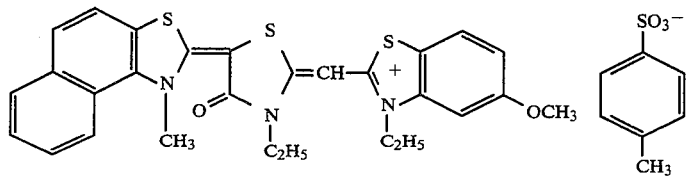
96 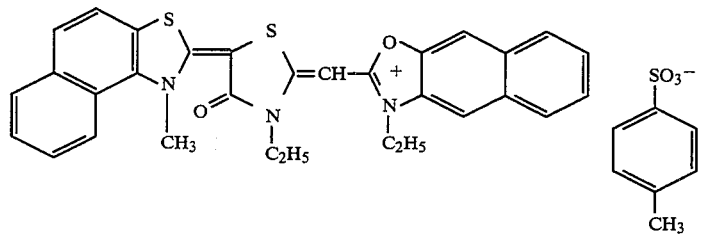
97 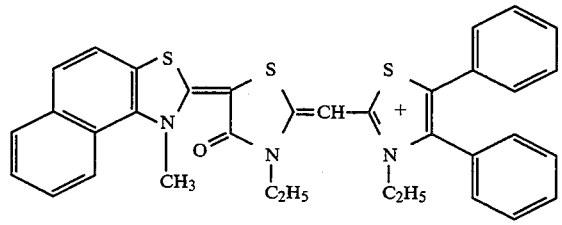
98 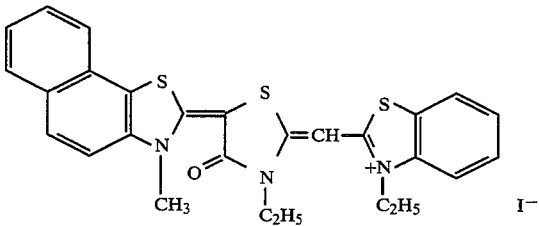
99 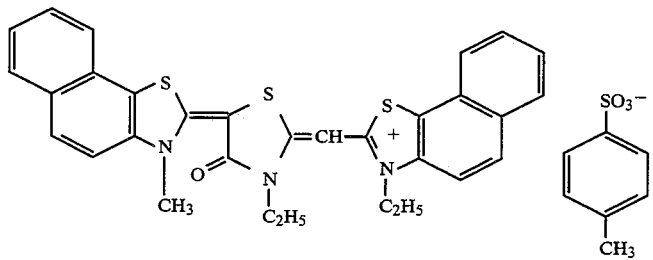
100 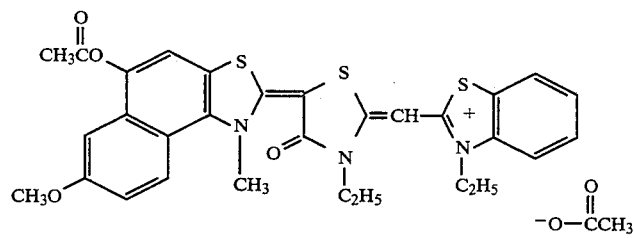

101
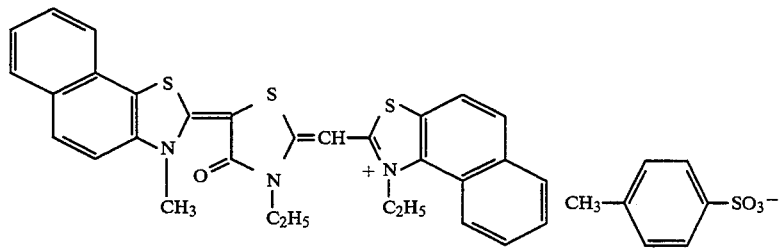
102
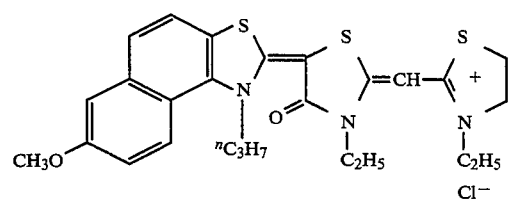
103
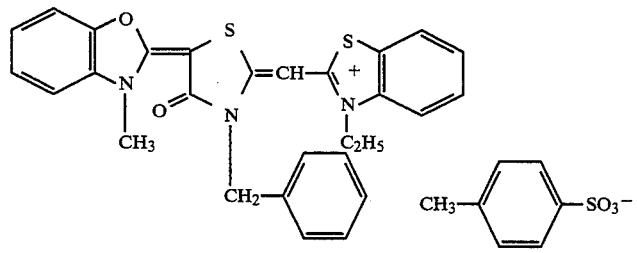
104
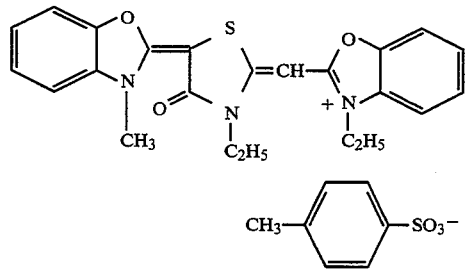
105
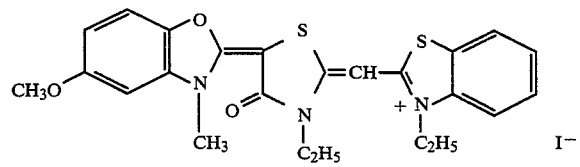
106
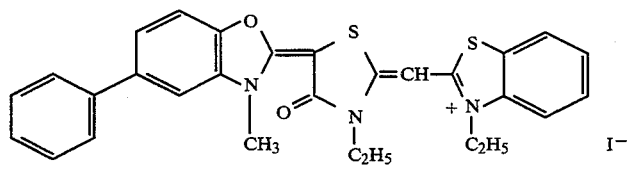
107
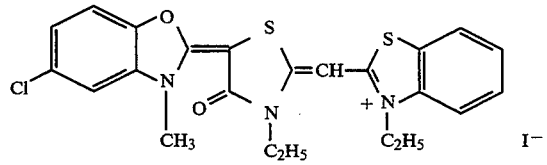

108
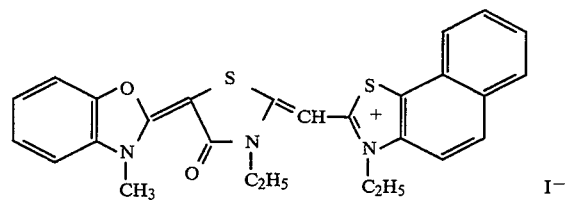
I⁻
109
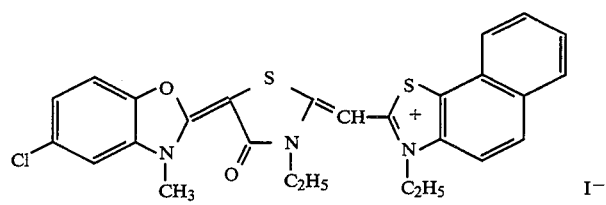
I⁻
110
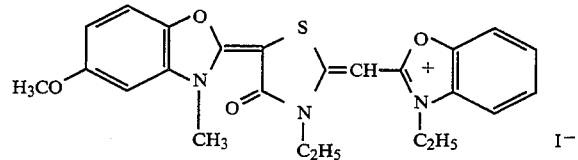
I⁻
111
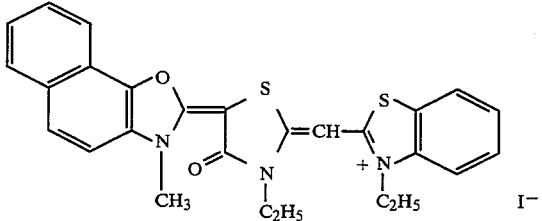
I⁻
112
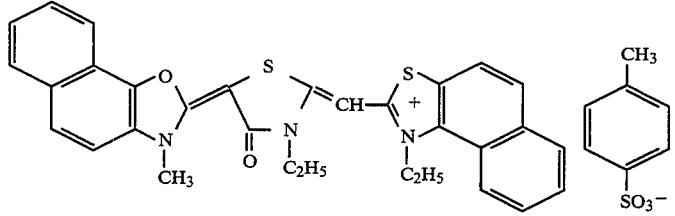
113
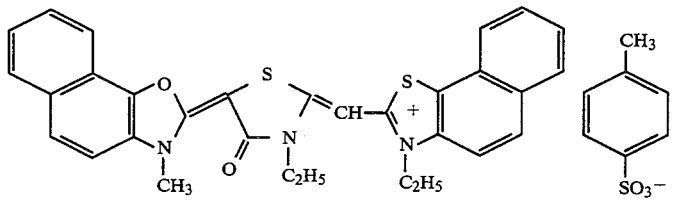
114
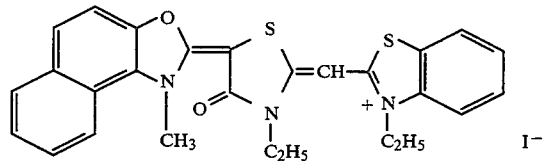
I⁻

115 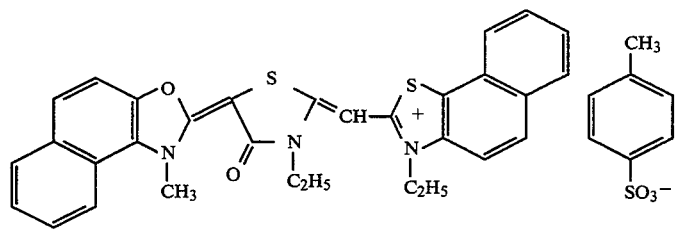
116 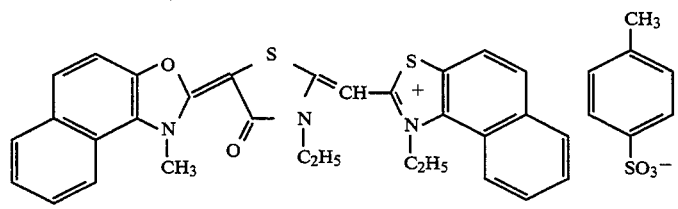
117 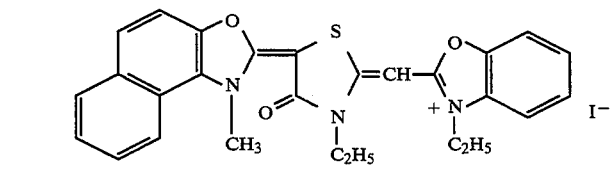
118 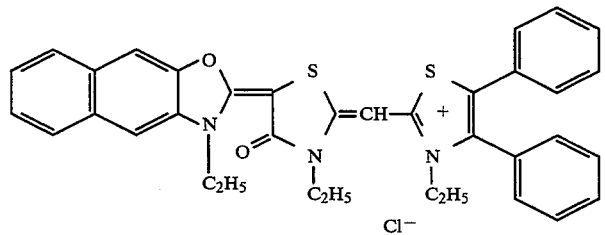
119 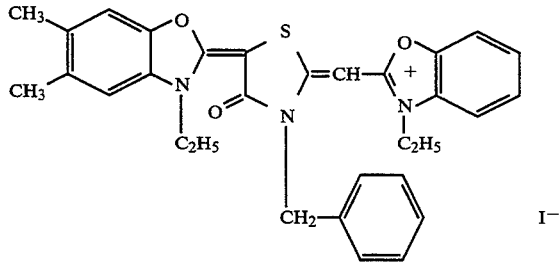
120 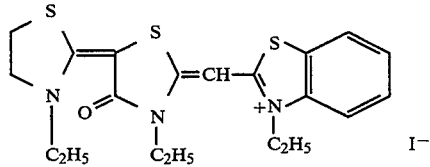
121 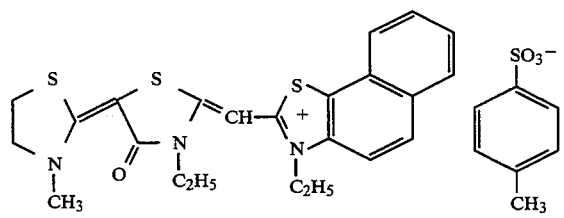

122 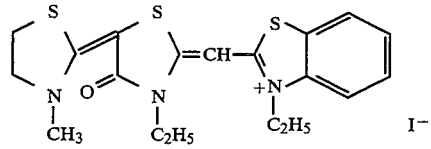
123 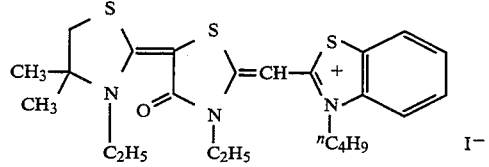
124 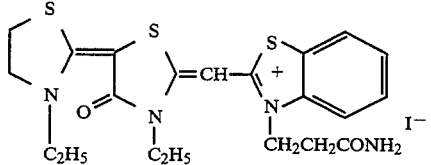
125 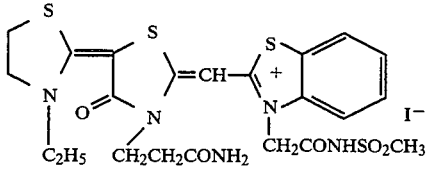
126 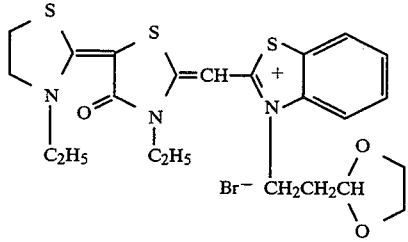
127 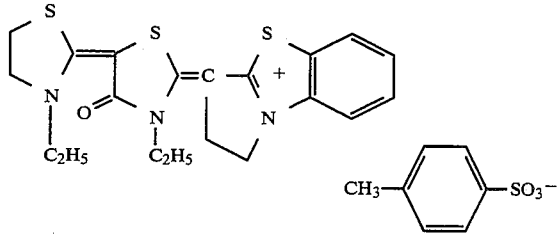
128 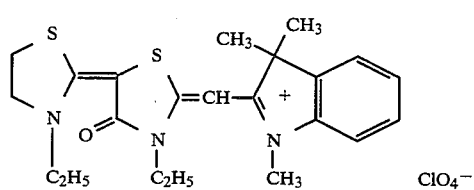
129 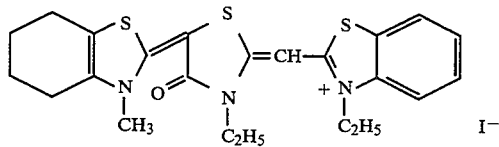

130
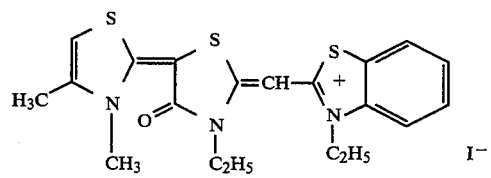
I⁻
131
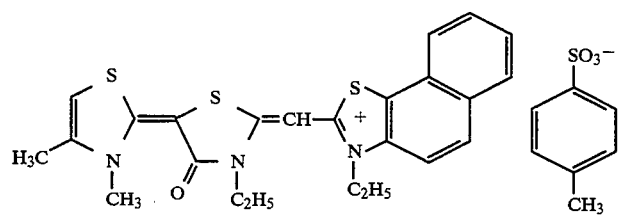
132
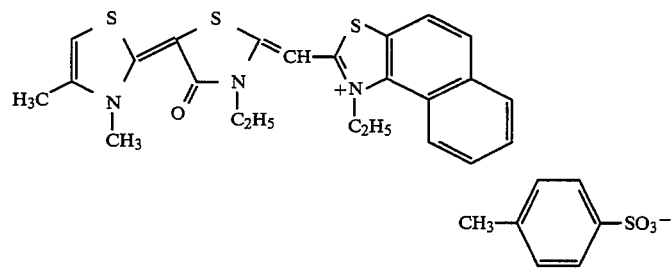
133
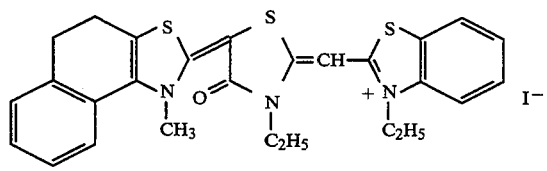
I⁻
134
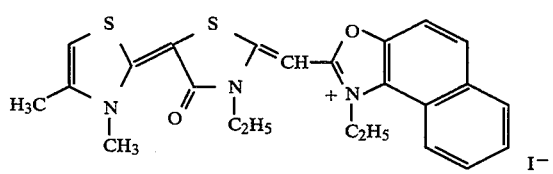
I⁻
135
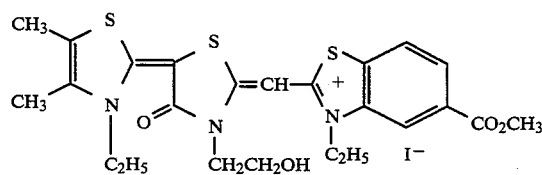
I⁻
136
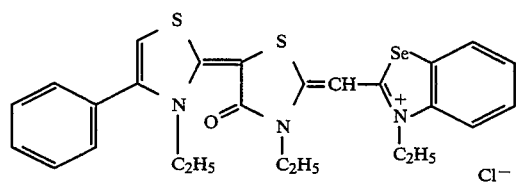
Cl⁻

137 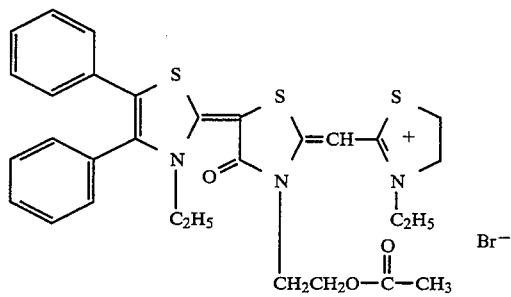
138 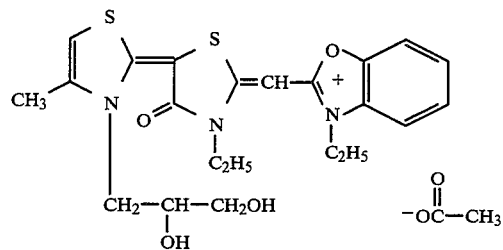
139 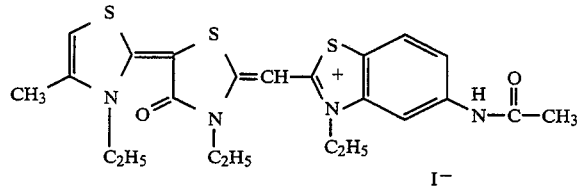
140 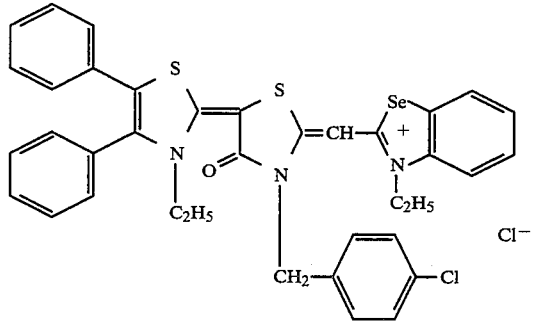
141 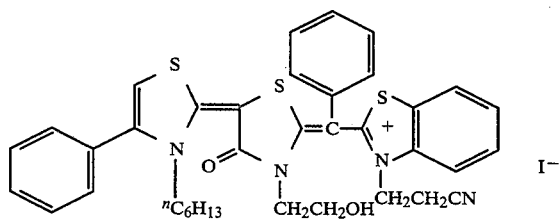
142 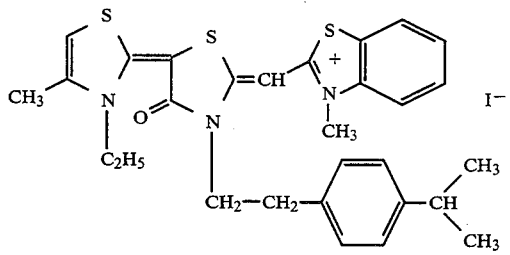

-continued
143
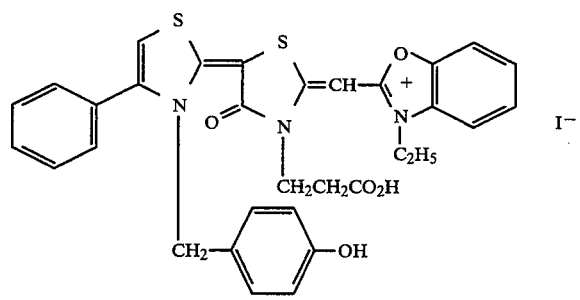
144
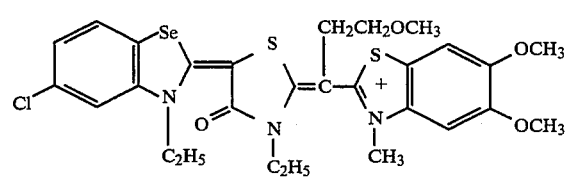
145
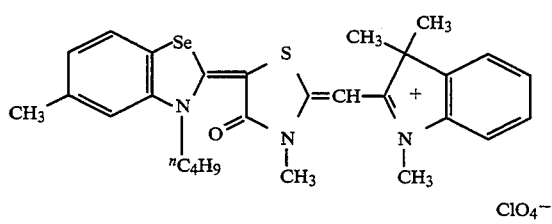
146
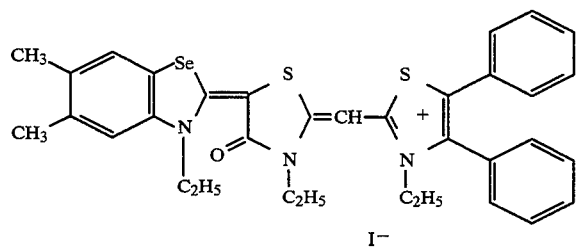
147
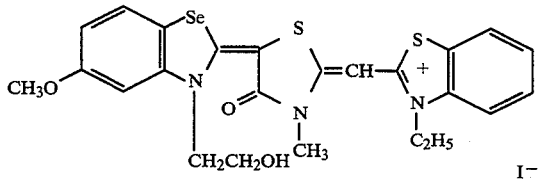
148
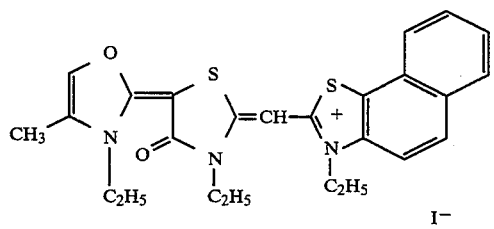
149
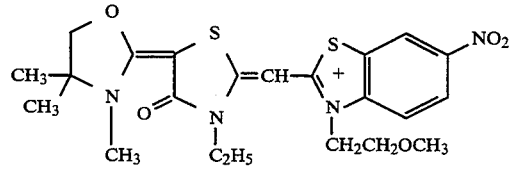

150
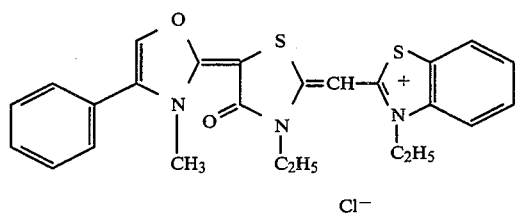
151
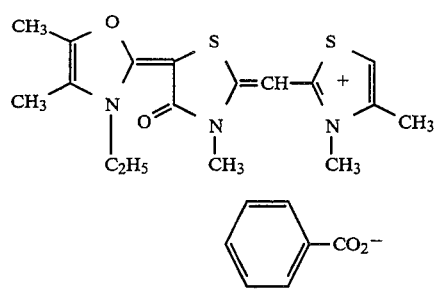
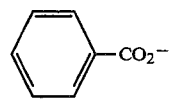
152
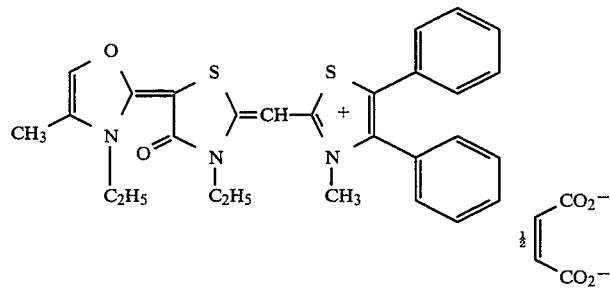
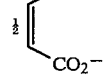
153
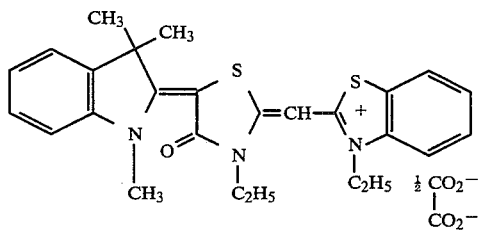
154
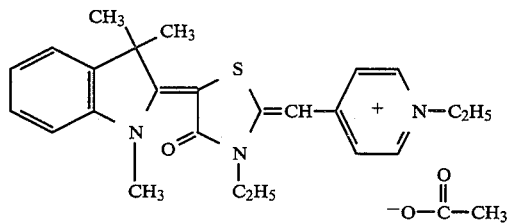
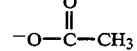
155
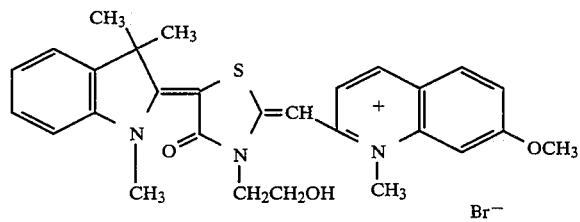

156 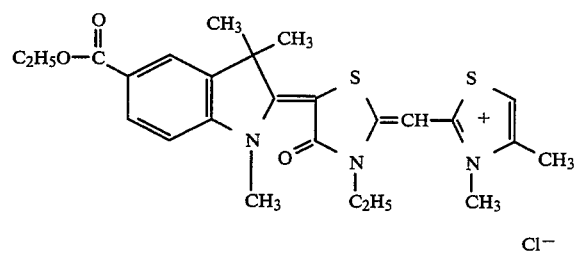
157 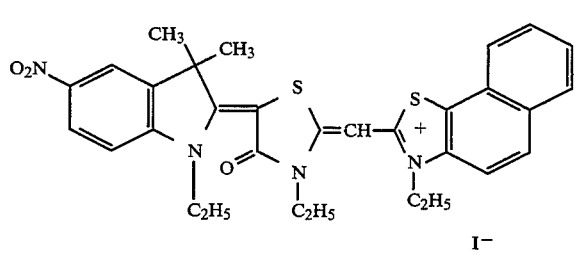
158 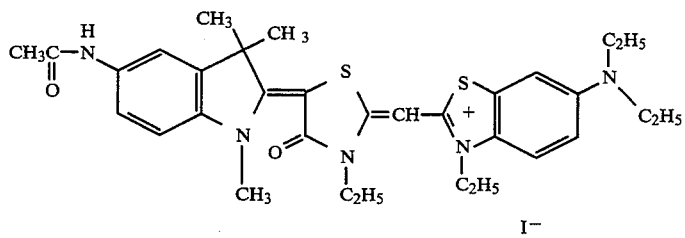
159 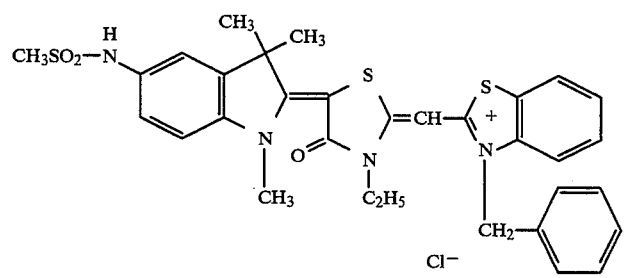
160 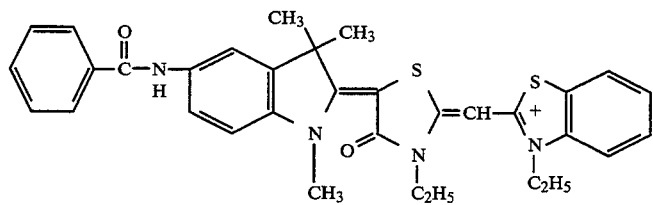
161 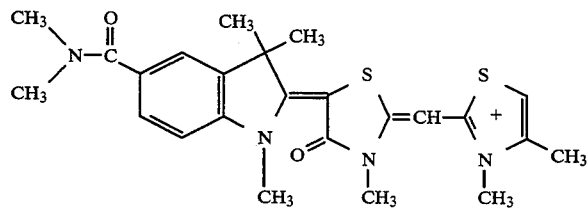

162 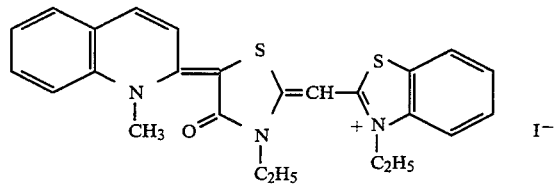
163 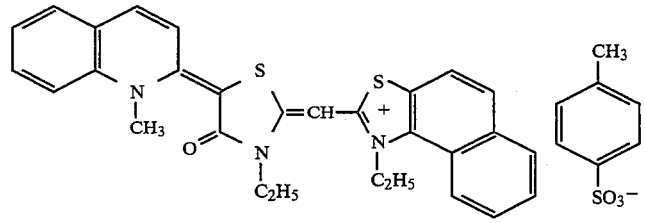
164 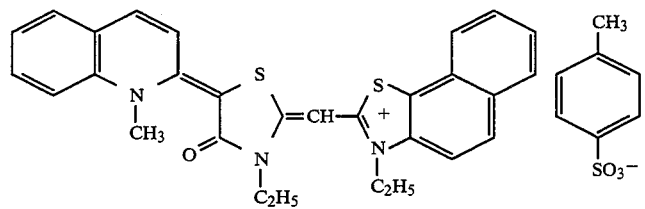
165 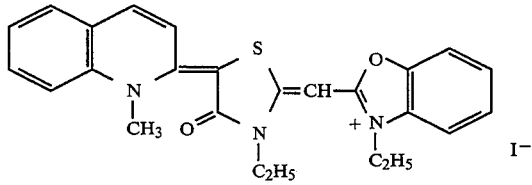
166 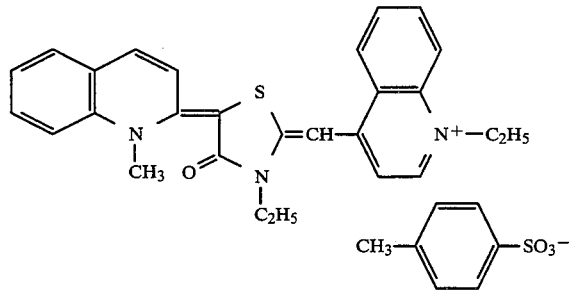
167 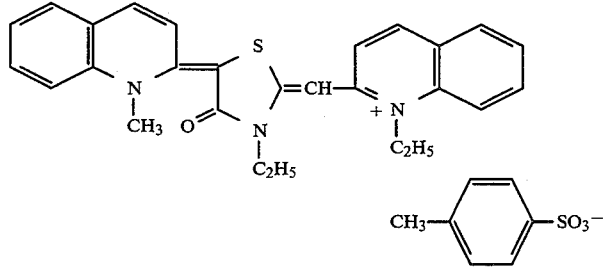

168 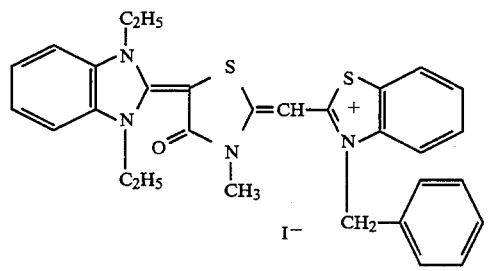
169 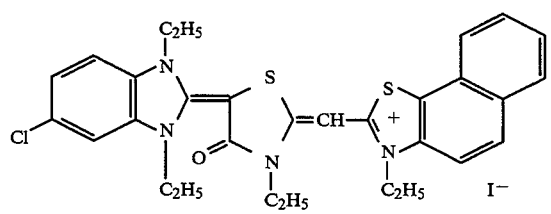
170 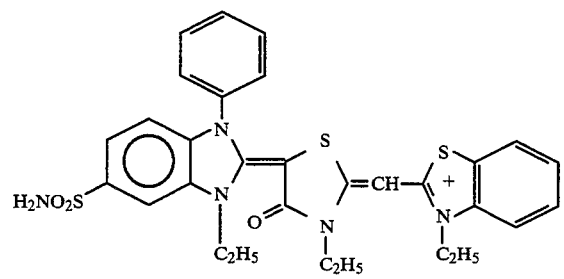
171 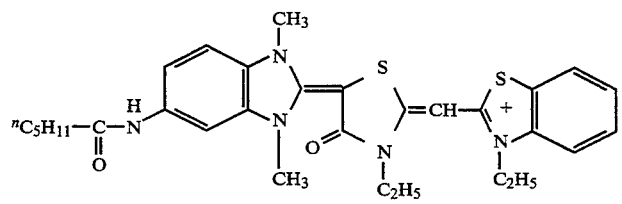
172 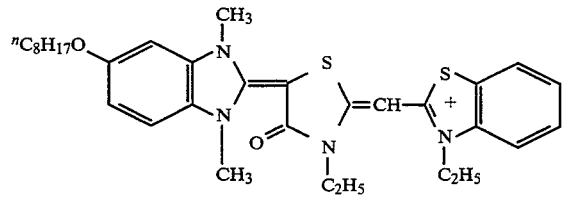
173 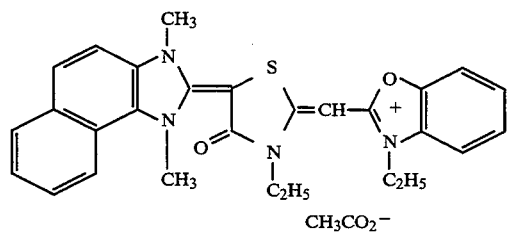

-continued
174 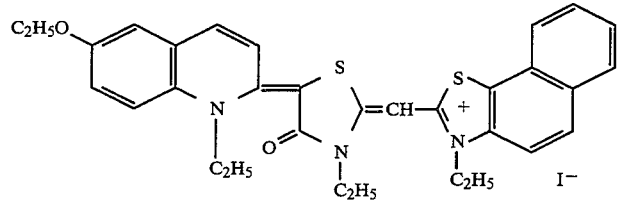
175 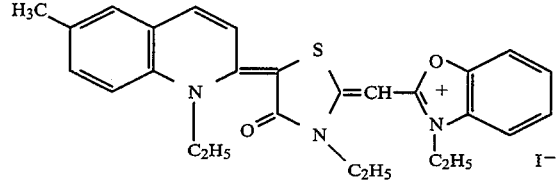
176 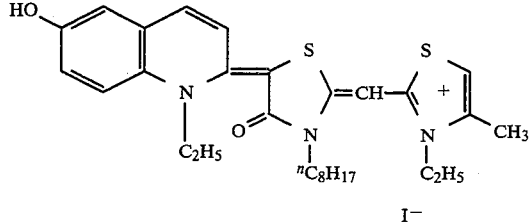
177 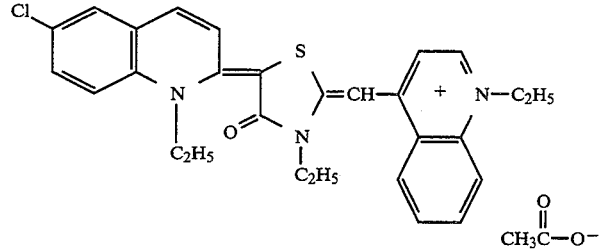
178 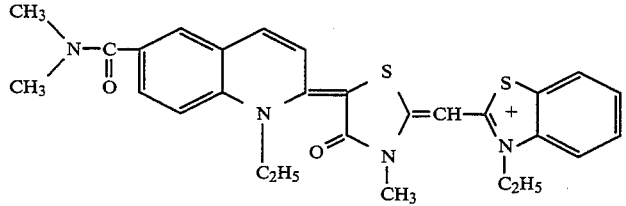
179 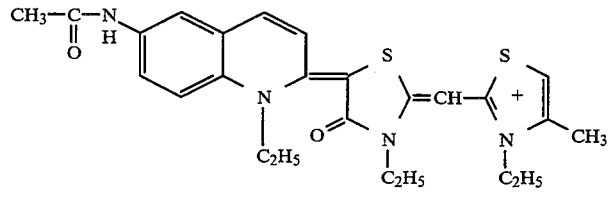

180 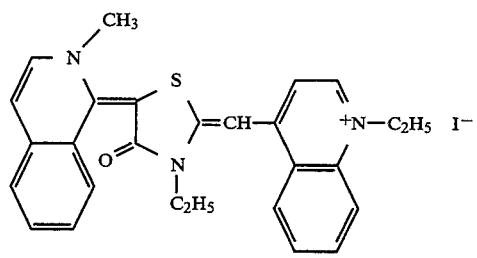
181 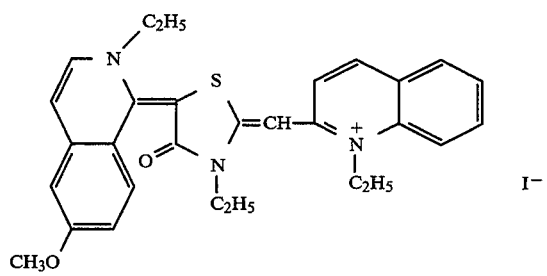
182 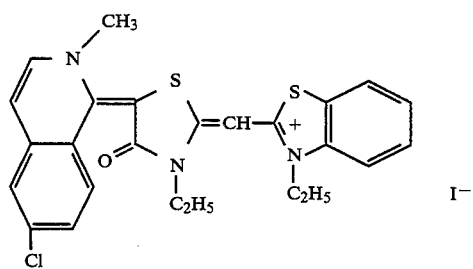
183 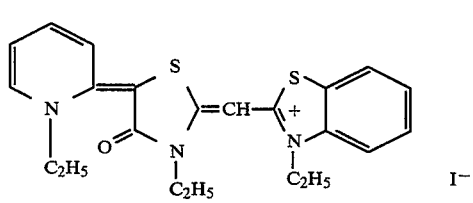
184 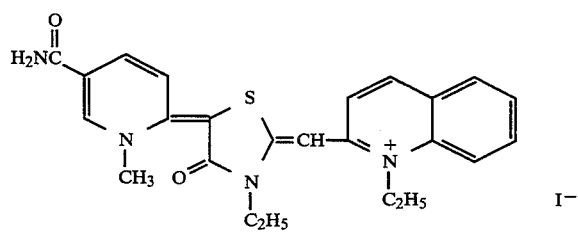
185 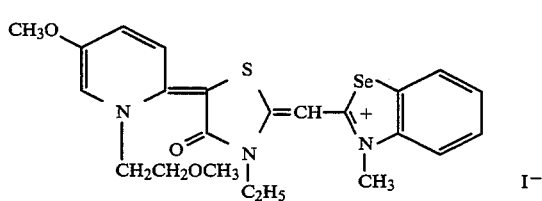
186 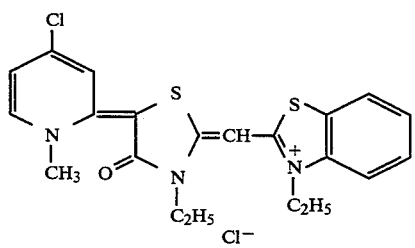

187 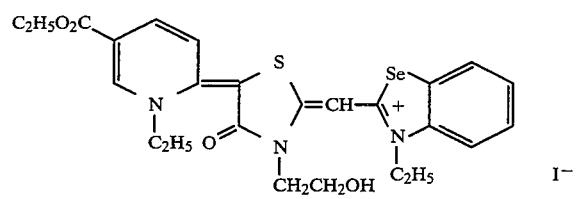
188 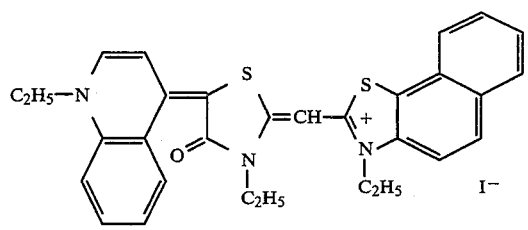
189 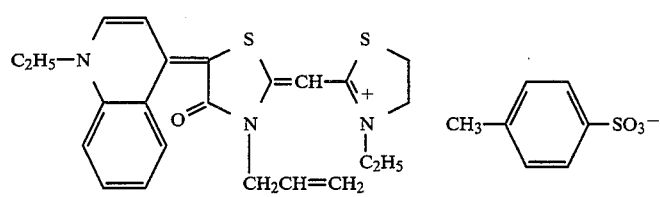
190 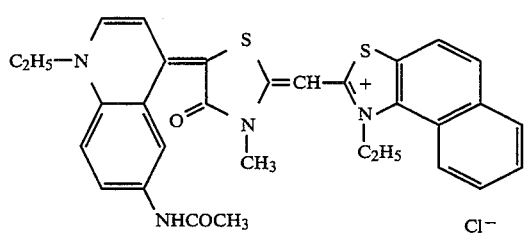
191 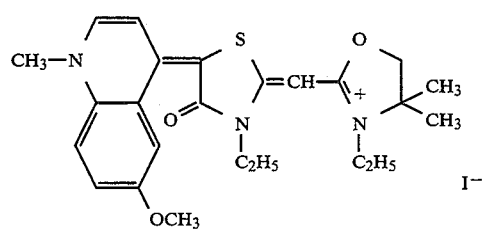
192 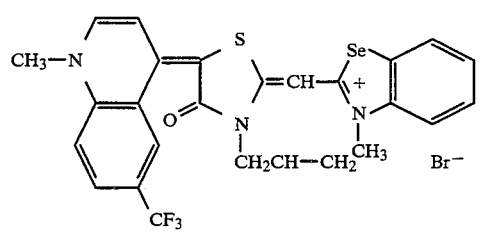
193 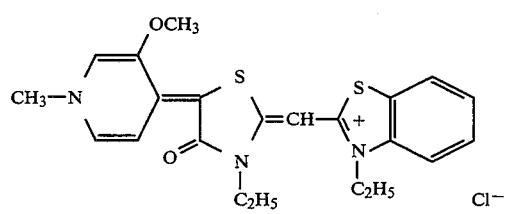

194 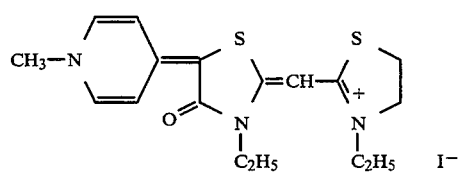
195 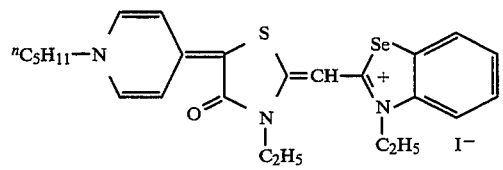
196 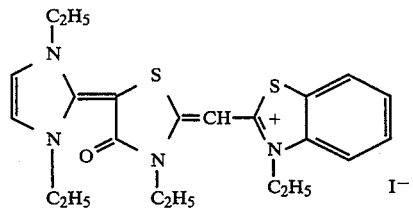
197 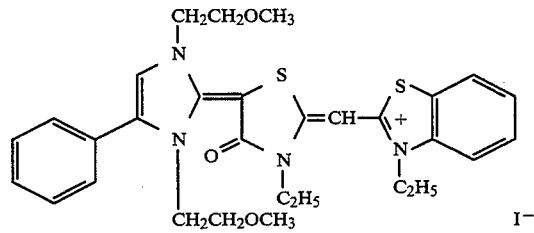
198 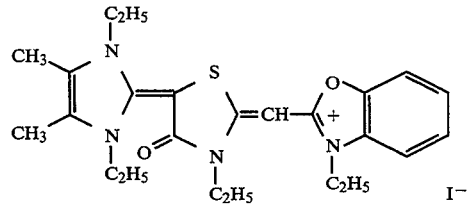
199 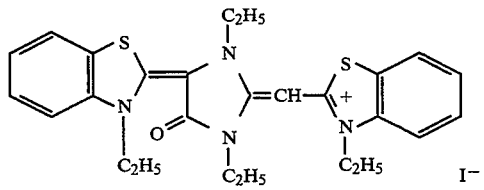
200 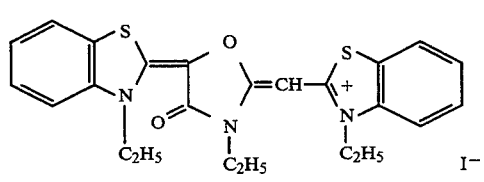
201 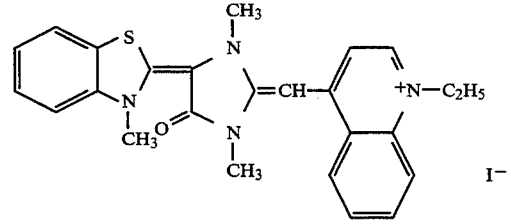

202
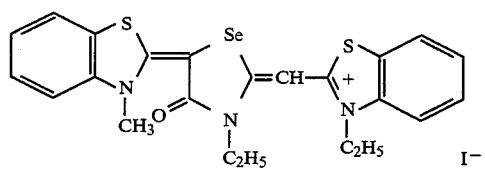
203
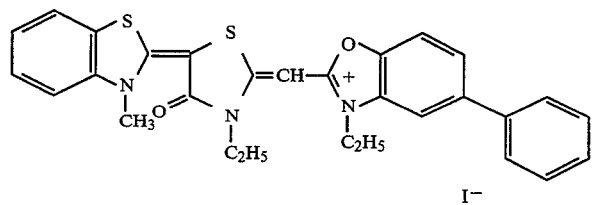
204
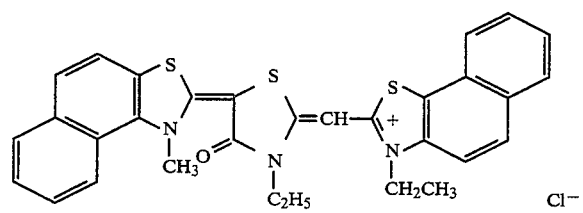
205
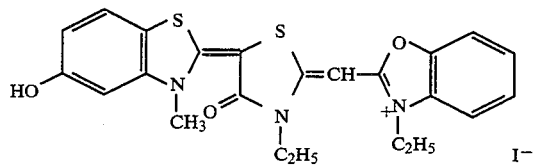
206
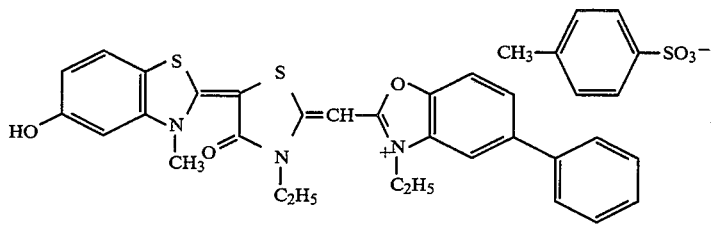
207
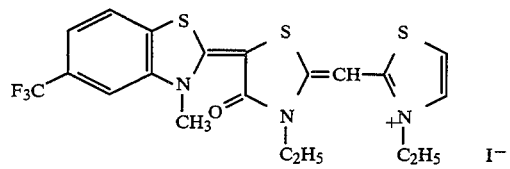
208
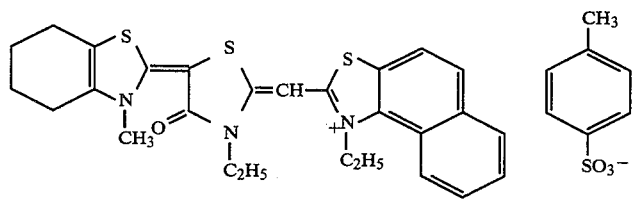

-continued
209
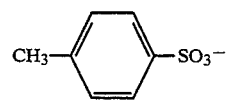
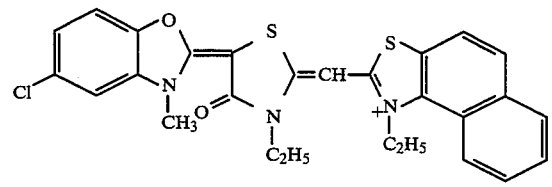
210
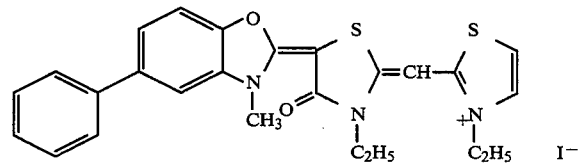
211
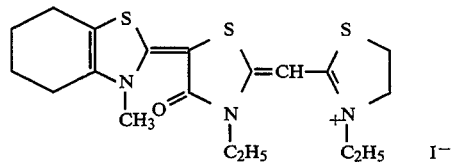
212
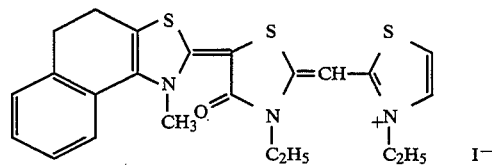
213
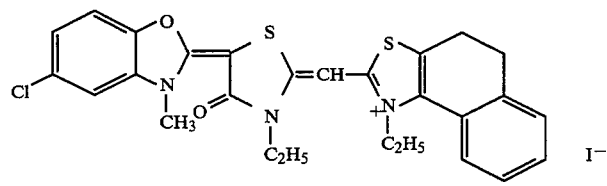
214
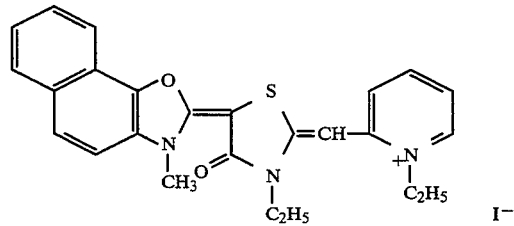
215
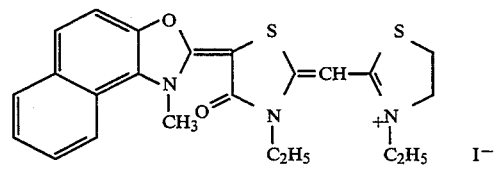

216 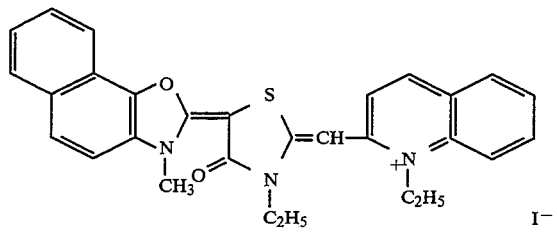
217 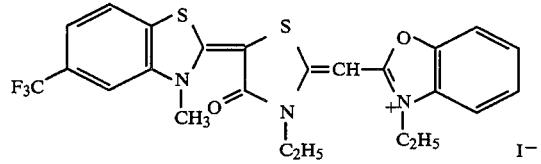
218 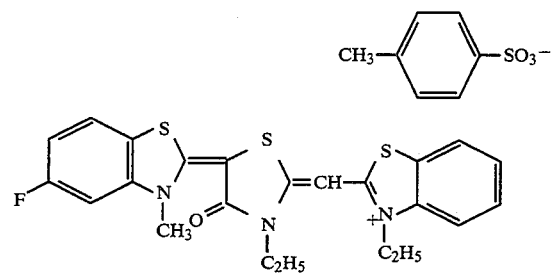
219 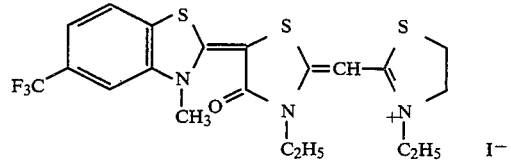
220 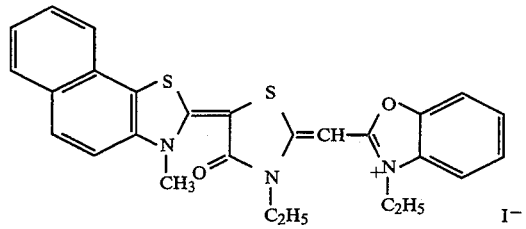
221 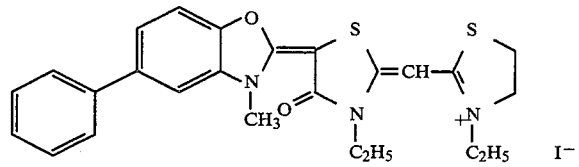
222 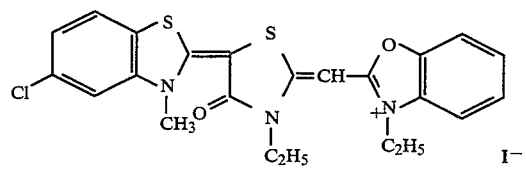

223 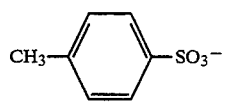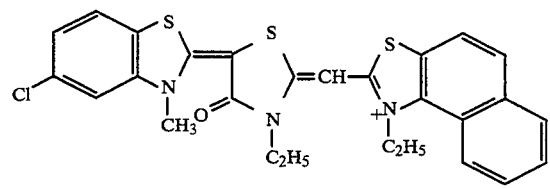
224 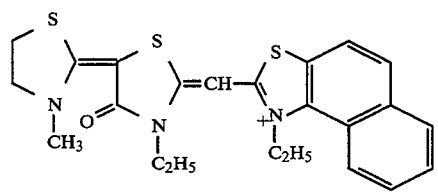
225 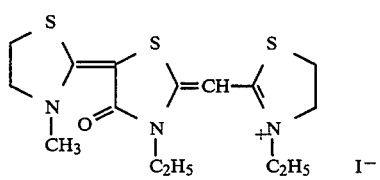
226 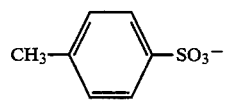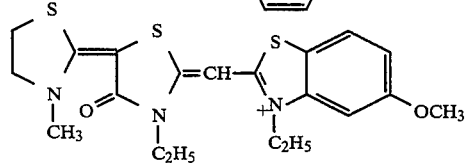
227 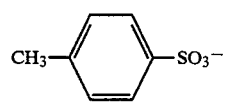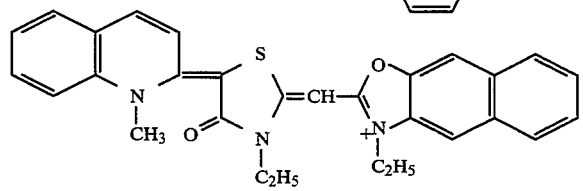
228 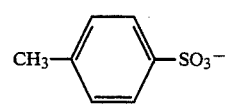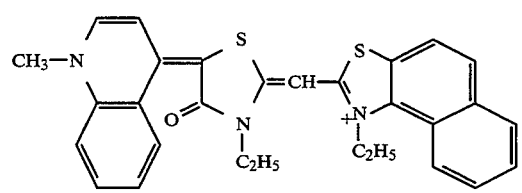

229 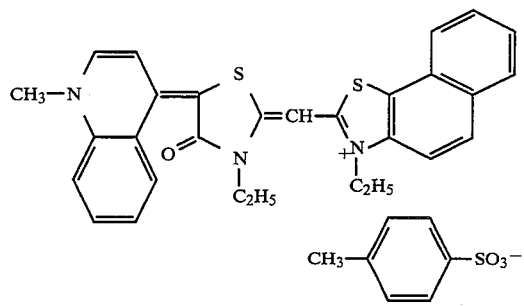
230 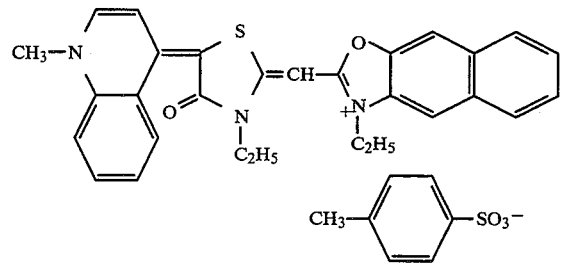
231 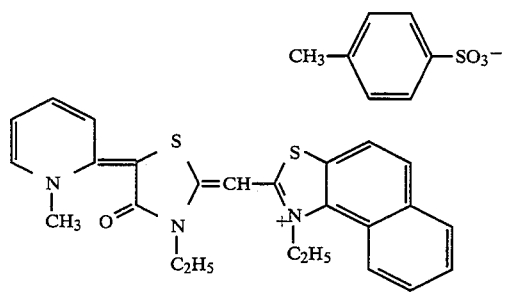
232 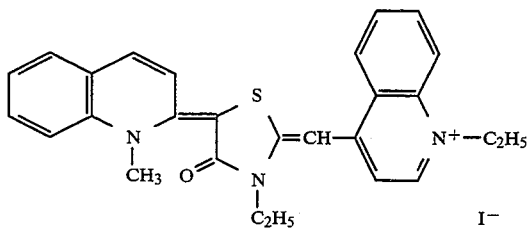
233 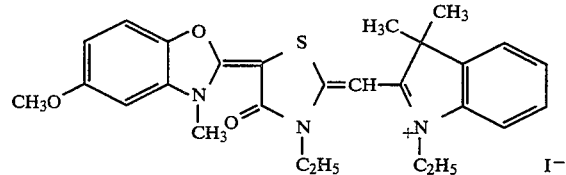
234 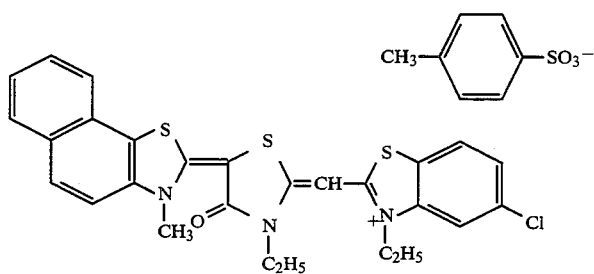

235 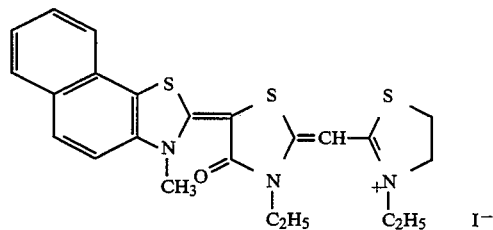
236 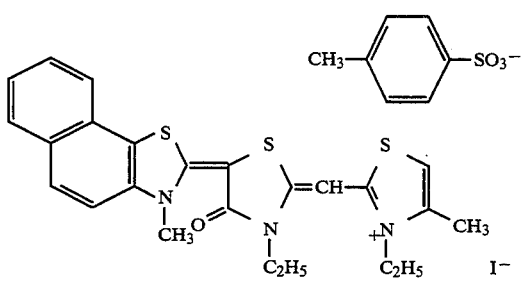
237 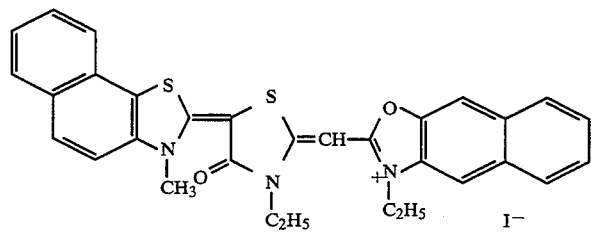
238 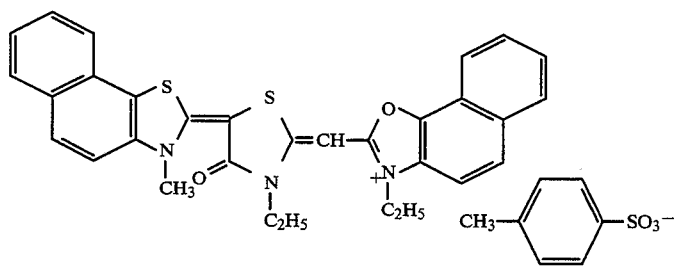
239 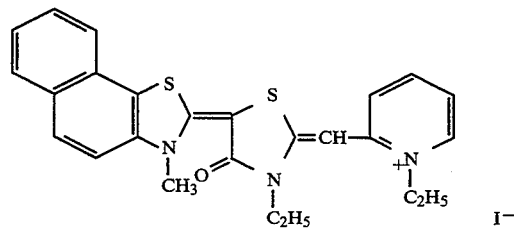
240 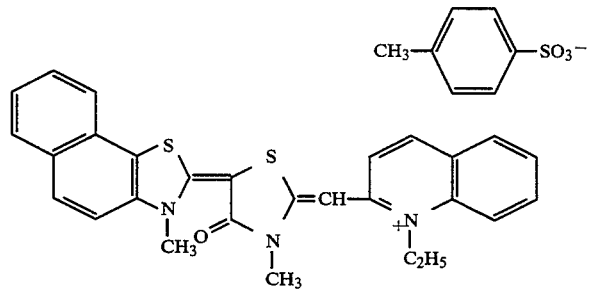

241
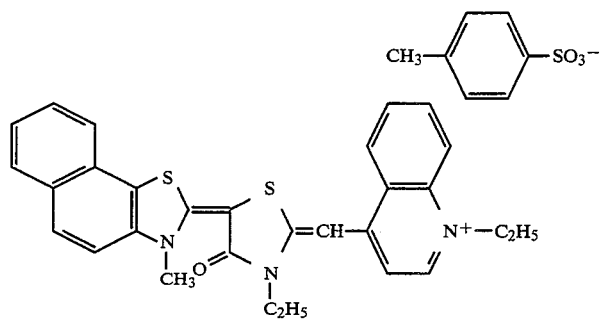
242
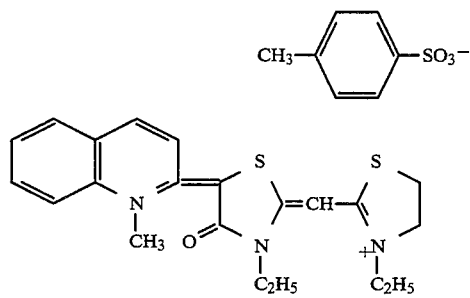
243
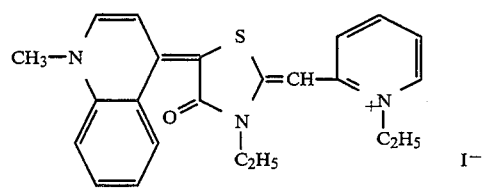
244
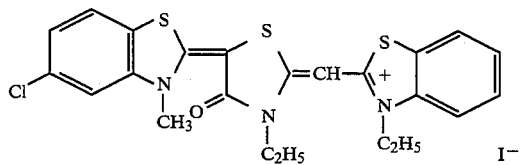
245
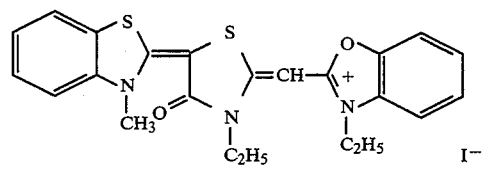
246
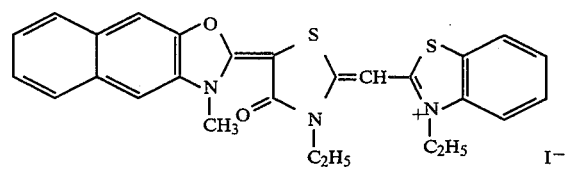
247
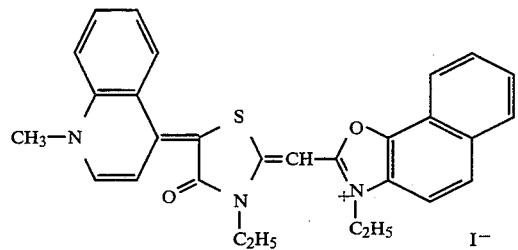

248 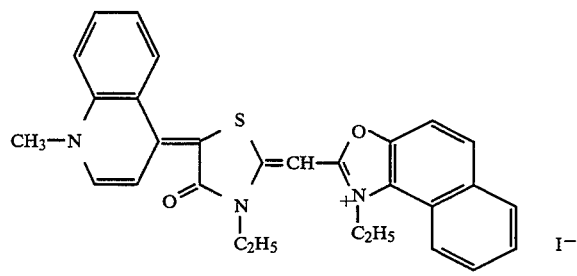
249 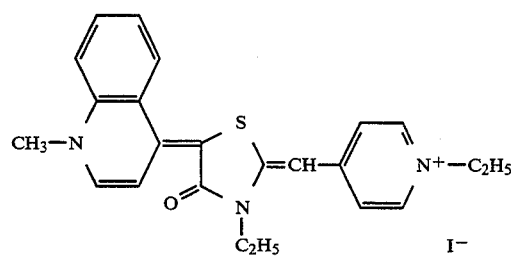
250 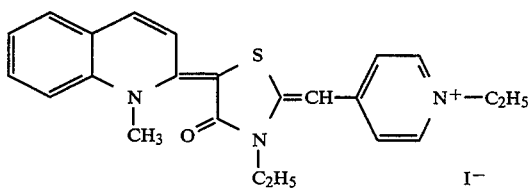
251 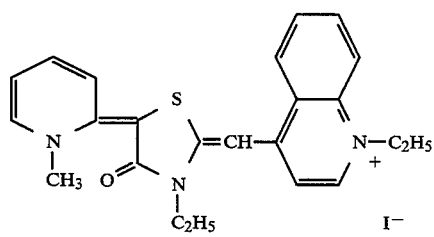
252 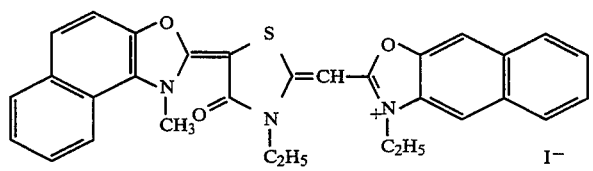
253 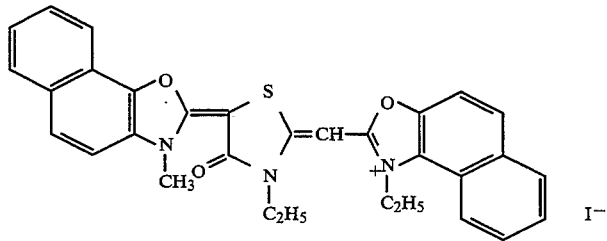
254 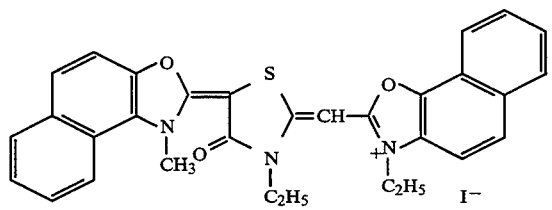

255 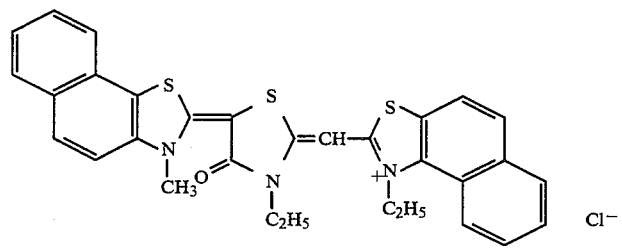
256 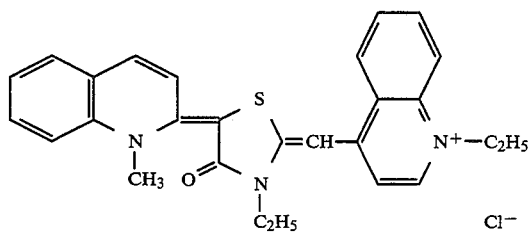
257 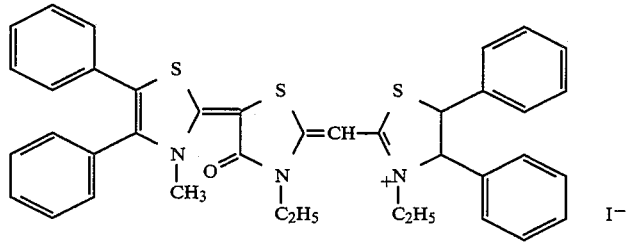
258 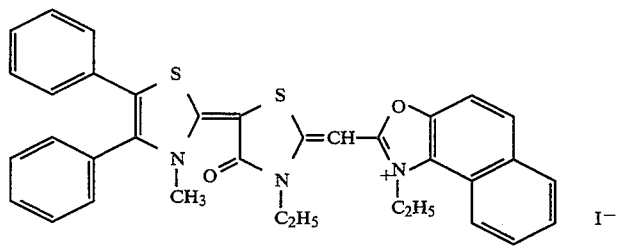
259 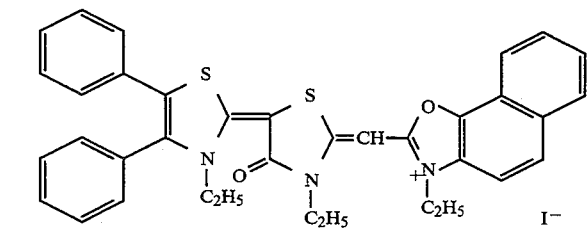
260 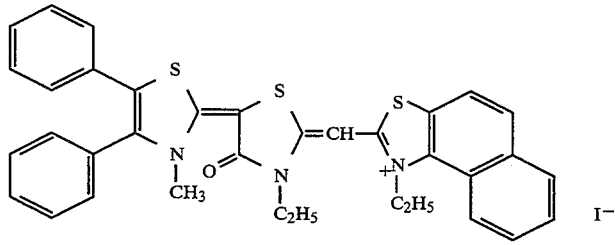

261 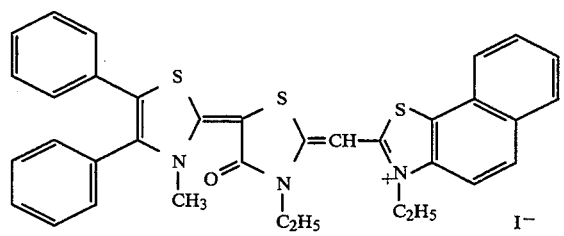
262 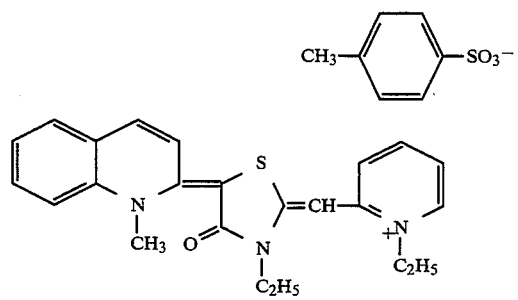
263 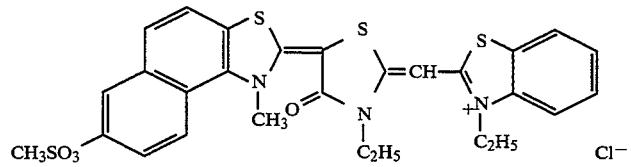
264 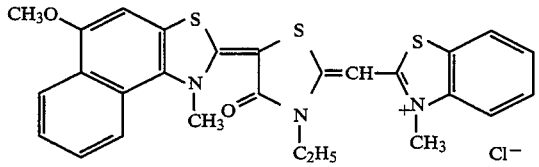
265 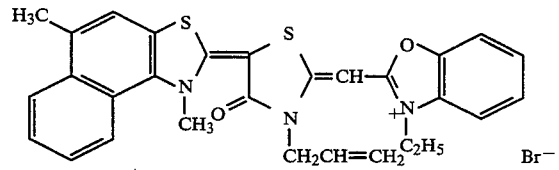
266 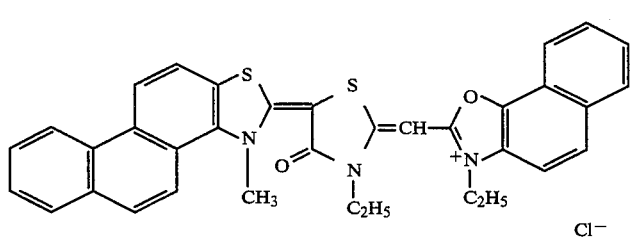
267 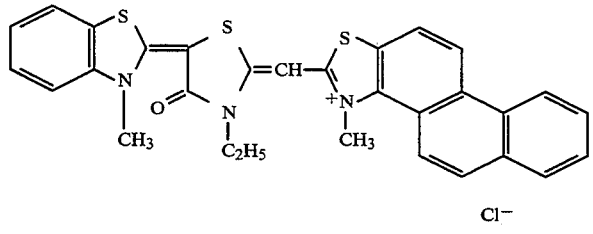

268 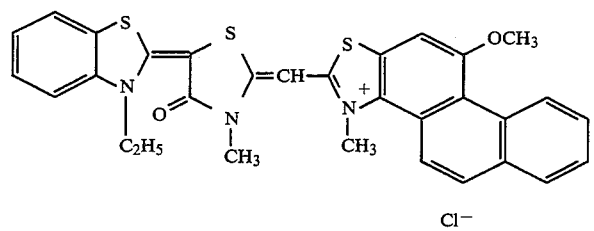
269 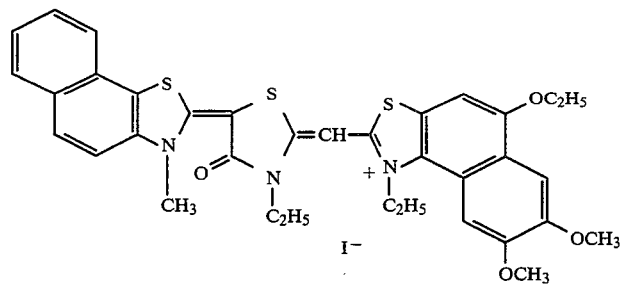
270 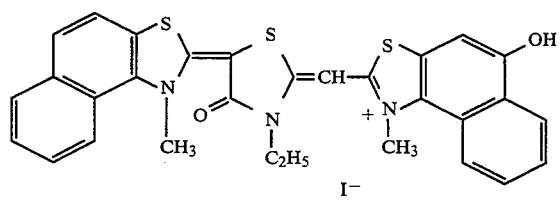
271 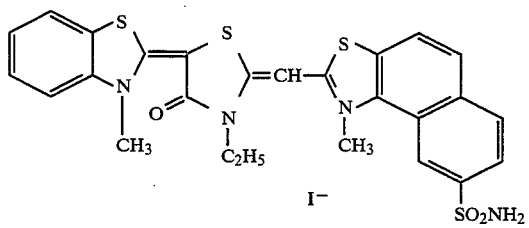
272 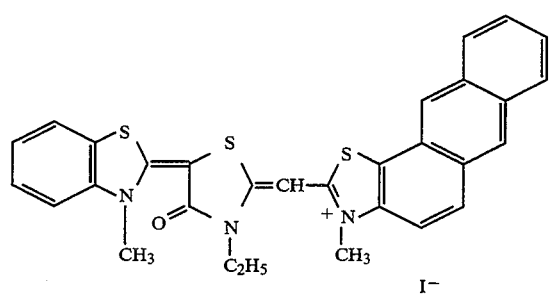
273 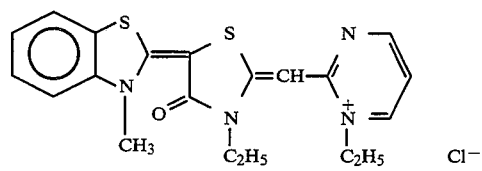
274 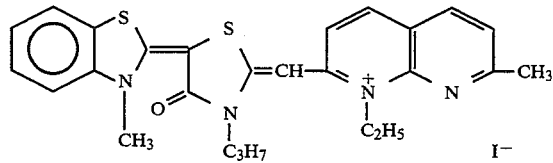

275 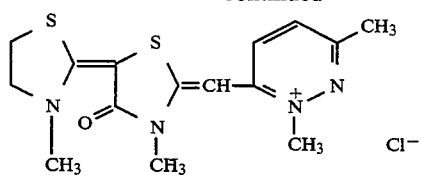
276 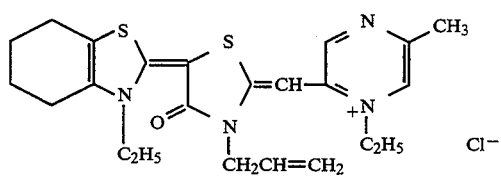
277 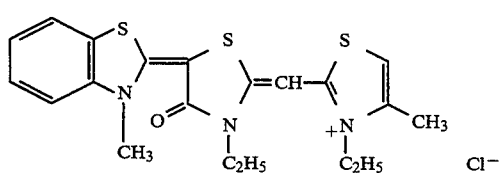
278 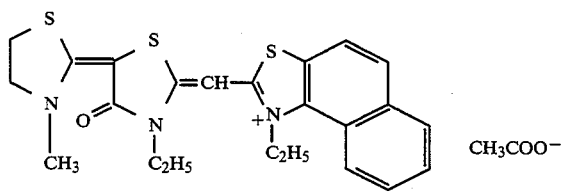
279 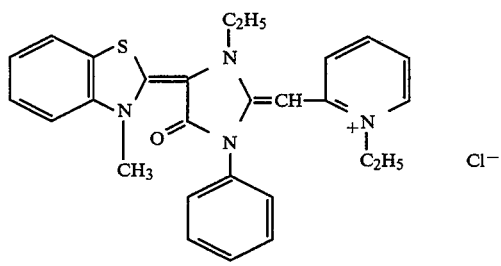
280 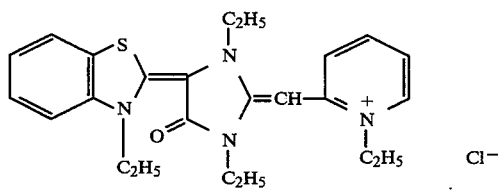
281 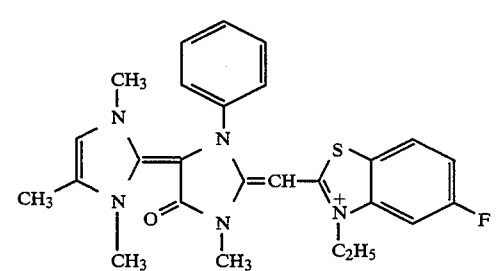
282 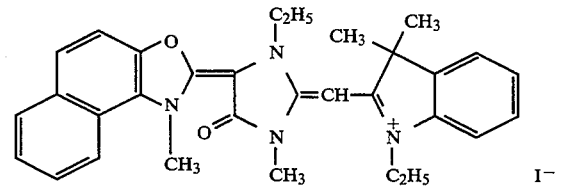

-continued
283
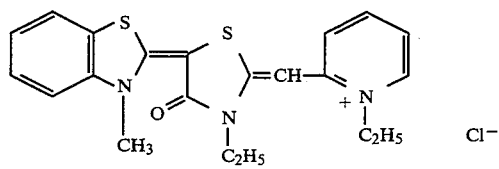
284
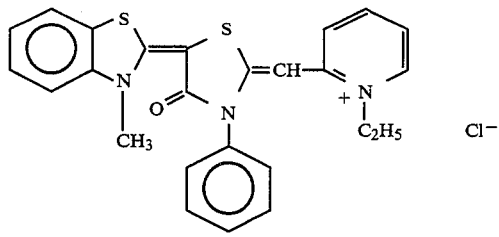
285
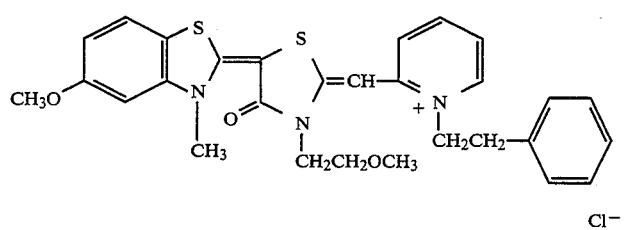
286
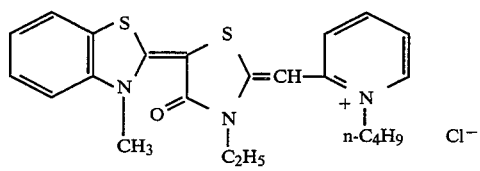
287
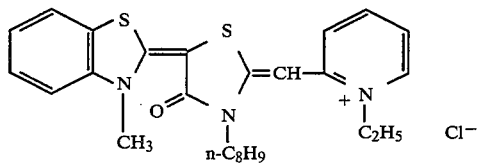
288
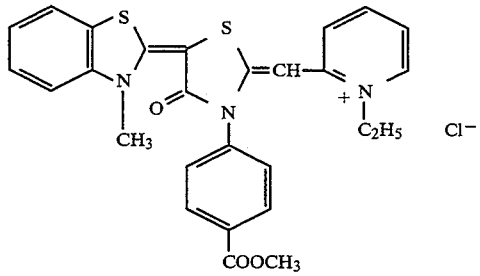
289
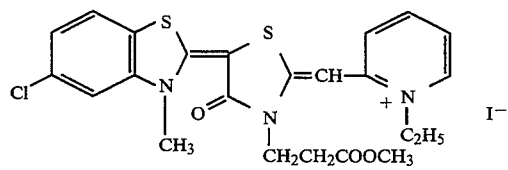

290 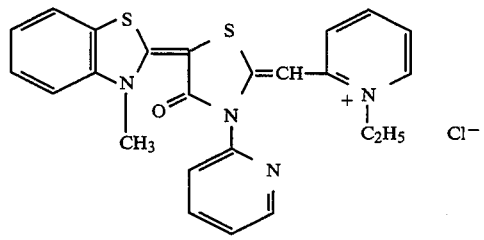
291 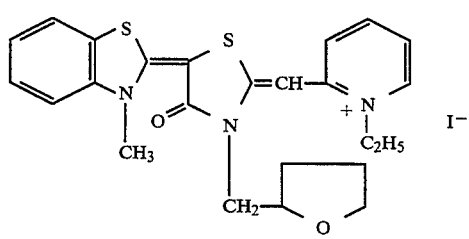
292 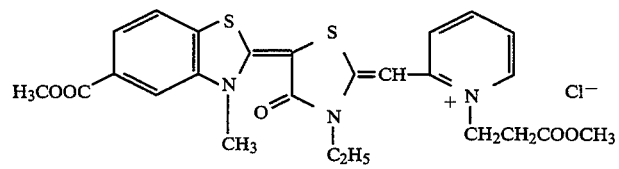
293 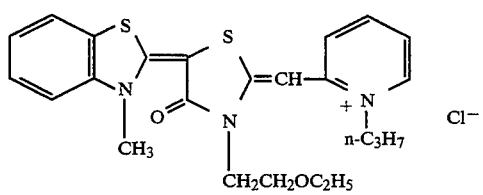
294 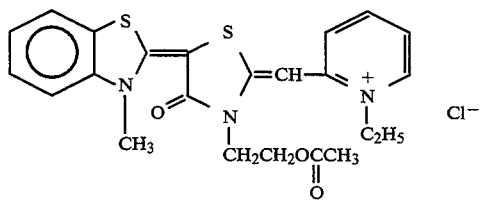
295 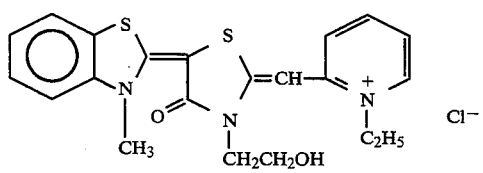
296 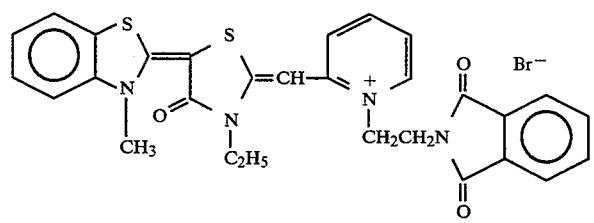

297 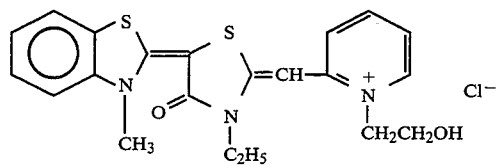
298 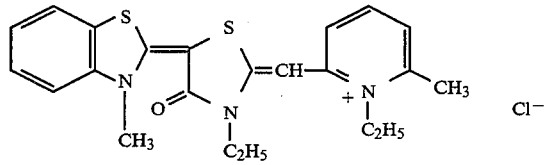
299 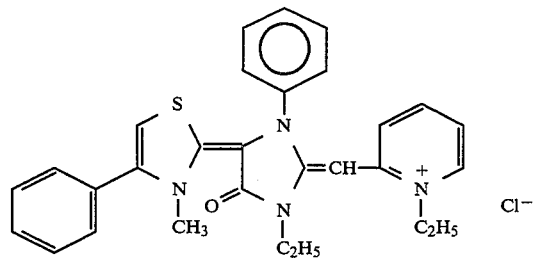
300 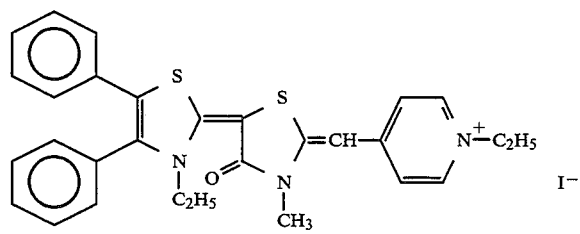
301 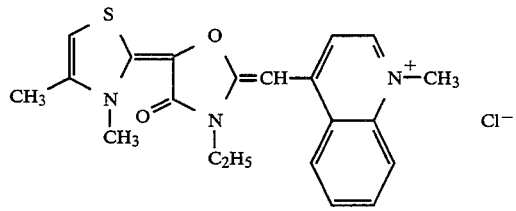
302 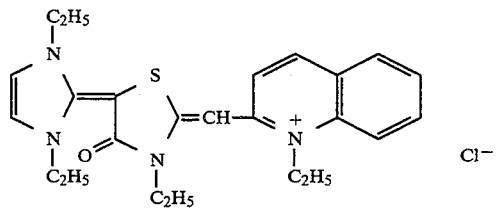
303 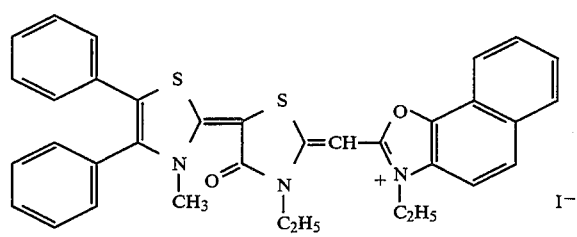

-continued
304
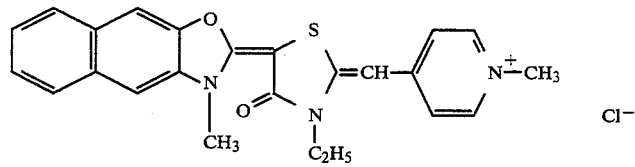
305
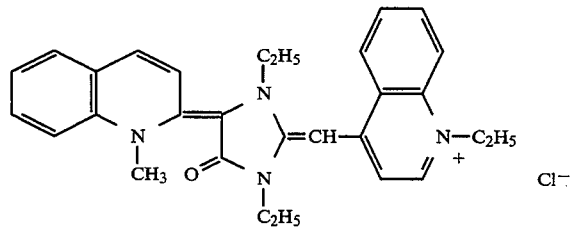
306
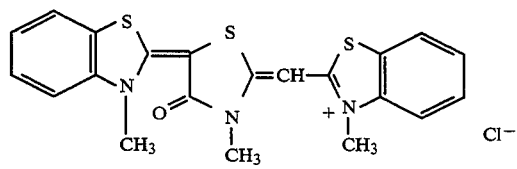
307
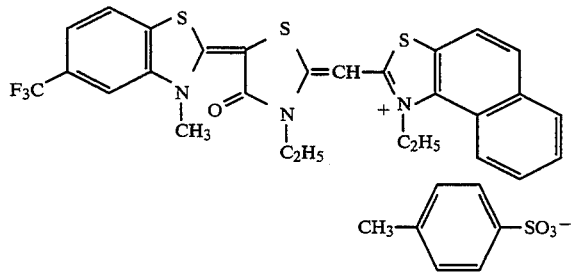
308
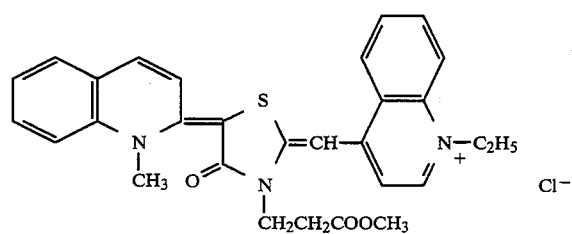
309
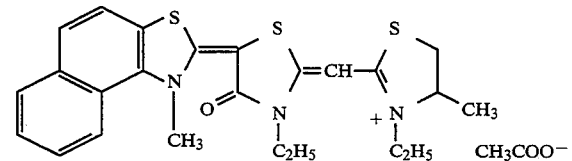
310
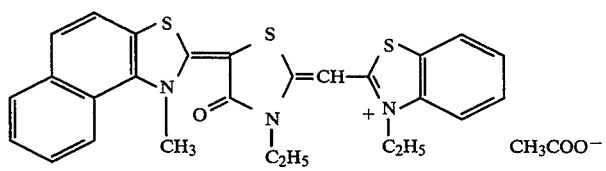

311 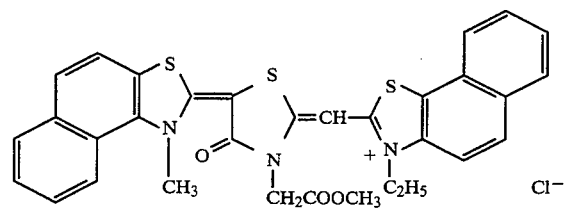
312 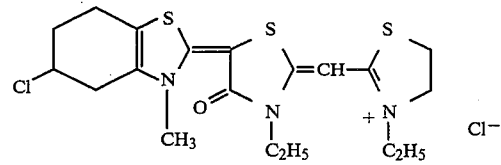
313 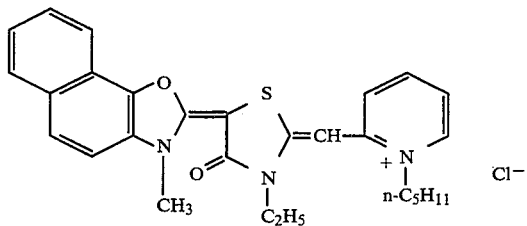
314 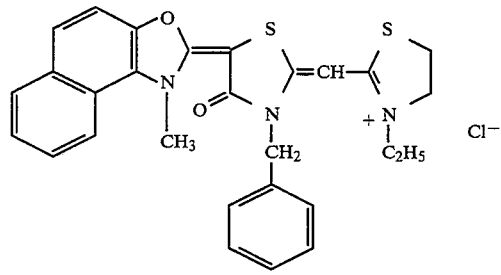
315 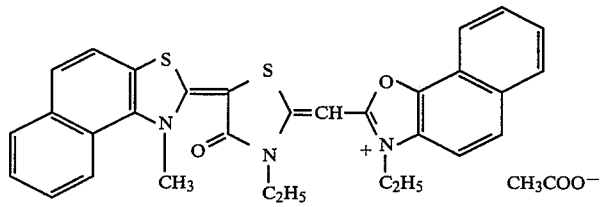
316 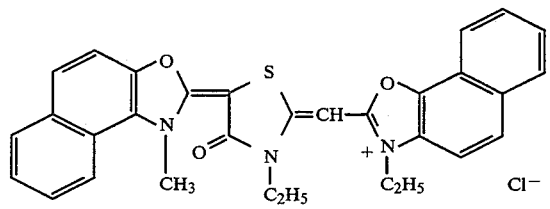
317 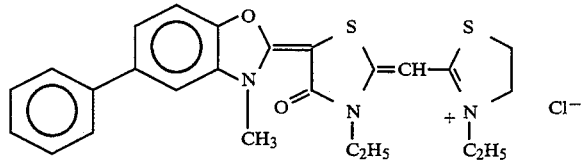

-continued
318 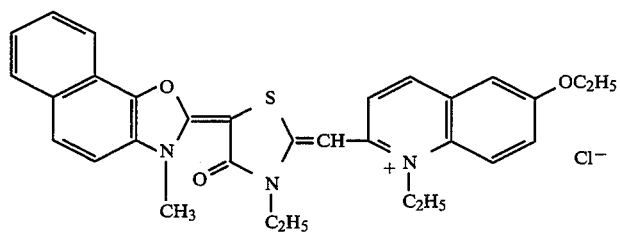
319 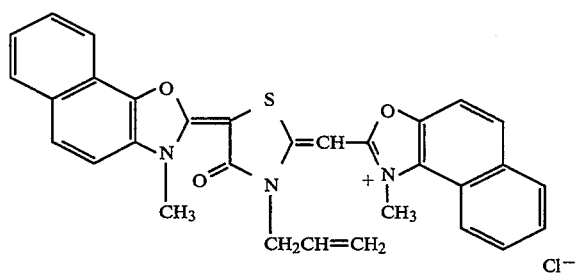
320 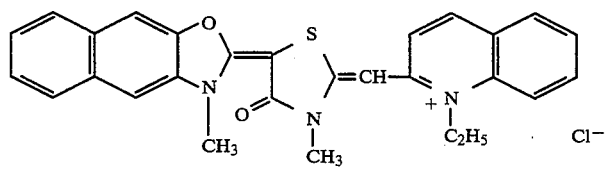
321 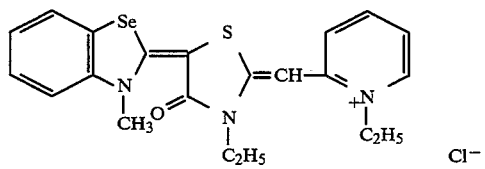
322 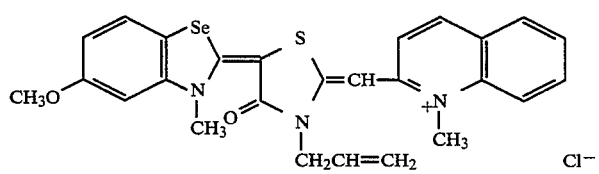
323 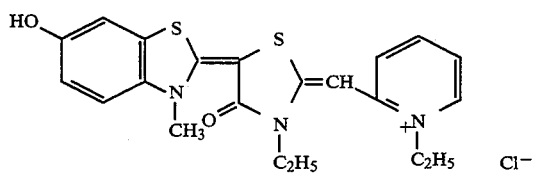
324 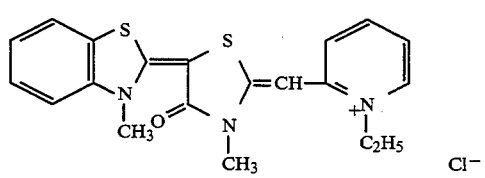
325 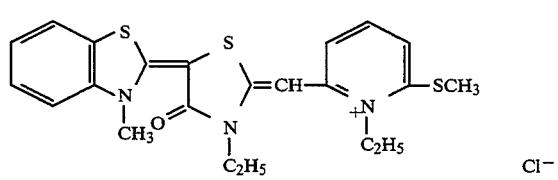

326 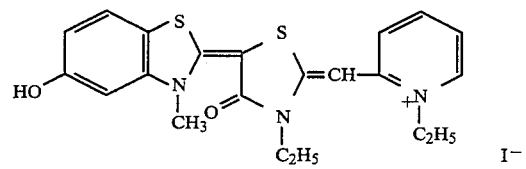
327 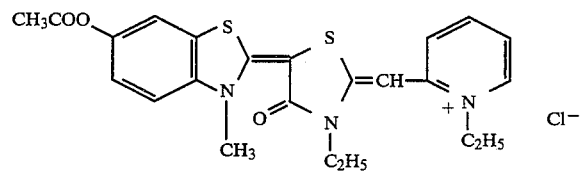
328 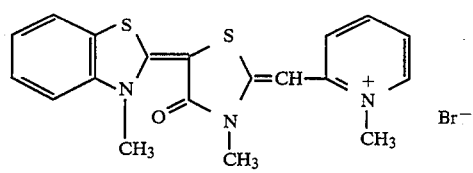
329 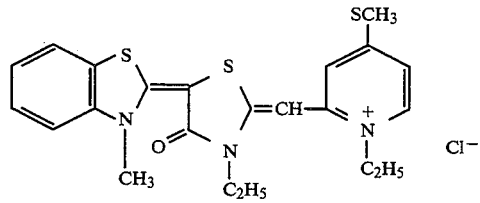
330 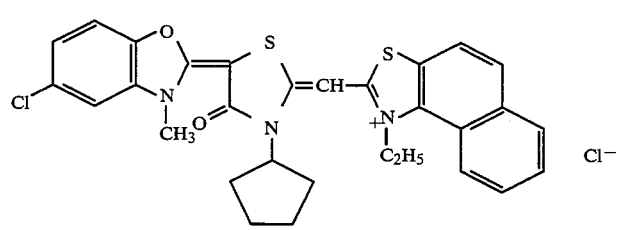
331 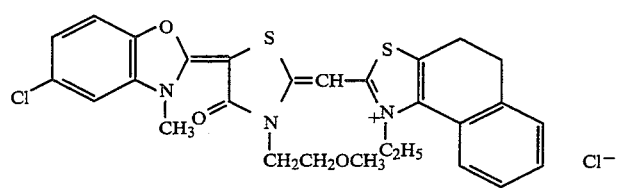
332 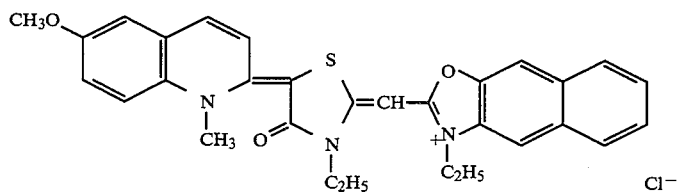
333 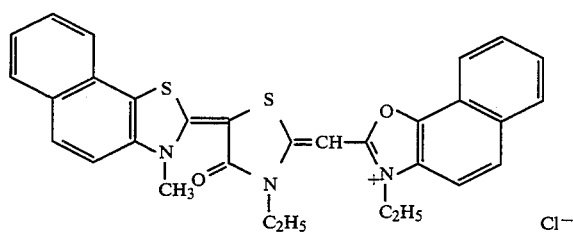

334 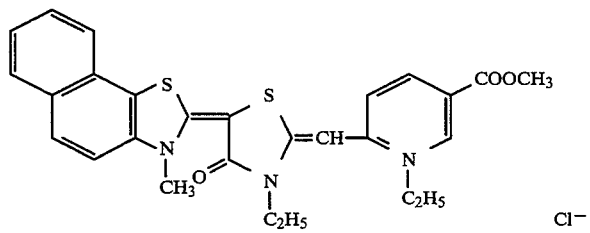
335 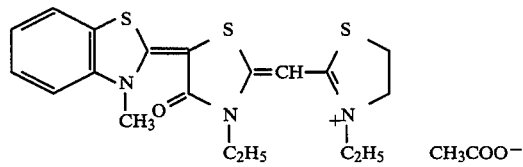
336 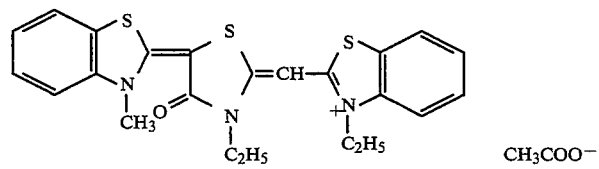
337 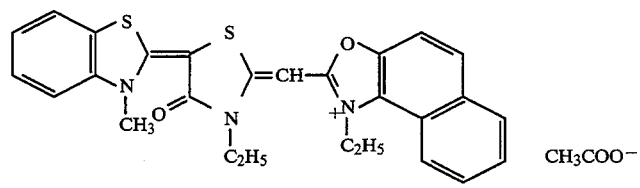
338 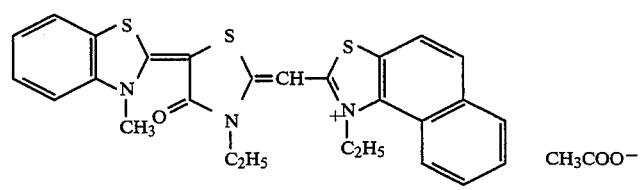
339 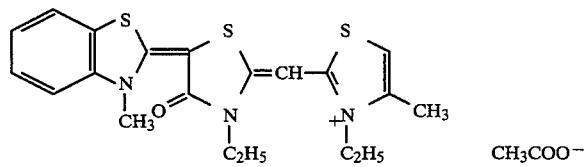
340 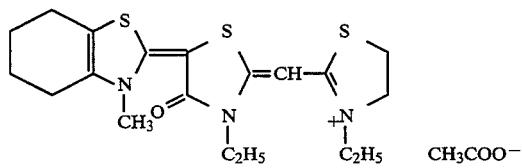
341 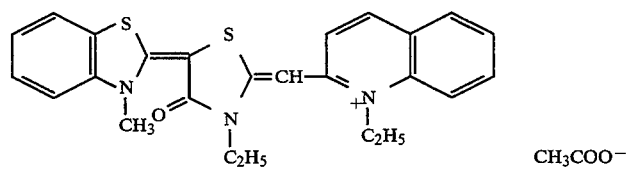

-continued
342 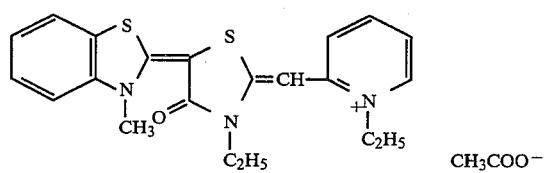
343 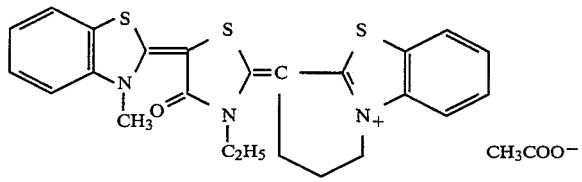
344 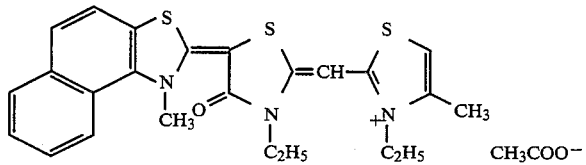
345 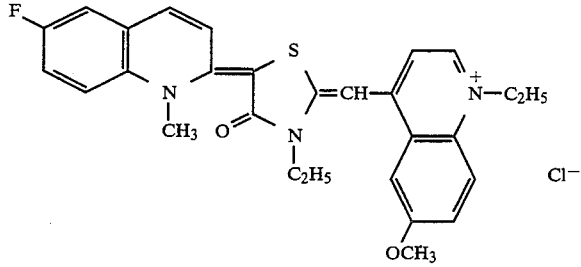
346 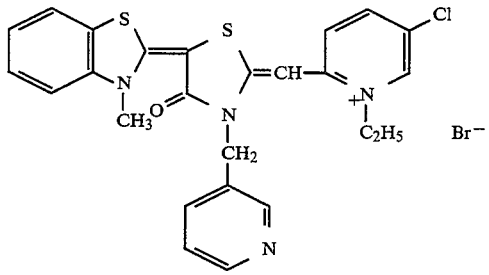
347 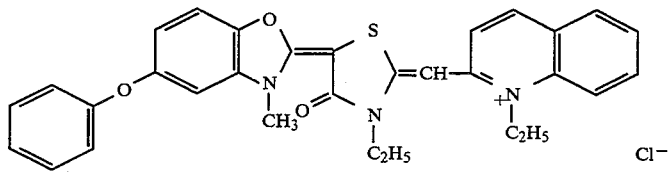
348 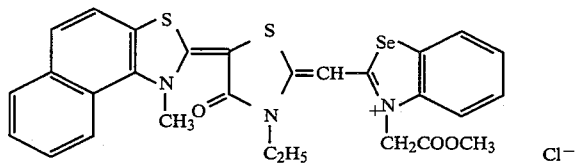
Among those exemplified compounds, particularly preferable compounds are those Nos. 2, 8, 13, 28, 39, 57, 204, 211, 214, 215, 224, 232, 256, 277, 278, 283, 310, 316, 335, 336, 337, 338, 339, 340, 342 and 344.
SYNTHESIS EXAMPLE 1—1 (Compound 34)
29.78 g of 5-[(3-methyl-2(1H)-1,2-dihydrobenzothiazolylidene)-2-methylmercapto-4-thiazolone etho-p-toluenesulfonate and 20 g of 1-ethyl-4-methyl-benzoxazolium p-touluenesulfonate were mixed in 450 cc of acetonitrile.

To the mixture was added 12.5 cc of triethylamine at 40° C. and the mixture was stirred for 1 hour.

Then the mixture was cooled to room temperature and stirred for 1 hour.

The precipitate was filtered off and washed with 200 cc of acetonitrile and dried.

After crystallization from acetonitrile/chloroform (1:1 by volume), the pure product was obtained in a yield of 35% with a melting point of 256° to 258° C. ($\lambda_{max}^{MeOH}$ =485 nm ($\epsilon$=7.54×10$^4$).

SYNTHESIS EXAMPLE 2 (Compound 245)

4 g of Compound 34 was dissolved in 500 ml of methanol-chloroform (1:1 by volume ).

To this solution, 4 g of sodium iodide in 100 ml of methanol was added at room temperature and evaporated to about 300 cc. The precipitate was filtered off and washed with methanol and dried. Compound 245 was obtained in a yield of 82% with a melting point of 272°-274° C. (decomp.) $\lambda_{max}^{MeOH}$ =485 nm ($\epsilon$=7.98×10$^4$).

SYNTHESIS EXAMPLE 3 (compound 28)

(a) Method Using Silver Acetate:

2.0 g of Compound 245 was dissolved in 800 ml of methanol and 200 ml of chloroform with heating, and the solution was once filtered. 2 g of silver acetate was added to the filtrate, and the mixture was stirred at room temperature for 2 hours. After the reaction mixture was filtered, one gram of silver acetate was added to the filtrate and the mixture was stirred at room temperature for 1 hour. After filtration, the solvents in the filtrate were distilled off at 40° C. or lower under reduced pressure. 200 ml of ethyl acetate was added to the residue. The formed crystals were crushed and the mixture was stirred. The formed crystals were recovered by filtration and dissolved in 200 ml of methanol. The solution was filtered through Celite (Celite 545, a commercially available diatomaceous earth from Manville Sales Corp.). The filtrate was concentrated under reduced pressure to about 1/5 volume. Ethyl acetate was added to the concentrate to precipitate crystals. The crystals were recovered by filtration, washed with ethyl acetate and dried to obtain 1.4 g of a yellow solid. Yield: 80%. M.P.: 140°-145° C. ($\lambda_{max}^{MeOH}$=485 nm ($\epsilon$=7.19×10$^4$).

(b) Method Using ion-Exchange Resin;

250 g of an ion-exchange resin (DIAION WA-21, produced by Mitsubishi Chemical Ind. Ltd.) was packed in a column and treated with 2.5 l of 1N-sodium hydroxide/methanol solution and then treated with 1.5 l of 1N-acetic acid/methanol solution.

7 g of Compound 34 in 0.5 l of 1N-acetic acid/methanol solution was passed through the column described above.

Compound 28 was eluted with the solution of 1N-acetic acid/methanol solution and the diluent was concentrated to about 100 ml under reduced pressure and to this residue, 0.71 of ethyl acetate was added. The product precipitated was collected by suction filtration and washed with ethyl acetate. After drying, 5.0 g of pure Compound 28 was obtained in a yield of 87%.

The melting point and $\lambda_{max}^{MeOH}$($\epsilon_{max}$) were the same as described in (a) above.

SYNTHESIS EXAMPLE 4 (compound 82)

40.0 g of 5-[(3-methyl-2(3H)-2,3-dihydronaphtho[1,2-d]thiazolylidene]-2-methylmercapto-4-thiazolone etho-p-toluenesulfonate and 29.3 g of 3-ethyl-2-methylnaphtho(2,1-d) thiazolium p-toluenesulfonate were mixed in 1600 cc of acetonitrile.

To the mixture was added 40.9 cc of triethylamine at 40° C. and stirred for 2 hours.

Then the mixture was cooled to room temperature and stirred for 1 hour.

The precipitate was filtered off and washed with 200 cc of acetonitrile and dried.

After crystallization from methanol/chloroform (1:1 by volume), the pure product was obtained in a yield of 62% with a melting point of 256° to 258 ° C. $\lambda_{max}^{MeOH}$ =525 nm ($\epsilon$=7.16×10$^4$).

SYNTHESIS EXAMPLE 5 (Compound 204)

250 g of an ion-exchange resin (AMBERLYST A-26, produced by Rhom & Haas, Inc.) was packed in a column and then a solution of 7.2 g of Compound 82 in 1000 ml of methanol-chloroform (1:1 by volume) was passed through this column.

Compound 204 was eluted with 1 l of methanol and the eluent was concentrated to about 200 ml. To this residue, 500 ml of ethyl acetate was added and then the mixture was reconcentrated to about 500 ml.

The product precipitated was collected by suction filtration and washed with ethyl acetate. After drying, 5.3 g of pure Compound 204 was obtained in a yield of 90% and with a melting point of 224°-232° C. $\lambda_{max\text{-}MeOH}$=525 nm ($\epsilon$=6.25×10$^4$).

Other compounds of the General Formulas (I) to (V) useful in this invention were easily synthesized using procedures similar to those above described. These compounds are shown in Table II below along with their absorption maximum and coefficient of absorption maximum.

TABLE II

| Compound No. | $\epsilon_{max}^{MeOH*}$ | $\lambda_{max}$ nm$^{MeOH}$ |
|---|---|---|
| 1 | 7.03 | 486 |
| 2 | 7.49 | 500 |
| 3 | 7.50 | 485 |
| 4 | 7.29 | 508 |
| 5 | 7.20 | 500 |
| 6 | 6.88 | 502 |
| 7 | 6.83 | 501 |
| 8 | 7.41 | 484 |
| 9 | 7.65 | 484 |
| 10 | 7.68 | 484 |
| 11 | 7.73 | 484 |
| 12 | 7.80 | 483 |
| 13 | 6.85 | 483 |
| 14 | 7.34 | 483 |
| 15 | 7.58 | 483 |
| 16 | 5.90 | 473 |
| 17 | 5.67 | 516 |
| 18 | 4.54 | 495 |
| 19 | 7.67 | 485 |
| 20 | 5.07 | 548 |
| 21 | 5.18 | 548 |
| 22 | 8.29 | 498 |
| 23 | 6.85 | 509 |
| 24 | 6.44 | 567 |
| 25 | 7.30 | 485 |
| 26 | 7.57 | 485 |
| 27 | 7.50 | 504 |
| 28 | 7.19 | 485 |
| 29 | 6.47 | 517 |
| 30 | 9.15 | 510 |
| 31 | 7.88 | 511 |
| 32 | 7.28 | 482 |

TABLE II-continued

| Compound No. | $\epsilon_{max}^{MeOH*}$ | $\lambda_{max\ nm}^{MeOH}$ |
|---|---|---|
| 33 | 6.55 | 500 |
| 34 | 7.54 | 485 |
| 35 | 8.02 | 489 |
| 36 | 7.66 | 489 |
| 37 | 7.32 | 492 |
| 38 | 7.00 | 484 |
| 39 | 5.60 | 525 |
| 40 | 7.79 | 505 |
| 41 | 7.08 | 482 |
| 42 | 6.78 | 488 |
| 43 | 6.73 | 488 |
| 44 | 5.78 | 528 |
| 45 | 5.36 | 590 |
| 46 | 6.96 | 483 |
| 47 | 7.40 | 508 |
| 48 | 5.88 | 518 |
| 49 | 8.50 | 495 |
| 50 | 7.38 | 504 |
| 51 | 7.23 | 510 |
| 52 | 8.11 | 508 |
| 53 | 7.54 | 516 |
| 54 | 8.01 | 510 |
| 55 | 7.57 | 495 |
| 56 | 7.17 | 502 |
| 57 | 6.52 | 485 |
| 58 | 6.72 | 486 |
| 59 | 6.90 | 450 |
| 60 | 6.37 | 574 |
| 61 | 6.52 | 564 |
| 62 | 6.43 | 521 |
| 63 | 7.55 | 503 |
| 64 | 7.89 | 484 |
| 65 | 5.73 | 480 |
| 66 | 8.19 | 518 |
| 67 | 4.96 | 557 |
| 68 | 7.12 | 484 |
| 69 | 7.26 | 484 |
| 70 | 7.34 | 484 |
| 71 | 6.33 | 487 |
| 72 | 6.87 | 478 |
| 73 | 7.06 | 475 |
| 74 | 6.17 | 480 |
| 75 | 6.21 | 476 |
| 76 | 6.28 | 468 |
| 77 | 7.04 | 486 |
| 78 | 6.63 | 474 |
| 79 | 6.88 | 495 |
| 80 | 5.79 | 496 |
| 81 | 7.06 | 516 |
| 82 | 7.16 | 525 |
| 83 | 6.73 | 495 |
| 84 | 8.26 | 523 |
| 85 | 6.56 | 506 |
| 86 | 5.63 | 488 |
| 87 | 8.24 | 505 |
| 88 | 6.79 | 499 |
| 89 | 4.95 | 559 |
| 90 | 5.33 | 580 |
| 91 | 6.84 | 524 |
| 92 | 6.13 | 525 |
| 93 | 6.06 | 464 |
| 94 | 6.77 | 520 |
| 95 | 7.41 | 518 |
| 96 | 7.20 | 514 |
| 97 | 6.86 | 512 |
| 98 | 7.95 | 513 |
| 99 | 7.79 | 522 |
| 100 | 6.47 | 523 |
| 101 | 8.38 | 521 |
| 102 | 7.01 | 495 |
| 103 | 6.31 | 480 |
| 104 | 7.75 | 465 |
| 105 | 6.76 | 485 |
| 106 | 6.33 | 483 |
| 107 | 6.96 | 479 |
| 108 | 7.04 | 491 |
| 109 | 7.07 | 491 |
| 110 | 6.36 | 470 |
| 111 | 5.86 | 490 |
| 112 | 7.42 | 500 |
| 113 | 6.12 | 500 |
| 114 | 6.86 | 489 |
| 115 | 6.78 | 500 |
| 116 | 8.03 | 498 |
| 117 | 6.32 | 474 |
| 118 | 6.21 | 498 |
| 119 | 6.54 | 476 |
| 120 | 6.52 | 470 |
| 121 | 6.56 | 481 |
| 122 | 6.57 | 469 |
| 123 | 6.28 | 473 |
| 124 | 6.13 | 470 |
| 125 | 6.41 | 465 |
| 126 | 6.08 | 470 |
| 127 | 5.72 | 485 |
| 128 | 5.95 | 483 |
| 129 | 5.50 | 510 |
| 130 | 5.54 | 503 |
| 131 | 5.66 | 514 |
| 132 | 6.44 | 512 |
| 133 | 5.43 | 502 |
| 134 | 6.34 | 494 |
| 135 | 5.63 | 505 |
| 136 | 5.98 | 507 |
| 137 | 6.03 | 512 |
| 138 | 5.88 | 500 |
| 139 | 5.65 | 506 |
| 140 | 5.81 | 516 |
| 141 | 5.19 | 518 |
| 142 | 5.26 | 504 |
| 143 | 5.21 | 500 |
| 144 | 4.96 | 513 |
| 145 | 5.33 | 518 |
| 146 | 5.52 | 508 |
| 147 | 6.23 | 505 |
| 148 | 6.14 | 485 |
| 149 | 5.37 | 483 |
| 150 | 6.07 | 487 |
| 151 | 5.38 | 483 |
| 152 | 5.29 | 479 |
| 153 | 4.93 | 516 |
| 154 | 4.38 | 558 |
| 155 | 5.03 | 553 |
| 156 | 5.26 | 511 |
| 157 | 4.96 | 517 |
| 158 | 5.01 | 516 |
| 159 | 4.83 | 509 |
| 160 | 5.13 | 510 |
| 161 | 4.91 | 515 |
| 162 | 6.93 | 543 |
| 163 | 7.78 | 550 |
| 164 | 6.84 | 551 |
| 165 | 5.93 | 533 |
| 166 | 7.34 | 604 |
| 167 | 6.00 | 585 |
| 168 | 5.47 | 495 |
| 169 | 5.58 | 507 |
| 170 | 5.63 | 498 |
| 171 | 5.13 | 494 |
| 172 | 5.24 | 512 |
| 173 | 5.49 | 496 |
| 174 | 6.62 | 552 |
| 175 | 5.66 | 536 |
| 176 | 5.94 | 538 |
| 177 | 6.38 | 600 |
| 178 | 6.41 | 545 |
| 179 | 6.24 | 535 |
| 180 | 5.36 | 548 |
| 181 | 5.41 | 540 |
| 182 | 5.68 | 544 |
| 183 | 5.72 | 535 |
| 184 | 5.79 | 580 |
| 185 | 5.25 | 539 |
| 186 | 5.67 | 540 |
| 187 | 5.91 | 532 |
| 188 | 7.52 | 552 |
| 189 | 6.83 | 543 |
| 190 | 7.91 | 550 |
| 191 | 6.09 | 538 |
| 192 | 6.53 | 546 |
| 193 | 6.47 | 540 |
| 194 | 6.20 | 531 |

TABLE II-continued

| Compound No. | $\epsilon_{max}^{MeOH*}$ | $\lambda_{max}\ nm^{MeOH}$ |
|---|---|---|
| 195 | 5.99 | 542 |
| 196 | 5.10 | 475 |
| 197 | 4.96 | 463 |
| 198 | 5.28 | 466 |
| 199 | 6.69 | 476 |
| 200 | 6.92 | 450 |
| 201 | 6.47 | 535 |
| 202 | 7.06 | 504 |
| 203 | 8.38 | 488 |
| 204 | 6.25 | 525 |
| 205 | 7.69 | 493 |
| 206 | 7.57 | 498 |
| 207 | 7.37 | 474 |
| 208 | 6.55 | 519 |
| 209 | 8.75 | 490 |
| 210 | 6.23 | 463 |
| 211 | 3.95 | 479 |
| 212 | 5.24 | 498 |
| 213 | 7.35 | 478 |
| 214 | 3.94 | 489 |
| 215 | 5.50 | 460 |
| 216 | 4.29 | 540 |
| 217 | 8.48 | 480 |
| 218 | 8.10 | 500 |
| 219 | 6.20 | 468 |
| 220 | 7.32 | 497 |
| 221 | 6.01 | 455 |
| 222 | 8.10 | 484 |
| 223 | 9.13 | 509 |
| 224 | 7.02 | 481 |
| 225 | 4.42 | 439 |
| 226 | 6.99 | 475 |
| 227 | 6.77 | 540 |
| 228 | 11.3 | 578 |
| 229 | 9.71 | 579 |
| 230 | 10.7 | 568 |
| 231 | 6.16 | 522 |
| 232 | 7.19 | 604 |
| 233 | 5.36 | 501 |
| 234 | 7.78 | 518 |
| 235 | 6.18 | 486 |
| 236 | 7.68 | 493 |
| 237 | 8.41 | 510 |
| 238 | 7.82 | 503 |
| 239 | 4.89 | 506 |
| 240 | 5.64 | 560 |
| 241 | 6.58 | 579 |
| 242 | 5.24 | 525 |
| 243 | 6.18 | 567 |
| 244 | 8.06 | 500 |
| 245 | 7.98 | 485 |
| 246 | 8.20 | 484 |
| 247 | 9.47 | 565 |
| 248 | 11.5 | 564 |
| 249 | 8.12 | 584 |
| 250 | 6.63 | 563 |
| 251 | 5.45 | 590 |
| 252 | 7.02 | 488 |
| 253 | 7.17 | 485 |
| 254 | 6.71 | 483 |
| 255 | 8.79 | 521 |
| 256 | 7.04 | 605 |
| 257 | 7.05 | 513 |
| 258 | 8.19 | 504 |
| 259 | 6.90 | 504 |
| 260 | 7.55 | 522 |
| 261 | 7.24 | 524 |
| 262 | 5.29 | 548 |
| 263 | 6.83 | 514 |
| 264 | 7.11 | 520 |
| 265 | 7.25 | 502 |
| 266 | 6.41 | 510 |
| 267 | 7.88 | 519 |
| 268 | 7.49 | 524 |
| 269 | 7.64 | 529 |
| 270 | 7.88 | 526 |
| 271 | 7.96 | 513 |
| 272 | 7.34 | 520 |

*$\times 10^4$

The pharmaceutical compositions of this invention containing one, or more compounds of the General Formulas (I) to (V) described above can be effectively used to treat various types of cancer including melanomas, hepatomas, gliomas, neuroblastomas, sarcomas and carcinomas of the lung, colon, breast, bladder, ovary, testis, prostate, cervix, pancreas, stomach, small intestine and other organs.

The pharmaceutical compositions of this invention can contain one or more compounds of the General Formulas (I) to (V) described above and, if desired, can be employed in combination with other therapeutic agents including conventional anti-tumor agents known in the art. Suitable examples of such conventional anti-tumor agents which can be used include adriamycin, cisplatin, colchicine, CCNU (Lomastine), BCNU (Carmustine), Actinomycin D, 5-fluorouracil, thiotepa, cytosinearabinoside, cyclophosphamide, mitomycin C, and the like.

Suitable examples of pharmaceutical carriers or diluents which can be employed in the pharmaceutical composition of this invention in combination with the compound of the General Formulas (I) to (V) include glucose, sucrose, lactose, ethyl alcohol, glycerin, mannitol, sorbitol, pentaerythritol, diethylene glycol, triethylene glycol, ethylene glycol, propylene glycol, dipropylene glycol, polyethylene glycol 400, other polyethylene glycols, mono-, di- and triglycerides of saturated fatty acids such as glyceryl trilaurate, glyceryl monostearate, glyceryl tristearate and glyceryl distearate, pectin, starch, alginic acid, xylose, talc, lycopodium, oils and fats such as olive oil, peanut oil, castor oil, corn oil, wheat germ oil, sesame oil, cottonseed oil, sunflower seed oil and cod-liver oil, gelatin, lecithin, silica, cellulose, cellulose derivatives such as methyl hydroxypropyl cellulose, methyl cellulose, hydroxyethyl cellulose, magnesium and calcium salts of fatty acids with 12 to 22 carbon atoms such as calcium stearate, calcium laureate, magnesium oleate, calcium palmitate, calcium behenate and magnesium stearate, emulsifiers, esters of saturated and unsaturated fatty acids, e.g., having 2 to 22 carbon atoms, especially 10 to 18 carbon atoms, with monohydric aliphatic alcohols (e.g., having 1 to 20 carbon atoms such as alkanols) or polyhydric alcohols such as glycols, glycerine, diethylene glycol, pentaerythritol, ethyl alcohol, butyl alcohol, octadecyl alcohol and silicones such as dimethyl polysiloxane. Additional carriers conventionally used in pharmaceutical compositions may also be appropriate for this invention.

The pharmaceutically effective amount of the compound of the General Formulas (I) to (V) which can be employed and the mode or manner of administration will be dependent upon the nature of the cancer, the therapy sought, the severity of the disease, the degree of malignancy, the extent of metastatic spread, the tumor load, general health status, body weight, age, sex, and the (genetic) racial background of the patient. However, in general, suitable modes of administration include intravenous, intraperitoneal, intramuscular or intravesicular injection in the form of, for example, a compound of the General Formulas (I) to (V) in, e.g., a 5% glucose aqueous solution or with other appropriate carriers or diluents as described above. A suitable therapeutically effective amount of a compound of the General Formulas (I) to (V) in the composition is about 0.01% by weight to about 10% by weight, more generally 0.1% by weight to about 1% based on the weight of the composition.

Again, as noted above, pharmaceutically effective amounts will be generally determined by the practitioner based on the clinical symptoms observed and degree of progression of disease and like factors but a suitable therapeutically effective amount of the compound of the General Formulas (I) to (V) generally can range from 10 mg to 500 mg, more generally 100 mg to 200 mg, administered per day per 70 kg of body weight, in single or multiple doses, as determined appropriate for the therapy involved.

In order to demonstrate the effectiveness of the compounds of the General Formulas (I) to (V) and the pharmaceutical compositions and method of this invention, the following examples are given to demonstrate effectiveness and selectivity values for a number of the compounds of the initial General Formulas (I) to (V) employed in the composition and method of this invention as well as compounds for comparison. The results obtained are shown in the tables below.

EXAMPLE 1

The data obtained in Table III below were obtained in the following manner.

Human colon carcinoma cell line CX-1 or normal monkey kidney epithelial cell line CV-1 was chosen as representatives of cancer cells and normal cells, respectively. This assay demonstrates the selective killing of cancer cells by compounds of the General Formulas (I) to (V). CX-1 cells (2,000 cells/well) and CV-1 cells (1,000 cells/well) were plated in 24-well plastic culture plates. Compounds of General Formulas (I) to (V) were dissolved in dimethylsulfoxide at a concentration of 1 mg/ml and serial dilutions of this solution in cell culture media at concentrations varying from 20 μg/ml to 0.0025 μg/ml were added to individual wells. The control received culture media only. Cells were treated with compounds of General Formulas (I) to (V) at 37° C. for 24 hours. After rinsing with fresh culture medium three times, the cells were further incubated at 37° C. for 7 to 10 days. Cell colonies were fixed and stained with 2% crystal violet in 70% ethanol for 10 minutes and rinsed in water. The number of colonies in each well were counted and the concentration of compounds at which the colony number was reduced to 50% of the control ($IC_{50}$) was determined. The selectivity is defined as the ratio of $IC_{50}$ for CV-1 and $IC_{50}$ for CX-1.

TABLE III

| Compound No. | CV-1 ($IC_{50}$) μg/ml | CX-1 ($IC_{50}$) μg/ml | Selectivity |
|---|---|---|---|
| 2 | 10 | 0.03 | 333 |
| 3 | 6 | 0.03 | 200 |
| 7 | 1.5 | 0.005 | 300 |
| 8 | 20 | 0.04 | 500 |
| 9 | 20 | 0.04 | 500 |
| 10 | 20 | 0.04 | 500 |
| 11 | >20 | 0.03 | >667 |
| 12 | >20 | 0.03 | >667 |
| 13 | >20 | 0.03 | >667 |
| 14 | 20 | 0.03 | 667 |
| 15 | 20 | 0.02 | 1000 |
| 16 | 20 | 0.03 | 667 |
| 17 | 10 | 0.06 | 167 |
| 18 | 20 | 0.005 | 4000 |
| 19 | 10 | 0.02 | 500 |
| 20 | 2 | 0.02 | 100 |
| 21 | 8 | 0.01 | 800 |
| 22 | 10 | 0.01 | 1000 |
| 24 | 1.5 | 0.01 | 150 |
| 25 | 6 | 0.04 | 150 |
| 26 | 20 | 0.04 | 500 |

TABLE III-continued

| Compound No. | CV-1 ($IC_{50}$) μg/ml | CX-1 ($IC_{50}$) μg/ml | Selectivity |
|---|---|---|---|
| 27 | 20 | 0.03 | 667 |
| 28 | 7 | 0.04 | 175 |
| 29 | 10 | 0.03 | 333 |
| 30 | 2 | 0.01 | 200 |
| 31 | 10 | 0.03 | 333 |
| 32 | 6 | 0.04 | 150 |
| 34 | 8 | 0.03 | 267 |
| 35 | 6 | 0.04 | 150 |
| 38 | 10 | 0.03 | 333 |
| 39 | 20 | 0.04 | 500 |
| 40 | 6 | 0.03 | 200 |
| 42 | 2 | 0.02 | 100 |
| 43 | 2 | 0.01 | 200 |
| 46 | 10 | 0.1 | 100 |
| 47 | 6 | 0.04 | 150 |
| 50 | 8 | 0.04 | 200 |
| 53 | 10 | 0.04 | 250 |
| 54 | 20 | 0.05 | 400 |
| 57 | 6 | 0.05 | 120 |
| 82 | 20 | 0.05 | 400 |
| 83 | 6 | 0.05 | 120 |
| 85 | 6 | 0.008 | 750 |
| 63 | 20 | 0.2 | 100 |
| 65 | 20 | 0.2 | 100 |
| 92 | 20 | 0.04 | 500 |
| 94 | 20 | 0.05 | 400 |
| 95 | 20 | 0.04 | 500 |
| 96 | 20 | 0.06 | 333 |
| 99 | 10 | 0.1 | 100 |
| 108 | 1 | 0.01 | 100 |
| 109 | 20 | 0.05 | 400 |
| 110 | 10 | 0.05 | 200 |
| 115 | 6 | 0.05 | 120 |
| 117 | 4 | 0.03 | 133 |
| 121 | 20 | 0.1 | 200 |
| 163 | 20 | 0.03 | 667 |
| 204 | 20 | 0.03 | 667 |
| 210 | 10 | 0.1 | 100 |
| 215 | 10 | 0.05 | 200 |
| 223 | 20 | 0.1 | 200 |
| 224 | 20 | 0.08 | 250 |
| 227 | 8 | 0.08 | 100 |
| 238 | 20 | 0.05 | 400 |
| 239 | 20 | 0.1 | 200 |
| 253 | 6 | 0.05 | 120 |
| 254 | 6 | 0.05 | 120 |
| 255 | 5 | 0.05 | 100 |
| 256 | 4 | 0.02 | 200 |
| 277 | 10 | 0.05 | 200 |
| 278 | 20 | 0.08 | 250 |
| 307 | 6 | 0.05 | 120 |
| 309 | 4 | 0.01 | 400 |
| 311 | 20 | 0.03 | 667 |
| 314 | 10 | 0.05 | 200 |
| 316 | 1 | 0.01 | 100 |
| 335 | 26 | 0.1 | 200 |
| 337 | 8 | 0.08 | 100 |
| 86 | 10 | 0.05 | 200 |
| 87 | 20 | 0.05 | 400 |
| 90 | 8 | 0.04 | 200 |
| 91 | 20 | 0.04 | 500 |
| 98 | 8 | 0.05 | 160 |
| 104 | 18 | 0.1 | 180 |
| 105 | 6 | 0.05 | 120 |
| 114 | 6 | 0.05 | 120 |
| 129 | 10 | 0.1 | 100 |
| 131 | 6 | 0.05 | 120 |
| 244 | 0.05 | 10 | 200 |
| 245 | 0.02 | 7 | 350 |
| A | 0.6 | 0.03 | 20 |
| B | <0.1 | 0.05 | <2 |
| C | 2 | 0.04 | 50 |
| D | 1.5 | 0.03 | 50 |
| E | 6 | 0.5 | 12 |
| F | 1.5 | 0.03 | 50 |
| G | 0.1 | 0.02 | 5 |
| H | 0.1 | 0.04 | 2.5 |

Compounds A, B, C, D, E, F, G and H used for comparison were as follows:

| Compound No. | Structural Formula |
| --- | --- |
| A | ![Structure A: bis-benzothiazole trimethine cyanine with N-C2H5 groups, I− counterion] |
| B | ![Structure B: bis-naphthothiazole trimethine cyanine with N-C2H5 groups, I− counterion] |
| C | ![Structure C: benzoxazole-thiazole-tetrahydrobenzothiazole conjugate with N-C2H5 groups, I− counterion] |
| D | ![Structure D: bis-quinoline trimethine cyanine with N-C2H5 groups, I− counterion] |
| E | ![Structure E: bis-benzoxazole pentamethine cyanine with N-n-C3H7 groups, I− counterion] |
| F | ![Structure F: benzothiazole-benzoxazole pentamethine cyanine with N-C2H5 groups, Cl− counterion] |
| G | ![Structure G: bis-naphthothiazole methyl-substituted trimethine cyanine with N-C2H5 groups, Cl− counterion] |
| H | ![Structure H: bis-naphthothiazole chloro-substituted pentamethine cyanine with N-C2H5 groups, p-toluenesulfonate counterion] |

From the results set forth in Table III above, it is very clear that the compounds of the General Formulas (I) to (V) used in this invention have distinctively high selectivity values in comparison with Compounds A, B, C, D, E, F, G and H for comparison.

Based on information available in the literature. Compounds A and B with a selectivity of 20 and <2, respectively, would be highly toxic to animals and, therefore, humans. Indeed, it has been found that A and B are highly toxic to normal nude mice. Although Compounds C, D, E and F are less toxic to normal nude mice, because of its lower selectivity compared with other compounds of General Formulas (I) to (V), it is expected to have lower efficacy in treating cancers in animals as well as humans. Compounds G and H with a selectivity of 5 and 2.5, respectively, would be highly toxic to animals and, therefore, humans. Indeed, it has been found that compounds G and H are highly toxic to normal nude mice.

EXAMPLE 2

To further demonstrate the uniqueness of the present invention, compounds of the General Formulas (I) to (V) were tested using the protocol described in Example 1 except that the human bladder carcinoma EJ cell line was used instead of the human colon carcinoma cell line CX-1. The selectivity values, EJ values and CV-1 values for compounds of the present invention are shown in Table IV below.

TABLE IV

| Compound No. | CV-1 ($IC_{50}$) µg/ml | EJ ($IC_{50}$) µg/ml | Selectivity |
| --- | --- | --- | --- |
| 2 | 4 | 0.02 | 200 |
| 9 | 20 | 0.05 | 400 |
| 11 | >20 | 0.05 | >400 |
| 12 | >20 | 0.05 | >400 |
| 13 | 20 | 0.09 | 222 |
| 14 | 20 | 0.05 | 400 |
| 15 | 20 | 0.2 | 100 |
| 16 | 20 | 0.2 | 100 |
| 19 | 20 | 0.1 | 200 |
| 21 | 8 | 0.022 | 364 |
| 22 | 20 | 0.2 | 100 |
| 26 | 20 | 0.05 | 400 |
| 27 | 20 | 0.02 | 1000 |
| 29 | 10 | 0.05 | 200 |
| 31 | 10 | 0.02 | 500 |
| 82 | 20 | 0.015 | 1333 |
| 85 | 6 | 0.007 | 857 |
| 39 | 20 | 0.04 | 500 |
| 311 | 20 | 0.05 | 400 |
| 209 | 20 | 0.02 | 100 |
| 210 | 10 | 0.1 | 100 |
| 213 | 6 | 0.03 | 200 |
| 227 | 8 | 0.05 | 160 |
| 232 | 6 | 0.05 | 120 |
| 238 | 20 | 0.01 | 2000 |
| 239 | 20 | 0.08 | 250 |
| 253 | 6 | 0.02 | 300 |
| 254 | 6 | 0.01 | 600 |
| 319 | 6 | 0.02 | 300 |
| 254 | 6 | 0.01 | 600 |
| 335 | 20 | 0.1 | 200 |
| 315 | 20 | 0.005 | 4000 |
| 336 | 20 | 0.03 | 667 |
| 278 | 20 | 0.2 | 100 |
| 310 | 2 | 0.005 | 400 |
| 337 | 8 | 0.03 | 267 |

EXAMPLE 3

To further demonstrate the uniqueness of the present invention, compounds of the General Formulas (I) to (V) were tested using the protocol described in Example 1 except that the human melanoma LOX cell line was used instead of the human colon carcinoma cell line CX-1. The Selectivity values, LOX values and CV-1 values for compounds of the present invention are shown in Table V below.

TABLE V

| Compound No. | CV-1($IC_{50}$) µg/ml | LOX($IC_{50}$) µg/ml | Selectivity |
| --- | --- | --- | --- |
| 2 | 10 | 0.015 | 667 |
| 8 | 20 | <0.1 | >200 |
| 9 | >30 | 0.1 | >300 |
| 10 | >30 | 0.1 | >300 |
| 11 | >30 | <0.1 | >300 |
| 12 | >30 | <0.1 | >300 |
| 13 | >20 | 0.09 | >222 |
| 14 | >30 | <0.1 | >300 |
| 15 | 20 | 0.07 | 286 |
| 16 | 20 | 0.09 | 222 |
| 19 | 20 | <0.1 | >200 |
| 21 | 8 | 0.03 | 261 |
| 22 | 10 | 0.1 | 100 |
| 26 | 20 | 0.05 | 400 |
| 27 | 20 | 0.015 | 1333 |
| 29 | 10 | 0.03 | 333 |
| 31 | 10 | 0.04 | 250 |
| 82 | 20 | 0.064 | 312 |
| 85 | 6 | <0.01 | >600 |
| 39 | 20 | 0.03 | 666 |
| 204 | 20 | 0.09 | 222 |
| 209 | 20 | 0.2 | 100 |
| 213 | 6 | 0.03 | 200 |
| 214 | 20 | 0.04 | 500 |
| 215 | 20 | 0.04 | 500 |
| 224 | 20 | 0.1 | 200 |
| 227 | 8 | 0.03 | 267 |
| 232 | 6 | 0.02 | 300 |
| 238 | 20 | 0.02 | 1000 |
| 239 | 20 | 0.05 | 400 |
| 253 | 6 | 0.005 | 1200 |
| 254 | 6 | 0.005 | 1200 |
| 335 | 20 | 0.03 | 667 |
| 315 | 20 | 0.005 | 4000 |
| 336 | 20 | 0.005 | 4000 |
| 278 | 20 | 0.08 | 250 |
| 337 | 8 | 0.01 | 800 |
| 310 | 2 | 0.005 | 400 |
| 338 | 2 | 0.005 | 400 |
| 339 | 10 | 0.03 | 333 |
| 341 | 6 | 0.03 | 200 |

EXAMPLE 4

To further demonstrate the uniqueness of the present invention, compounds of the General Formulas (I) to (V) were tested using the protocol described in Example 1 except that the human breast carcinoma MCF-7 cell line was used instead of the human colon carcinoma cell line CX-1. The Selectivity values, MCF-7 values and CV-1 values for compounds of the General Formulas (I) to (V) used in the present invention are shown in Table VI below.

TABLE VI

| Compound No. | CV-1($IC_{50}$) µg/ml | MCF-7($IC_{50}$) µg/ml | Selectivity |
| --- | --- | --- | --- |
| 2 | 10 | 0.09 | 111 |
| 16 | 20 | 0.06 | 333 |
| 19 | 10 | 0.06 | 167 |
| 26 | 20 | 0.06 | 333 |
| 27 | 20 | 0.06 | 333 |
| 29 | 10 | 0.05 | 200 |
| 31 | 10 | 0.04 | 250 |
| 82 | 20 | 0.064 | 312 |
| 39 | 20 | 0.09 | 222 |
| 215 | 20 | 0.1 | 200 |
| 224 | 20 | 0.1 | 200 |
| 227 | 8 | 0.05 | 160 |
| 116 | 6 | 0.04 | 150 |
| 232 | 6 | 0.04 | 150 |
| 340 | 20 | 0.1 | 200 |
| 253 | 6 | 0.03 | 200 |
| 254 | 6 | 0.03 | 200 |
| 335 | 20 | 0.2 | 100 |
| 315 | 20 | 0.05 | 400 |
| 336 | 20 | 0.2 | 100 |
| 278 | 20 | 0.2 | 100 |

TABLE VI-continued

| Compound No. | CV-1(IC$_{50}$) µg/ml | MCF-7(IC$_{50}$) µg/ml | Selectivity |
|---|---|---|---|
| 337 | 8 | 0.05 | 160 |

EXAMPLE 5

To further demonstrate the uniqueness of the present invention, compounds of the General Formulas (I) to (V) were tested using the protocol described in Example 1 except that the human pancreatic carcinoma CRL 1420 cell line was used instead of the human colon carcinoma cell line CX-1. The Selectivity values, CRL 1420 values and CV-1 values for compounds of the General Formulas (I) to (V) used in the present invention are shown in Table VII below.

TABLE VII

| Compound No. | CV-1(IC$_{50}$) µg/ml | CRL-1420(IC$_{50}$) µg/ml | Selectivity |
|---|---|---|---|
| 2 | 10 | 0.01 | 1000 |
| 9 | 20 | 0.09 | 222 |
| 10 | 20 | 0.08 | 250 |
| 12 | 20 | 0.09 | 222 |
| 13 | >20 | 0.05 | >400 |
| 14 | 20 | 0.05 | 400 |
| 15 | 20 | 0.04 | 500 |
| 16 | 20 | 0.07 | 285 |
| 19 | 10 | 0.09 | 111 |
| 21 | 8 | 0.03 | 261 |
| 26 | 20 | 0.04 | 500 |
| 27 | 20 | 0.015 | 1333 |
| 29 | 10 | 0.02 | 500 |
| 82 | 20 | 0.015 | 1333 |
| 85 | 6 | 0.01 | 600 |
| 39 | 20 | 0.05 | 400 |
| 204 | 20 | 0.04 | 500 |
| 209 | 20 | 0.1 | 200 |
| 210 | 10 | 0.09 | 111 |
| 213 | 6 | 0.03 | 200 |
| 215 | 20 | 0.09 | 222 |
| 227 | 8 | 0.05 | 160 |
| 232 | 6 | 0.03 | 200 |
| 238 | 20 | 0.02 | 1000 |
| 239 | 20 | 0.05 | 400 |
| 253 | 6 | 0.03 | 200 |
| 254 | 6 | 0.005 | 1200 |
| 335 | 20 | 0.04 | 500 |
| 315 | 20 | 0.005 | 4000 |
| 336 | 20 | 0.03 | 667 |
| 310 | 2 | 0.005 | 400 |
| 237 | 8 | 0.03 | 267 |
| 341 | 6 | 0.03 | 200 |

EXAMPLE 6

Nude Mice Bearing Human Melanoma as a Model System

LOX, a human melanoma cell line, grown subcutaneously in nude mice was excised, trypsinized to yield a single cell suspension using a metal grid with a 4 mm mesh. Red blood cells were lysed by incubation with 0.17 molar ammonium chloride at 4° C. for 20 minutes. Five million viable trypan blue negative cells made up in 0.1 ml of Dulbecco modified Eagle medium (DMFE) were injected into the peritoneal cavity of a male athymic Swiss nu/nu mouse. The control group and each treatment group consisted of 5 to 10 mice. Treatment was commenced the following day by intraperitoneal injection.

Ten control mice received 0.25 ml of 2% dextrose on these days the treated groups were injected with the compounds of this invention. The compounds of the General Formulas (I) to (V) used in this invention which were tested are listed in Table VIII below and the results obtained are shown in Table VIII and FIG. 1~21 of the accompanying drawings. T/C is the ratio, expressed as a percentage of the mean survival age of the treated group to the mean survival age of the untreated control group.

TABLE VIII

Survival Rate (%) of Nude Mice Implanted with Human Melanoma LOX

| Test No. | Compound No. | Dose (mg/kg) | Schedule (i.p. on day) | T/C (%) |
|---|---|---|---|---|
| 1 | 2 | 5 | 1, 4, 8, 11, 15 | 163 |
| 2 | 8 | 5 | 1, 4, 8, 11, 15 | 142 |
| 3 | 9 | 5 | 1, 4, 8, 11, 15, 18 | 142 |
| 4 | 10 | 5 | 1, 4, 8, 11, 15, 18 | 171 |
| 5 | 11 | 5 | 1, 4, 8, 11 | 132 |
| 6 | 13 | 5 | 1, 4, 8, 11 | 147 |
| 7 | 14 | 5 | 1, 4, 8, 11 | 147 |
| 8 | 15 | 5 | 1, 4, 8, 11 | 163 |
| 9 | 16 | 5 | 1, 4, 8, 11 | 147 |
| 10 | 21 | 5 | 1, 5*, 8* | 133 |
| 11 | 22 | 5 | 1, 4, 8, 11 | 179 |
| 12 | 28 | 5 | 1, 2, 6, 9, 13, 16 | 1218 |
| 13 | 39 | 5 | 1, 4, 11, 15, 18 | 154 |
| 14 | 82 | 5 | 1, 4, 8, 11, 15 | 142 |
| 15 | 85 | 5 | 1, 4, 8, 11, 15 | 174 |
| 16 | 203 | 5 | 1, 5, 9, 13 | 139 |
| 17 | 7 | 5 | 1, 4, 8, 12 | 182 |
| 18 | 30 | 2.5 | 1, 4, 6, 8 | 171 |
| 19 | 31 | 5 | 1, 4, 8, 11 | 153 |
| 20 | 50 | 5 | 1, 2, 3, 6, 9, 10, 13 | 163 |
| 21 | 53 | 10 | 1, 2, 3, 5, 8, 10, 13 | 150 |
| 22 | 57 | 5 | 1, 2, 3, 6, 7, 8, 9, 10, 14 | 163 |
| 23 | 94 | 10 | 1, 3, 6, 8, 10, 13, 15 | 161 |
| 24 | 90 | 5 | 1, 8, 13 | 163 |
| 25 | 245 | 15 | 1, 5, 9, 13, 19 | 200 |
| 26 | 3 | 5 | 1, 4, 8, 11, 14, 16 | 218 |
| 27 | 92 | 2.5 | 1, 2, 3, 4, 6, 7, 8, 10, 11 | 186 |
| 28 | 244 | 10 | 1, 2, 6, 8, 13 | 150 |
| 29 | 87 | 10 | 1, 3, 6, 9, 10 | 150 |
| 30 | 109 | 10 | 1, 2, 3, 6, 8, 10, 13, 15 | 150 |
|  | 204 | 10 | 1, 4, 8, 10, 12 | >270 |
|  | 211 | 5 | 1, 4, 8, 10 | 194 |
|  | 214 | 10 | 1, 4, 8, 10, 12 | >300 |
|  | 215 | 3 | 1, 4, 8, 10, 12 | 167 |
|  | 224 | 3 | 1, 4, 8, 10, 12 | 161 |
|  | 232 | 3 | 1, 4, 8, 10, 12 | >270 |
|  | 283 | 5 | 1, 4, 8, 11, 14 | >350 |
|  | 340 | 8 | 1, 3, 8, 13 | 194 |
|  | 342 | 5 | 1, 5, 8, 11, 14 | >350 |
|  | 335 | 5 | 1, 5, 8, 11, 14 | 189 |
|  | 343 | 5 | 1, 3, 4, 6, 8, 10, 13 | 188 |
|  | 336 | 5 | 1, 3, 4, 6, 8, 10, 13 | 188 |
|  | 278 | 4 | 1, 3, 4, 6, 8, 10, 13 | 228 |
|  | 310 | 8 | 1, 3, 4, 6, 8, 10 | 206 |
|  | 338 | 4 | 1, 3, 4, 6, 8, 10, 13 | 194 |
|  | 337 | 5 | 1, 3, 4, 6, 8, 10, 13 | 137 |
|  | 344 | 5 | 1, 4, 8, 10, 12 | >288 |
|  | 316 | 5 | 1, 4, 8, 10, 12 | >340 |
|  | 256 | 5 | 1, 4, 8, 10, 12 | 171 |
|  | 339 | 5 | 1, 4, 8, 10, 12 | >340 |

*2.5 mg/kg

EXAMPLE 7

Anti-Human Colon Carcinoma CX-1 Activity Using Nude Mice

Human colon carcinoma cell line CX-1 has been chosen by the National Cancer Institute as a mode for cancer drug screening (NCI Protocol 3C2H2). It was established in culture from the surgical explant of the primary colon adenocarcinoma of a 44 year old woman with no previous chemotherapy. The cultured CX-1 cells, upon subcutaneous injection, can grow readily in nude mice as a moderately- to well-differentiated human colon carcinoma. CEA is expressed as expected for differentiated colon carcinoma cells. Abundant keratin, consistent with epithelial origin, is present. Increased uptake and prolonged retention of delocalized lipophilic cations are observed.

Swiss nu/nu mice obtained from Taconic Farm were housed in a pathogen-free environment. Tumors subcutaneously passaged in nude mice were excised under sterile conditions and converted to a single cell suspension using a metal grid with a 0.4 mm mesh. Red blood cells were lysed by incubation with 0.17M ammonium chloride at 4° C. for 20 minutes. Cells were scored for viability with trypan blue. Viable CX-1 cells (2.5 million) made up in 0.1 ml of cell culture mouse. The mice were randomly allocated into a control group (five mice) and a treatment group (five mice per group). The drug treatment was commenced the next day. Doses and schedules were developed empirically and were based mainly on information on LD50 and LD10 obtained from preliminary toxicity studies. The control group received an equivalent volume of hydroxypropyl-$\beta$-cyclodextrin-5% glucose solution.

The pharmaceutical compositions tested comprised solutions in 5% glucose subjected to sonication at concentrations of 1 mg/ml. Those compounds which were not completely dissolved by this procedure were dissolved hydroxypropyl-$\beta$-cyclodextrin using the following method. Hydroxypropyl-$\beta$-cyclodextrin (45 g) was mixed with 100 ml of sterilized, double distilled water and stirred for four hours. Each of the compounds to be tested (20 mg) was mixed with 10 ml of hydroxypropyl-$\beta$-cyclodextrin solution and sonicated for 60 minutes in the dark. This solution was then diluted in 5% glucose to yield a final compound concentration of 0.5 mg/ml, and further sonicated for 60 minutes in the dark to assure that the compound was completely dissolved.

When the growth of tumors in the control group reached the exponential phase and the size of the tumor was palpable (usually 20 to 30 days after tumor implantation), the experiments were terminated. Tumors in each mouse were excised and weighed using an analytical balance. Total tumor weight in each group from five mice was calculated. Per cent tumor inhibition between the treated group and the control group was then calculated for each group.

The results obtained are shown in Table IX below and graphically in FIGS. 22–25.

TABLE IX

| Test No. | Compound No. | Dose (mg/kg) | Schedule (i.p. on day) | Tumor Inhibition (%) |
|---|---|---|---|---|
| 3-1 | 8 | 5 | 1, 5, 9, 13 | 55.1 |
| 3-2 | 9 | 5 | 1, 9, 13 | 45.2 |
| 3-3 | 10 | 5 | 1, 5, 9, 13 | 66.0 |
| 3-4 | 13 | 20 | 1, 5, 8, 12, 15, 19 | 87.7 |
| 3-5 | 16 | 5 | 1, 5, 8, 12, 15, 19 | 82.9 |
| 3-6 | 19 | 5 | 1, 9, 13 | 60.4 |
| 3-7 | 21 | 2.5 | 1, 5, 8, 12 | 50.2 |
| 3-8 | 26 | 5 | 1, 5, 8, 11 | 53.6 |
| 3-9 | 27 | 2.5 | 1, 5, 8 | 40.9 |
| 3-10 | 28 | 5 | 1, 4, 8, 12, 16, 21 | 68.8 |
| 3-11 | 39 | 5 | 1, 5, 8, 11 | 74.9 |
| 3-12 | 203 | 5 | 1, 5, 8, 11 | 71.9 |
| 3-13 | 7 | 5 | 1, 5, 7 | 42.0 |
| 3-15 | 57 | 10 | 1, 2, 5, 6, 7, 8 | 66.3 |

While the invention has been described in detail and with reference to specific embodiments thereof, it will be apparent to one skilled in the art that various changes and modifications can be made without departing from the spirit and scope of the invention.

What is claimed is:

1. A pharmaceutical composition for treatment of cancer comprising:
   (A) a therapeutically effective amount of at least one compound selected from the group consisting of compounds represented by the General Formula (I)

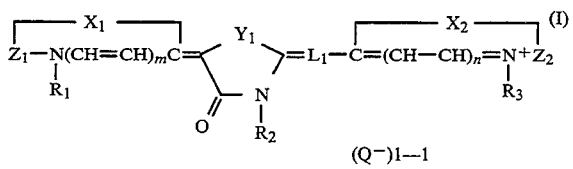

(Q$^-$)1—1 wherein $X_1$ and $X_2$, which may be same or different, each represents O, S, Se, —CH=CH—,

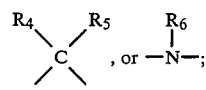

$Y_1$ represents O, S, Se, or

$R_1$ and $R_3$, which may be the same or different, each represents an alkyl group having 1–15 carbon atoms;

$R_2$ represents an alkyl group having 1–15 carbon atoms, an aryl group having 6–20 carbon atoms or a heterocyclic group selected from the group consisting of an imidazole ring, a thiazole ring, a pyrrole ring, a pyrazole ring, a furan ring, a thiphene ring, a piperidine ring, a morpholine ring, a piperadine ring, a pyrazine ring, a pyridine ring, and a pyrimidine ring;

$Z_1$ together with

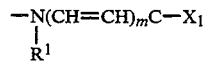

represents a thiazole ring, a benzothiazole ring, a naphthothiazole ring, an oxazole ring, a benzoxazole ring, a naphthoxazole ring, a selenazole ring, a benzoselenazole ring, a thiazoline ring, a 2-pyridine ring, a 4-pyridine ring, a 2-quinoline ring, a 4-quinoline ring, a 1-isoquinoline ring, a 3,3-dialkylindolenine ring, an imidazole ring, a benzimidazole ring, and a naphthimidazole ring;

$Z_2$ together with

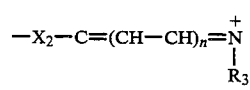

represents a thiazole a benzothiazole ring, a naphthothiazole ring, an oxazole ring, a benzoxazole ring, a naphthoxazole ring, a selenazole ring, a benzoselenazole ring, a thiazoline ring, a 2-pyridine ring, a 4-pyridine ring, a 2-quinoline ring, a 4-quinoline ring, a 1-isoquinoline ring, a 3,3-dialkylindolenine ring, an imidazole ring, a benzimidazole ring, and a naphthimidazole ring;

L₁ represents a methine group or L₁ and R₃ may combine and form a ring selected from the group consisting of a pyrroline ring, a tetrahydropyridine ring and an oxazine ring;

R₄ and R₅, which may be the same or different, each represents an alkyl group having 1-15 carbon atoms;

R₆ and R₇, which may be the same or different, each represents an alkyl group having 1-15 carbon atoms or an aryl group having 6-20 carbon atoms;

Q represents a pharmaceutically acceptable anion;

l represents 1 or 2;

m and n, which may be the same or different, each represents 0 or 1; and (B) a pharmaceutically acceptable carrier or diluent.

2. The composition of claim 1, wherein said at least one compound of the General Formula (I) is a compound selected from the group consisting of compounds represented by the General Formula (II)

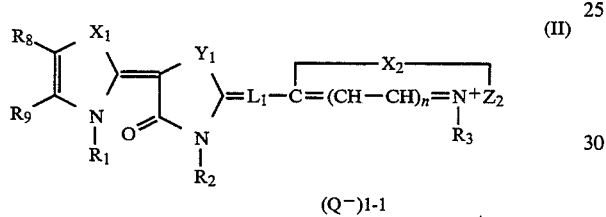

(Q⁻)ₗ₋₁ wherein

Z₂, Y₁, X₁, X₂, R₁, R₂, R₃, L₁, Q, l and n all have the same meanings as defined in claim 1;

R₈ and R₉, which may be the same or different, each represents a hydrogen atom, an alkyl group having 1-15 carbon atoms or an aryl group having 6-20 carbon atoms, or R₈ and R₉ may combine and form a ring selected from the group consisting of a benzene, a naphthalene ring, a dihydronaphthalene ring, an anthracene ring and a phenanthrene ring.

3. The composition of claim 2, wherein the compound is selected from the group consisting of compounds represented by the General Formula (IIA)

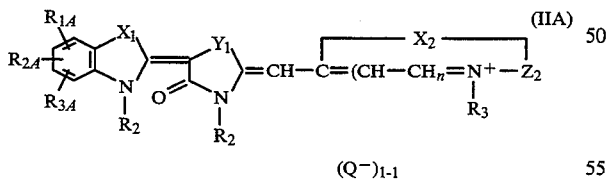

(Q⁻)ₗ₋₁ wherein

X₁, Y₁, R₄, R₅, Q, l, and n have the same meanings as defined in claim 2;

X₂ represents O, S, Se, —CH=CH— or —CR₄R₅—;

R₁ and R₃, which may be the same or different, each represents an alkyl group having 1 to 8 carbon atoms;

R₂ represents an alkyl group having 1 to 8 carbon atoms or an aryl group having 6 to 8 carbon atoms;

R₁ₐ, R₂ₐ and R₃ₐ, which may be the same or different, each represents a hydrogen atom, a halogen atom, a hydroxy group, an alkyl group having 1-9 carbon atoms, an aryl group having 6-9 carbon atoms, an alkoxy group having 1-5 carbon atoms, an aryloxy group having 6-10 carbon atoms, an alkoxycarbonyl group having 2-6 carbon atoms, an acylamino group having 2-7 carbon atoms, a sulfonylamino group having up to 6 carbon atoms, an acyl group having 2-7 carbon atoms, a cyano group, a nitro group, a carbamoyl group having 1-6 carbon atoms, a sulfamoyl group having up to 5 carbon atoms, an acyloxy group having 1-7 carbon atoms, an amino group having up to 6 carbon atoms, an alkanesulfonyl group having 1-2 carbon atoms, an allenesulfonyl group having 6-7 carbon atoms, an alkylthio group having 1-3 carbon atoms, an arylthio group having 6-7 carbon atoms or a heteroring residue;

Z₂ together with

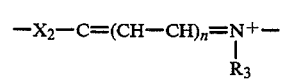

represents a thiazole ring, a benzothiazole ring, a naphthothiazole ring, an oxazole ring, a benzoxazole ring, a naphthoxazole ring, a selenazole ring, a benzoselenazole ring, a thiazoline ring, a 2-pyridine ring, a 4-pyridine ring, a 2-quinoline ring, a 4-quinoline ring, a 1-isoquinoline ring, a 3,3-dialkylindolenine ring, an imidazole ring, a benzimidazole ring, and a naphthimidazole ring.

4. The composition of claim 3, wherein in the General Formula (IIA), X₁ represents O, S, Se, —CH=CH—, —C(CH₃)₂—, —NCH₃—, —NCH₂CH₃— or =N(phenyl);

X₂ represents O, S, Se, —CH=CH— or —C(CH₃)₂—;

Y₁ represents O, S, Se, —NCH₃—, —NCH₂CH₃— or =N(phenyl);

R₁ₐ, R₂ₐ, and R₃ₐ, which may be the same or different, each represents a hydrogen atom, a halogen atom, a hydroxy group, an alkyl group having 1 to 5 carbon atoms, a phenyl group, an alkoxy group having 1 to 5 carbon atoms, a phenoxy group or an alkoxycarbonyl group having 2 to 6 carbon atoms;

Z₂ together with

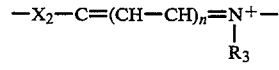

represents a thiazole ring, a benzothiazole ring, a naphthothiazole ring, a benzoxazole ring, a naphthoxazole ring, a benzoselenazole ring, a thiazoline ring, a 2-pyridine ring, a 4-pyridine ring, a 2-quinoline ring, a 4-quinoline ring or a 3,3-dimethylindolenine ring.

5. The composition of claim 4, wherein, in the General Formula (IIA), X₁ represents O, S or —CH=CH—;

X₂ represents O, S, Se or —CH=CH—;

Y₁ represents S;

Z₂ together with

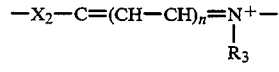

represents a thiazole ring, a benzothiazole ring, a naphthothiazole ring, a benzoxazole ring, a naphthoxazole ring, a benzoselenazole ring, a thiazoline ring, a 2-pyridine ring, a 4-pyridine ring, a 2-quinoline ring or a 4-quinoline ring.

6. The composition of claim 5, wherein, in the General Formula (IIA) $X_1$ represents S and at least one of $R_{1A}$, $R_{2A}$ and $R_{3A}$ is a hydrogen atom.

7. The composition of claim 5, wherein, in the General Formula (IIA), $X_1$ represents O and at least one of $R_{1A}$, $R_{2A}$ and $R_{3A}$ is a hydrogen atom.

8. The composition of claim 6, wherein the compound is selected from the group consisting of compounds represented by the General Formula (IIB).

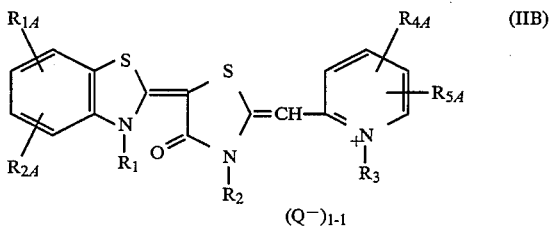

wherein
$R_1$ and $R_3$, which may be the same or different, each represents an alkyl group having 1 to 8 carbon atoms;

$R_2$ represents an alkyl group having 1 to 8 carbon atoms or an aryl group having 6 to 8 carbon atoms;

$R_{1A}$ and $R_{2A}$, which may be the same or different, each represents a hydrogen atom, a halogen atom, a hydroxy group, an alkyl group having 1 to 5 carbon atoms, a phenyl group, an alkoxy group having 1 to 5 carbon atoms, a phenoxy group or an alkoxycarbonyl group having 2 to 6 carbon atoms;

$R_{4A}$ and $R_{5A}$, which may be the same or different, each represents a hydrogen atom, a chlorine atom, an alkyl group having 1 to 5 carbon atoms or a methoxycarbonyl group; and Q and l have the same meanings as defined in claim 2.

9. The composition of claim 8, wherein, in the General Formula (IIB), $R_1$ and $R_3$, which may be the same or different, each represents a methyl group, an ethyl group, a propyl group or a butyl group;

$R_2$ represents a methyl group, and ethyl group, allyl group or a phenyl group;

$R_{1A}$ and $R_{2A}$, which may be the same or different, each represents a hydrogen atom, a methyl group, a methoxy group, a chlorine atom or a methoxycarbonyl group;

$R_{4A}$ and $R_{5A}$, which may be the same or different, each represents a hydrogen atom, a chlorine atom, a methyl group or a methoxycarbonyl group;

Q represents a chlorine ion, a bromine ion, an iodine ion or an acetic acid ion: and l represents 2.

10. The composition of claim 2, wherein, in the General Formula (II), $X_1$ represents O, S or $-NR_6-$;

$X_2$ represents O, S, Se or $-CH=CH-$;

$Y_2$ represents O, S or $-NR_7-$;

$R_1$ and $R_3$, which may be the same or different, each represents an alkyl group having 1 to 8 carbon atoms;

$R_2$ represents an alkyl group having 1 to 8 carbon atoms or an aryl group having 6 to 8 carbon atoms;

$R_6$ and $R_7$, which may be the same or different, each represents an alkyl group or an aryl group;

$R_8$, and $R_9$, which may be the same or different, each represents a hydrogen atom, an alkyl group or an aryl group.

11. The composition of claim 10, wherein $X_1$ represents O, S, $-NCH_3-$, $-NCH_2CH_3-$ or $-NCH_2CH_2OCH_3-$;

$Y_1$ represents O, S, $-NCH_3-$, $-NCH_2CH_3-$ or $-N(phenyl)-$; and $R_8$ and $R_9$, which may be the same or different, each represents a hydrogen atom or methyl group.

12. The composition of claim 2, wherein in the General Formula (II), $X_1$ represents O, S, or $-NR_6-$;

$X_2$ represents O, S, Se or $-CH=CH-$;

$Y_1$ represents S;

$R_1$ and $R_3$, which may be the same or different, each represents an alkyl group having 1 to 8 carbon atoms;

$R_2$ represents an alkyl group having 1 to 8 carbon atoms or an aryl group having 6 to 8 carbon atoms;

$R_6$ is as defined in claim 2;

$R_8$ and $R_9$ together represent an atomic group necessary to form a naphthalene ring, a dihydronaphthalene ring, an anthracene ring or a phenanthrene ring.

13. The composition of claim 12, wherein $X_1$ represents O or S;

$R_8$ and $R_9$ together represent an atomic group necessary to form a naphthalene ring or a dihydronaphthalene ring;

$Z_2$ represents a thiazole ring, a benzothiazole ring, a naphthothiazole ring, a benzoxazole ring, a naphthoxazole ring, a benzoselenazole ring, a thiazoline ring, a 2-pyridine ring, a 4-pyridine ring, a 2-quinoline ring, or a 4-quinoline ring.

14. The composition of claim 12, wherein $X_1$ represents S;

$X_2$ represents O, S or $-CH=CH-$;

$R_1$ represents a methyl group, an ethyl group or a propyl group;

$R_2$ and $R_3$, which may be the same or different, each represents a methyl group or an ethyl group;

$R_8$ and $R_9$ together represent an atomic group necessary to form a naphthalene ring or a dihydronaphthalene ring;

$Z_2$ represents a thiazole ring, a benzothiazole ring, a naphthothiazole ring, a benzoxazole ring, a naphthoxazole ring, a benzoselenazole ring, a thiazoline ring, a 2-pyridine ring, a 4-pyridine ring, a 2-quinoline ring, or a 4-quinoline ring; and l represents 2.

15. The composition of claim 12, wherein X1 represents O;

$X_2$ represents O, S or $-CH=CH-$;

$R_1$ represents a methyl group;

$R_2$ represents an ethyl group;

$R_3$ represents a methyl group or an ethyl group;

$R_8$ and $R_9$ together represent an atomic group necessary to form a naphthalene ring;

$Z_2$ represents a thiazole ring, a benzothiazole ring, a naphthothiazole ring, a benzoxazole ring, a naphthoxazole ring, a benzoselenazole ring, a thiazoline ring, a 2-pyridine ring, a 4-pyridine ring, a 2-quinoline ring, or a 4-quinoline ring; and l represents 2.

16. The composition of claim 1, wherein said at least one compound of the General Formula (I) is a compound selected from the group consisting of compounds represented by the General Formula (III)

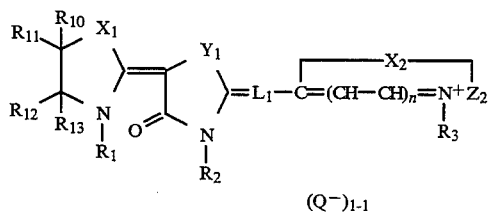

(III)

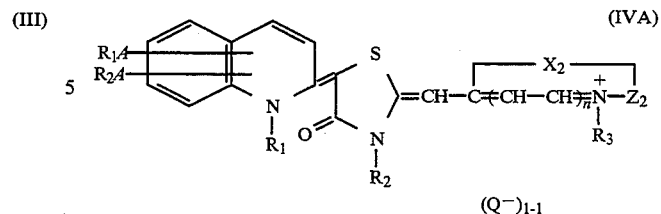

(IVA)

wherein $Z_2$, $Y_1$, $X_1$, $X_2$, $R_1$, $R_2$, $R_3$, $L_1$, $Q$, $l$ and $n$ all have the same meanings as defined in claim 1;

$R_{10}$, $R_{11}$, $R_{12}$ and $R_{13}$, which may be the same or different, each represents a hydrogen atom, an alkyl group or an aryl group, or any two of $R_{10}$, $R_{11}$, $R_{12}$ and $R_{13}$ may combine and form a fused 5- or 6-membered ring.

17. The composition of claim 16, wherein $X_1$, $X_2$ and $Y_1$ represents S;

$R_1$ and $R_2$, which may be the same or different, each represents an alkyl group having 1 to 3 carbon atoms;

$R_3$ represents an alkyl group having 1 to 5 carbon atoms;

$R_{10}$, $R_{11}$, $R_{12}$ and $R_{13}$ each represents a hydrogen atom;

$Z_2$ represents a thiazole ring, a benzothiazole ring or a naphthothiazole ring;

$L_1$ represents a methine group; and $l$ represents 2 and $n$ represents 0.

18. The composition of claim 1, wherein said at least one compound of the General Formula (I) is a compound selected from the group consisting of compounds represented by the General Formula (IV)

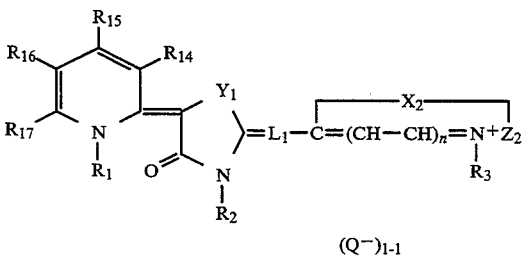

(IV)

wherein $Y_1$, $X_2$, $Z_2$, $R_1$, $R_2$, $R_3$, $Q$, $l$, $L_1$ and $n$ have the same meanings as defined in claim 1; $R_{14}$, $R_{15}$, $R_{16}$ and $R_{17}$, which may be the same or different, each represents a hydrogen atom, an alkyl group, an aryl group, an aryloxy group, an alkoxy group, an acyl group, an alkoxycarbonyl group, a benzoyl group, an ureido group, an amino group, an amido group, a sulfamido group, a carbamoyl group, a sulfamoyl group, a halogen atom, a nitro group, a cyano group, a hydroxy group, a carboxyl group, or any adjacent two of $R_{14}$ to $R_{17}$ may combine and form a 5- or 6-membered ring.

19. The composition of claim 18, wherein the compound is selected from the group consisting of compounds represented by the General Formula (IVA)

wherein $X_2$ represents O, S, Se or —CH=CH—;

$R_1$ and $R_3$, which may be the same or different, each represents an alkyl group having 1 to 8 carbon atoms;

$R_2$ represents an alkyl group having 1 to 8 carbon atoms or an aryl group having 6 to 8 carbon atoms;

$R_{1A}$ and $R_{2A}$, which may be the same or different, each represents a hydrogen atom, a halogen atom, a hydroxy group, an alkyl group, an aryl group, an alkoxy group, an aryloxy group or an alkoxycarbonyl group;

$Z_2$ represents a thiazole ring, a benzothiazole ring, a naphthothiazole ring, a benzoxazole ring, a naphthoxazole ring, a benzoselenazole ring, a thiazoline ring, a 2-pyridine ring, a 4-pyridine ring, a 2-quinoline ring, or a 4-quinoline ring; and $Q$, $l$ and $n$ have the same meanings as defined in claim 18.

20. The composition of claim 18, wherein the compound is selected from the group consisting of compounds represented by the General Formula (IVB)

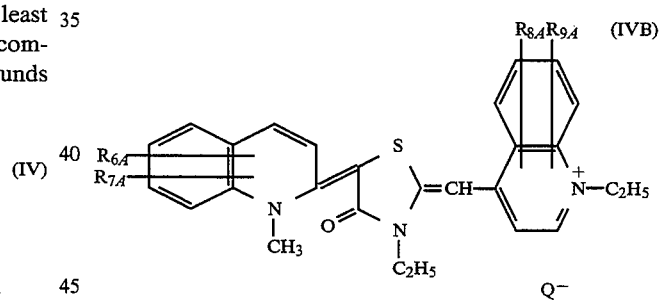

(IVB)

wherein $R_{6A}$, $R_{7A}$, $R_{8A}$ and $R_{9A}$ each represents a hydrogen atom, a chlorine atom, an ethoxy group, a hydroxy group, a methyl group, a dimethylcarbamoyl group, or an acetylamino group and $Q$ has the same meanings as defined in claim 18.

21. The composition of claim 1, wherein said at least one compound of the General Formula (I) is a compound selected from the group consisting of compounds represented by the General Formula (V)

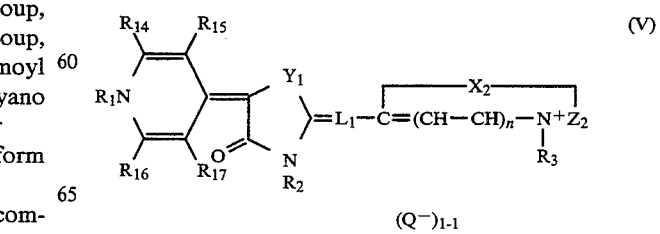

(V)

wherein $Y_1$, $X_2$, $Z_2$, $R_1$, $R_2$, $R_3$, Q, l, $L_1$ and n have the same meanings as defined in claim 1;

$R_{14}$, $R_{15}$, $R_{16}$ and $R_{17}$, which may be the same or different, each represents a hydrogen atom, an alkyl group, an aryl group, an alkoxy group, an acyl group, an alkoxycarbonyl group, a benzoyl group, an ureido group, an amino group, an amido group, a sulfamido group, a carbamoyl group, a sulfamoyl group, a halogen atom, a nitro group, a cyano group, a hydroxy group, a carboxyl group, or any adjacent two of $R_{14}$ to $R_{17}$ may combine and form a 5- or 6-membered ring.

22. The composition of claim 21, wherein in the General Formula (V) $X_2$ represents O, S, Se or —CH═CH—;

$Y_1$ represents S;

$R_1$ and $R_3$, which may be the same or different, each represents an alkyl group having 1 to 3 carbon atoms; and $R_2$ represents an alkyl group having 1 to 8 carbon atoms.

23. The composition of claim 1, wherein $Y_1$ represents S.

24. The composition of claim 2, wherein $Y_1$ represents S.

25. The composition of claim 2 wherein $R_2$ is a pyridine ring.

26. The composition of claim 1 wherein said alkyl group represented by $R_1$, $R_2$, $R_3$, $R_4$, $R_5$, $R_6$, and $R_7$ may be substituted or unsubstituted, and when substituted, said alkyl group represented by $R_1$, $R_2$, $R_3$, $R_4$, $R_5$, $R_6$, and $R_7$ may be substituted with a substituent selected from the group consisting of a halogen atom, an aryl group, an alkoxy group, and a hydroxy group;

wherein said aryl group represented by $R_2$, $R_6$, and $R_7$ may be substituted or unsubstituted, and when substituted, said aryl group represented by $R_2$, $R_6$, and $R_7$ may be substituted with a substitutent selected from the group consisting of a halogen atom, an alkyl group, an alkoxy group, a hydroxy group, a nitro group, a cyano group, an amino group, an alkyl- or aryl-substituted amino group, an acylamino group, a sulfonylamino group, a carbamoyl group, an acylamino group, sulfonylamino group, a carbamoyl group, a sulfamoyl group, a carboxyl group, and an alkoxycarbonyl group;

wherein said heterocyclic group represented by $R_2$ may be substituted or unsubstituted, and when substituted, said heterocyclic group represented by $R_2$ may be substituted by a substituent selected from the group consisting of a halogen atom, an alkyl group, an alkoxy group, a hydroxy group, a nitro group, a cyano group, an amino group, an alkyl- or aryl-substituted amino group, an acylamino group, a sulfonylamino group, a carbamoyl group, a sulfamoyl group, a carboxyl group, and an alkoxycarbonyl group; and wherein $L_1$ may be substituted or unsubstituted, and when substituted, $L_1$ may be substituted with a substituent selected from the group consisting of an alkyl group, an aryl group, a halogen atom, and an alkoxy group.

* * * * *